(12) United States Patent
Kim

(10) Patent No.: US 12,084,721 B2
(45) Date of Patent: Sep. 10, 2024

(54) INFLAMMATORY BOWEL DISEASE DIAGNOSTIC METHOD BY MEANS OF BACTERIAL METAGENOMIC ANALYSIS

(71) Applicant: MD HEALTHCARE INC., Seoul (KR)

(72) Inventor: Yoon-Keun Kim, Gyeonggi-do (KR)

(73) Assignee: MD HEALTHCARE INC., Seoul (KR)

( * ) Notice: Subject to any disclaimer, the term of this patent is extended or adjusted under 35 U.S.C. 154(b) by 759 days.

(21) Appl. No.: 17/256,266

(22) PCT Filed: Jun. 21, 2019

(86) PCT No.: PCT/KR2019/007538
§ 371 (c)(1),
(2) Date: Dec. 28, 2020

(87) PCT Pub. No.: WO2020/004874
PCT Pub. Date: Jan. 2, 2020

(65) Prior Publication Data
US 2022/0267850 A1    Aug. 25, 2022

(30) Foreign Application Priority Data

Jun. 28, 2018   (KR) .................. 10-2018-0074992

(51) Int. Cl.
*C12Q 1/68*        (2018.01)
*C12Q 1/6883*      (2018.01)
(Continued)

(52) U.S. Cl.
CPC ............ *C12Q 1/6883* (2013.01); *C12Q 1/689* (2013.01); *C12Q 1/686* (2013.01)

(58) Field of Classification Search
CPC ....... C12Q 1/6883; C12Q 1/689; C12Q 1/686
See application file for complete search history.

(56) References Cited

U.S. PATENT DOCUMENTS 11,193,173 B2 *  12/2021  Kim ................. A61P 43/00
11,666,607 B2 *   6/2023  Kim ................. A23L 33/10
                                              424/450
2013/0121968 A1   5/2013  Quay

FOREIGN PATENT DOCUMENTS

CN       108866051 A  * 11/2018
KR     20110073049 A     6/2011
(Continued)

OTHER PUBLICATIONS

Mitsuhashi et al. (Inflamm Bowel Dis, 2016, 22(7):1587-1595) (Year: 2016).*

(Continued)

*Primary Examiner* — Stephanie K Mummert
(74) *Attorney, Agent, or Firm* — Riverside Law LLP

(57) ABSTRACT

The present invention relates to a method for prognosing the occurrence and the causative factor of an inflammatory bowel disease such as ulcerative colitis and Crohn's disease by means of a metagenomic analysis of bacterial and bacterial-derived vesicles present in a human body-derived substance and, more particularly, to a method for diagnosing the causative factor and occurrence risk of an inflammatory bowel disease by analyzing a metagenomic sequence present in bacteria and bacteria-derived vesicles present in stool. Trillions of bacteria are present in the intestine, and vesicles are secreted outside the cells for exchange of information. Bacterial are not absorbed into the intestinal epithelial cells, but the vesicles secreted from the bacteria pass through the mucous, are absorbed into the intestinal epithelial cells and can increase or reduce inflammation. The present invention can be facilitated as a method for diagnosing the occurrence risk and causative factor of an inflammatory bowel disease by means of a gene metagenomic sequence analysis of bacteria and bacterial=-derived vesicles present in a human body-derived substance. Also, the present invention enables (Continued)

early diagnosis even after an occurrence of an inflammatory bowel disease, reduces the occurrence of an inflammatory bowel disease, and can enhance therapeutic effects.

1 Claim, 26 Drawing Sheets

Specification includes a Sequence Listing.

(51) Int. Cl.
*C12Q 1/689* (2018.01)
*C12Q 1/686* (2018.01)

(56) References Cited

FOREIGN PATENT DOCUMENTS

| KR | 20160073157 A | 6/2016 |
| KR | 20160110232 A | 9/2016 |
| KR | 20160110336 A | 9/2016 |
| KR | 20180006303 A | 1/2018 |
| KR | 20180018354 A | 2/2018 |

OTHER PUBLICATIONS

Lowe et al. (Nucleic Acids Research, 1990, 18(7):1757-1761) (Year: 1990).*
Zhang et al. (Nature Communications, 2018, 9:2873, p. 1-14) (Year: 2018).*
Fabrega et al. (Frontiers in Microbiol, 2017, 8:1274, p. 1-13) (Year: 2017).*
Conte et al. (BMC Research, 2014, 7:748, p. 1-12) (Year: 2014).*
Zeller, G. et al., "Potential of fecal microbiota for early-stage detection of colorectal cancer", Molecular Systems Biology, 2014, vol. 10, 766, pp. 1-18.

* cited by examiner

```
                       SEQUENCE LISTING

<160> NUMBER OF SEQ ID NOS: 2

<210> SEQ ID NO 1
<211> LENGTH: 50
<212> TYPE: DNA
<213> ORGANISM: Artificial Sequence
<220> FEATURE:
<223> OTHER INFORMATION: 16S_V3_F
<220> FEATURE:
<221> NAME/KEY: misc_feature
<222> LOCATION: (42)..(42)
<223> OTHER INFORMATION: n is a, c, g, or t

<400> SEQUENCE: 1
tcgtcggcag cgtcagatgt gtataagaga cagcctacgg gnggcwgcag              50

<210> SEQ ID NO 2
<211> LENGTH: 55
<212> TYPE: DNA
<213> ORGANISM: Artificial Sequence
<220> FEATURE:
<223> OTHER INFORMATION: 16S_V4_R

<400> SEQUENCE: 2
gtctcgtggg ctcggagatg tgtataagag acaggactac hvgggtatct aatcc         55
```

INFLAMMATORY BOWEL DISEASE DIAGNOSTIC METHOD BY MEANS OF BACTERIAL METAGENOMIC ANALYSIS

CROSS-REFERENCE TO RELATED APPLICATIONS

This application is the U.S. national phase application filed under 35 U.S.C. § 371 claiming benefit to International Patent Application No. PCT/KR2019/007538, filed on Jun. 21, 2019, which claims priority to Korean Patent Application No. 10-2018-0074992, filed Jun. 28, 2018, the disclosures of which are incorporated herein by reference in their entirety.

REFERENCE TO A "SEQUENCE LISTING," A TABLE, OR A COMPUTER PROGRAM LISITING APPENDIX SUBMITTED AS AN ASCII TEXT FILE

The present application hereby incorporates by reference the entire contents of the text file named "206132-0108-00US Sequence Listing v2.txt" in ASCII format. The text file containing the Sequence Listing of the present application was created on Jul. 9, 2021, and is 854 bytes in size.

TECHNICAL FIELD

The present invention relates to a method of diagnosing an inflammatory bowel disease through bacterial metagenomic analysis, and more particularly, to a method of diagnosing an inflammatory bowel disease such as ulcerative colitis or Crohn's disease by analyzing the increase or decrease in content of specific bacteria or bacteria-derived vesicles by performing bacterial metagenomic analysis using a subject-derived sample.

BACKGROUND ART

Inflammatory bowel disease (IBD) refers to chronic inflammatory diseases that are generated in the intestines, and representative examples among the inflammatory bowel disease are ulcerative colitis and Crohn's disease whose causes are unclear. The most basic test for diagnosing inflammatory bowel disease provides information necessary for the diagnosis and differentiation of an inflammatory disease occurring in the intestines through endoscopy.

Ulcerative colitis is a disease characterized by inflammation and ulcers occurring in the colon and rectum, and the cause of the disease is unknown. Crohn's disease has an unknown cause and is a chronic inflammatory bowel disease which occurs in the digestive tract from the mouth to the anus. It is known that the inflammatory bowel disease has a higher prevalence in North America and Europe than in other regions, and according to statistics in 2015, approximately 12 million people are suffering from ulcerative colitis and Crohn's disease worldwide, and the prevalence of these diseases is 1 to 20 per 100,000 people every year.

Meanwhile, it is known that the number of microorganisms symbiotically living in the human body is 100 trillion which is 10 times the number of human cells, and the number of genes of microorganisms exceeds 100 times the number of human genes. A microbiota is a microbial community that includes bacteria, archaea, and eukaryotes present in a given habitat. The intestinal microbiota is known to play a vital role in human's physiological phenomena and significantly affect human health and diseases through interactions with human cells. Bacteria coexisting in human bodies secrete nanometer-sized vesicles to exchange information about genes, proteins, and the like with other cells. The mucous membranes form a physical barrier membrane that does not allow particles with the size of 200 nm or more to pass therethrough, and thus bacteria symbiotically living in the mucous membranes are unable to pass therethrough, but bacteria-derived extracellular vesicles have a size of approximately 100 nm or less and thus relatively freely pass through the mucous membranes and are absorbed into the human body.

Metagenomics, also called environmental genomics, may be analytics for metagenomic data obtained from samples collected from the environment (Korean Patent Publication No. 2011-0073049). Recently, the bacterial composition of human microbiota has been listed using a method based on 16s ribosomal RNA (16s rRNA) base sequences, and 16s rDNA base sequences, which are genes of 16s ribosomal RNA, are analyzed using a next generation sequencing (NGS) platform. However, in terms of inflammatory bowel disease occurrence, a method of diagnosing inflammatory bowel disease by isolating bacteria and bacteria-derived vesicles from a human body-derived substance such as stool and identifying causative factors of colon polyps and inflammatory bowel disease through analysis of a metagenome present in the bacteria-derived vesicles has not been reported yet.

DISCLOSURE

Technical Problem

The inventors extracted a gene from bacteria and bacteria-derived vesicles using stool, which is a subject-derived sample and conducted metagenomic analysis on the gene in order to diagnose inflammatory bowel disease (IBD) including ulcerative colitis and Crohn's disease, thereby identifying that bacteria and bacteria-derived vesicles that are able to act as causative factors of inflammatory bowel disease, such as ulcerative colitis and Crohn's disease. Based on this, the present invention was completed.

Therefore, the present invention is directed to providing a method of providing information for diagnosing inflammatory bowel disease through metagenomic analysis on a gene present in bacteria or bacteria-derived vesicles, an inflammatory bowel disease diagnosing method, and a method of predicting the risk of inflammatory bowel disease occurrence.

However, the technical goals of the present invention are not limited to the aforementioned goals, and other unmentioned technical goals will be clearly understood by those of ordinary skill in the art from the following description.

Technical Solution

To achieve the above-described object of the present invention, the present invention provides a method of providing information for diagnosing ulcerative colitis, comprising the following processes:
(a) extracting DNAs from bacteria isolated from a normal individual and a subject sample;
(b) performing polymerase chain reaction (PCR) on the extracted DNA using a pair of primers comprising SEQ ID NO: 1 and SEQ ID NO: 2; and
(c) comparing the increase or decrease in content of bacteria of the subject-derived sample with that of a normal individual-derived sample through sequencing of the PCR product.

The present invention also provides a method of diagnosing ulcerative colitis, comprising the following processes:
(a) extracting DNAs from bacteria isolated from a normal individual and a subject sample;
(b) performing polymerase chain reaction (PCR) on the extracted DNA using a pair of primers comprising SEQ ID NO: 1 and SEQ ID NO: 2; and
(c) comparing the increase or decrease in content of bacteria of the subject-derived sample with that of a normal individual-derived sample through sequencing of the PCR product.

The present invention also provides a method of predicting a risk for ulcerative colitis, comprising the following processes:
(a) extracting DNAs from bacteria isolated from a normal individual and a subject sample;
(b) performing polymerase chain reaction (PCR) on the extracted DNA using a pair of primers comprising SEQ ID NO: 1 and SEQ ID NO: 2; and
(c) comparing the increase or decrease in content of bacteria of the subject-derived sample with that of a normal individual-derived sample through sequencing of the PCR product.

In one embodiment of the present invention, in process (c), ulcerative colitis may be diagnosed by comparing an increase or decrease in content of one or more bacteria selected from the group consisting of the phylum Tenericutes, the phylum Cyanobacteria, and the phylum Proteobacteria in stool.

In another embodiment of the present invention, in process (c), ulcerative colitis may be diagnosed by comparing an increase or decrease in content of one or more bacteria selected from the group consisting of the class Alphaproteobacteria, the class Betaproteobacteria, the class Mollicutes, the class Gammaproteobacteria, and the class Coriobacteria in stool.

In another embodiment of the present invention, in process (c), ulcerative colitis may be diagnosed by comparing an increase or decrease in content of one or more bacteria selected from the group consisting of the order Rhizobiales, the order Sphingomonadales, the order Burkholderiales, the order Bacillales, the order Pseudomonadales, the order RF39, the order Enterobacteriales, the order Bifidobacteriales, and the order Coriobacteriales in stool.

In another embodiment of the present invention, in process (c), ulcerative colitis may be diagnosed by comparing an increase or decrease in content of one or more bacteria selected from the group consisting of the family Oxalobacteraceae, the family Propionibacteriaceae, the family Moraxellaceae, the family Staphylococcaceae, the family Sphingomonadaceae, the family Corynebacteriaceae, the family Micrococcaceae, the family Pseudomonadaceae, the family S24-7, the family Prevotellaceae, the family Enterobacteriaceae, the family Mogibacteriaceae, the family Bifidobacteriaceae, the family Lachnospiraceae, the family Coriobacteriaceae, and the family Actinomycetaceae in stool.

In another embodiment of the present invention, in process (c), ulcerative colitis may be diagnosed by comparing an increase or decrease in content of one or more bacteria selected from the group consisting of the genus *Cupriavidus*, the genus *Enhydrobacter*, the genus *Propionibacterium*, the genus *Acinetobacter*, the genus *Staphylococcus*, the genus *Sphingomonas*, the genus *Corynebacterium*, the genus *Citrobacter*, the genus *Rothia*, the genus *Prevotella*, the genus SMB53, the genus *Bifidobacterium*, the genus *Actinomyces*, the genus *Oscillospira*, the genus *Collinsella*, the genus *Veillonella*, the genus *Dorea*, the genus *Eggerthella*, and the genus *Ruminococcus* in stool.

In one embodiment of the present invention, the normal individual and subject samples are stool, and
process (c) may comprise comparing an increase or decrease in content of one or more bacteria selected from the group consisting of the phylum Tenericutes, the phylum Cyanobacteria, and the phylum Proteobacteria;
one or more bacteria selected from the group consisting of the class Alphaproteobacteria, the class Betaproteobacteria, the class Mollicutes, the class Gammaproteobacteria, and the class Coriobacteriia;
one or more bacteria selected from the group consisting of the order Rhizobiales, the order Sphingomonadales, the order Burkholderiales, the order Bacillales, the order Pseudomonadales, the order RF39, the order Enterobacteriales, the order Bifidobacteriales, and the order Coriobacteriales;
one or more bacteria selected from the group consisting of the family Oxalobacteraceae, the family Propionibacteriaceae, the family Moraxellaceae, the family Staphylococcaceae, the family Sphingomonadaceae, the family Corynebacteriaceae, the family Micrococcaceae, the family Pseudomonadaceae, the family S24-7, the family Prevotellaceae, the family Enterobacteriaceae, the family Mogibacteriaceae, the family Bifidobacteriaceae, the family Lachnospiraceae, the family Coriobacteriaceae, and the family Actinomycetaceae; or
one or more bacteria selected from the group consisting of the genus *Cupriavidus*, the genus *Enhydrobacter*, the genus *Propionibacterium*, the genus *Acinetobacter*, the genus *Staphylococcus*, the genus *Sphingomonas*, the genus *Corynebacterium*, the genus *Citrobacter*, the genus *Rothia*, the genus *Prevotella*, the genus SMB53, the genus *Bifidobacterium*, the genus *Actinomyces*, the genus *Oscillospira*, the genus *Collinsella*, the genus *Veillonella*, the genus *Dorea*, the genus *Eggerthella*, and the genus *Ruminococcus*.

In another embodiment of the present invention, in process (c), in comparison with the normal individual-derived sample, it is possible to diagnose an increase in the content of the following as ulcerative colitis:
bacteria of the class Coriobacteriia,
one or more bacteria selected from the group consisting of the order Coriobacteriales, and the order Bifidobacteriales,
one or more bacteria selected from the group consisting of the family Bifidobacteriaceae, the family Lachnospiraceae, the family Coriobacteriaceae, and the family Actinomycetaceae, or
one or more bacteria selected from the group consisting of the genus *Bifidobacterium*, the genus *Actinomyces*, the genus *Oscillospira*, the genus *Collinsella*, the genus *Veillonella*, the genus *Dorea*, the genus *Eggerthella*, and the genus *Ruminococcus*.

In another embodiment of the present invention, in process (c), in comparison with the normal individual-derived sample, it is possible to diagnose a decrease in the content of the following as ulcerative colitis:
one or more bacteria selected from the group consisting of the phylum Tenericutes, the phylum Cyanobacteria, and the phylum Proteobacteria,
one or more bacteria selected from the group consisting of the class Alphaproteobacteria, the class Betaproteobacteria, the class Mollicutes, and the class Gammaproteobacteria, one or more bacteria selected from the group consisting of the order Rhizobiales, the order Sphingomonadales, the order Burkholderiales, the order Bacillales, the order Pseudomonadales, the order RF39, and the order Enterobacteriales, one or more bacteria selected from the group consisting of the family Oxalobacteraceae, the family Propionibacteriaceae, the family Moraxellaceae, the family Staphylococcaceae, the family Sphingomonadaceae, the family Corynebacteriaceae, the family Micrococcaceae, the family Pseudomonadaceae, the family S24-7, the family Prevotellaceae, the family Enterobacteriaceae, and the family Mogibacteriaceae, or one or more bacteria selected from the group consisting of the genus *Cupriavidus*, the genus *Enhydrobacter*, the genus *Propionibacterium*, the genus *Acinetobacter*, the genus *Staphylococcus*, the genus *Sphingomonas*, the genus *Corynebacterium*, the genus *Citrobacter*, the genus *Rothia*, the genus *Prevotella*, and the genus SMB53.

To achieve the above-described object of the present invention, the present invention provides a method of providing information for diagnosing ulcerative colitis, comprising the following processes:
(a) extracting DNAs from vesicles isolated from a normal individual and a subject sample;
(b) performing polymerase chain reaction (PCR) on the extracted DNA using a pair of primers comprising SEQ ID NO: 1 and SEQ ID NO: 2; and
(c) comparing the increase or decrease in content of vesicles of the subject-derived sample with that of a normal individual-derived sample through sequencing of the PCR product.

The present invention also provides a method of diagnosing ulcerative colitis, comprising the following processes:
(a) extracting DNAs from vesicles isolated from a normal individual and a subject sample;
(b) performing polymerase chain reaction (PCR) on the extracted DNA using a pair of primers comprising SEQ ID NO: 1 and SEQ ID NO: 2; and
(c) comparing the increase or decrease in content of vesicles of the subject-derived sample with that of a normal individual-derived sample through sequencing of the PCR product.

The present invention also provides a method of predicting a risk for ulcerative colitis, comprising the following processes:
(a) extracting DNAs from vesicles isolated from a normal individual and a subject sample;
(b) performing polymerase chain reaction (PCR) on the extracted DNA using a pair of primers comprising SEQ ID NO: 1 and SEQ ID NO: 2; and
(c) comparing the increase or decrease in content of vesicles of the subject-derived sample with that of a normal individual-derived sample through sequencing of the PCR product.

In one embodiment of the present invention, in process (c), ulcerative colitis may be diagnosed by comparing an increase or decrease in content of vesicles derived from one or more bacteria selected from the group consisting of the phylum Tenericutes, the phylum Cyanobacteria, the phylum Fusobacteria, the phylum Proteobacteria, and the phylum Armatimonadetes in stool.

In one embodiment of the present invention, in process (c), ulcerative colitis may be diagnosed by comparing an increase or decrease in content of vesicles derived from one or more bacteria selected from the group consisting of the class Sphingobacteriia, the class Mollicutes, the class Betaproteobacteria, the class Chloroplast, the class Alphaproteobacteria, the class Flavobacteriia, the class Fusobacteriia, the class Erysipelotrichi, and the class Coriobacteriia in stool.

In one embodiment of the present invention, in process (c), ulcerative colitis may be diagnosed by comparing an increase or decrease in content of vesicles derived from one or more bacteria selected from the group consisting of the order Rhodobacterales, the order Sphingobacteriales, the order Rhizobiales, the order Burkholderiales, the order Oceanospirillales, the order Neisseriales, the order Rhodospirillales, the order Streptophyta, the order Pseudomonadales, the order Bacillales, the order Flavobacteriales, the order Actinomycetales, the order Fusobacteriales, the order Xanthomonadales, the order Erysipelotrichales, the order Coriobacteriales, and the order Bifidobacteriales in stool.

In one embodiment of the present invention, in process (c), ulcerative colitis may be diagnosed by comparing an increase or decrease in content of vesicles derived from one or more bacteria selected from the group consisting of the family Oxalobacteraceae, the family Aerococcaceae, the family Rhizobiaceae, the family Rhodobacteraceae, the family Intrasporangiaceae, the family Sphingobacteriaceae, the family Methylobacteriaceae, the family Nocardioidaceae, the family Pseudomonadaceae, the family Bacillaceae, the family Neisseriaceae, the family Acetobacteraceae, the family Micrococcaceae, the family S24-7, the family Halomonadaceae, the family Planococcaceae, the family Peptococcaceae, the family Comamonadaceae, the family Rikenellaceae, the family Moraxellaceae, the family Propionibacteriaceae, the family Staphylococcaceae, the family Weeksellaceae, the family Paraprevotellaceae, the family Corynebacteriaceae, the family Fusobacteriaceae, the family Nocardiaceae, the family Streptococcaceae, the family Lachnospiraceae, the family Fimbriimonadaceae, the family Xanthomonadaceae, the family Erysipelotrichaceae, the family Coriobacteriaceae, and the family Bifidobacteriaceae in stool.

In one embodiment of the present invention, in process (c), ulcerative colitis may be diagnosed by comparing an increase or decrease in content of vesicles derived from one or more bacteria selected from the group consisting of the genus *Cupriavidus*, the genus *Paracoccus*, the genus *Methylobacterium*, the genus *Citrobacter*, the genus *Halomonas*, the genus *Bacillus*, the genus *Pseudomonas*, the genus *Micrococcus*, the genus *Enhydrobacter*, the genus *Proteus*, the genus *Neisseria*, the genus *Rothia*, the genus *Propionibacterium*, the genus *Staphylococcus*, the genus *Acinetobacter*, the genus *Corynebacterium*, the genus *Fusobacterium*, the genus *Streptococcus*, the genus *Rhodococcus*, the genus *Klebsiella*, the genus *Blautia*, the genus *Peptoniphilus*, the genus *Bifidobacterium*, the genus *Coprococcus*, the genus *Eubacterium*, the genus *Dorea*, the genus *Collinsella*, and the genus *Stenotrophomonas* in stool.

In one embodiment of the present invention, the normal individual and subject samples are stool, and
process (c) may comprise comparing an increase or decrease in content of vesicles derived from one or more bacteria selected from the group consisting of the phylum Tenericutes, the phylum Cyanobacteria, the phylum Fusobacteria, the phylum Proteobacteria, and the phylum Armatimonadetes;
vesicles derived from one or more bacteria selected from the group consisting of the class Sphingobacteriia, the class Mollicules, the class Betaproteobacteria, the class Chloroplast, the class Alphaproteobacteria, the class Flavobacteriia, the class Fusobacteriia, the class Erysipelotrichi, and the class Coriobacteriia;

vesicles derived from one or more bacteria selected from the group consisting of the order Rhodobacterales, the order Sphingobacteriales, the order Rhizobiales, the order Burkholderiales, the order Oceanospirillales, the order Neisseriales, the order Rhodospirillales, the order Streptophyta, the order Pseudomonadales, the order Bacillales, the order Flavobacteriales, the order Actinomycetales, the order Fusobacteriales, the order Xanthomonadales, the order Erysipelotrichales, the order Coriobacteriales, and the order Bifidobacteriales;

vesicles derived from one or more bacteria selected from the group consisting of the family Oxalobacteraceae, the family Aerococcaceae, the family Rhizobiaceae, the family Rhodobacteraceae, the family Intrasporangiaceae, the family Sphingobacteriaceae, the family Methylobacteriaceae, the family Nocardioidaceae, the family Pseudomonadaceae, the family Bacillaceae, the family Neisseriaceae, the family Acetobacteraceae, the family Micrococcaceae, the family S24-7, the family Halomonadaceae, the family Planococcaceae, the family Peptococcaceae, the family Comamonadaceae, the family Rikenellaceae, the family Moraxellaceae, the family Propionibacteriaceae, the family Staphylococcaceae, the family Weeksellaceae, the family Paraprevotellaceae, the family Corynebacteriaceae, the family Fusobacteriaceae, the family Nocardiaceae, the family Streptococcaceae, the family Lachnospiraceae, the family Fimbriimonadaceae, the family Xanthomonadaceae, the family Erysipelotrichaceae, the family Coriobacteriaceae, and the family Bifidobacteriaceae; or vesicles derived from one or more bacteria selected from the group consisting of the genus *Cupriavidus*, the genus *Paracoccus*, the genus *Methylobacterium*, the genus *Citrobacter*, the genus *Halomonas*, the genus *Bacillus*, the genus *Pseudomonas*, the genus *Micrococcus*, the genus *Enhydrobacter*, the genus *Proteus*, the genus *Neisseria*, the genus *Rothia*, the genus *Propionibacterium*, the genus *Staphylococcus*, the genus *Acinetobacter*, the genus *Corynebacterium*, the genus *Fusobacterium*, the genus *Streptococcus*, the genus *Rhodococcus*, the genus *Klebsiella*, the genus *Blautia*, the genus *Peptoniphilus*, the genus *Bifidobacterium*, the genus *Coprococcus*, the genus *Eubacterium*, the genus *Dorea*, the genus *Collinsella*, and the genus *Stenotrophomonas*.

In another embodiment of the present invention, in process (c), in comparison with the normal individual-derived sample, it is possible to diagnose an increase in the content of the following as ulcerative colitis:

vesicles derived from bacteria of the phylum Armatimonadetes, vesicles derived from one or more bacteria selected from the group consisting of the class Erysipelotrichi, and the class Coriobacteriia, vesicles derived from one or more bacteria selected from the group consisting of the order Erysipelotrichales, the order Coriobacteriales, the order Xanthomonadales, and the order Bifidobacteriales, vesicles derived from one or more bacteria selected from the group consisting of the family Nocardiaceae, the family Streptococcaceae, the family Lachnospiraceae, the family Fimbriimonadaceae, the family Xanthomonadaceae, the family Erysipelotrichaceae, the family Coriobacteriaceae, and the family Bifidobacteriaceae, or vesicles derived from one or more bacteria selected from the group consisting of the genus *Streptococcus*, the genus *Rhodococcus*, the genus *Klebsiella*, the genus *Blautia*, the genus *Peptoniphilus*, the genus *Bifidobacterium*, the genus *Coprococcus*, the genus *Eubacterium*, the genus *Dorea*, the genus *Collinsella*, and the genus *Stenotrophomonas*.

In another embodiment of the present invention, in process (c), in comparison with the normal individual-derived sample, it is possible to diagnose a decrease in the content of the following as ulcerative colitis:

vesicles derived from one or more bacteria selected from the group consisting of the phylum Tenericutes, the phylum Cyanobacteria, the phylum Fusobacteria, and the phylum Proteobacteria, vesicles derived from one or more bacteria selected from the group consisting of the class Sphingobacteriia, the class Mollicutes, the class Betaproteobacteria, the class Chloroplast, the class Alphaproteobacteria, the class Flavobacteriia, and the class Fusobacteriia, vesicles derived from one or more bacteria selected from the group consisting of the order Rhodobacterales, the order Sphingobacteriales, the order Rhizobiales, the order Burkholderiales, the order Oceanospirillales, the order Neisseriales, the order Rhodospirillales, the order Streptophyta, the order Pseudomonadales, the order Bacillales, the order Flavobacteriales, the order Actinomycetales, and the order Fusobacteriales, vesicles derived from one or more bacteria selected from the group consisting of the family Oxalobacteraceae, the family Aerococcaceae, the family Rhizobiaceae, the family Rhodobacteraceae, the family Intrasporangiaceae, the family Sphingobacteriaceae, the family Methylobacteriaceae, the family Nocardioidaceae, the family Pseudomonadaceae, the family Bacillaceae, the family Neisseriaceae, the family Acetobacteraceae, the family Micrococcaceae, the family S24-7, the family Halomonadaceae, the family Planococcaceae, the family Peptococcaceae, the family Comamonadaceae, the family Rikenellaceae, the family Moraxellaceae, the family Propionibacteriaceae, the family Staphylococcaceae, the family Weeksellaceae, the family Paraprevotellaceae, the family Corynebacteriaceae, and the family Fusobacteriaceae, or vesicles derived from one or more bacteria selected from the group consisting of the genus *Cupriavidus*, the genus *Paracoccus*, the genus *Methylobacterium*, the genus *Citrobacter*, the genus *Halomonas*, the genus *Bacillus*, the genus *Pseudomonas*, the genus *Micrococcus*, the genus *Enhydrobacter*, the genus *Proteus*, the genus *Neisseria*, the genus *Rothia*, the genus *Propionibacterium*, the genus *Staphylococcus*, the genus *Acinetobacter*, the genus *Corynebacterium*, and the genus *Fusobacterium*.

To achieve the above-described object of the present invention, the present invention provides a method of providing information for diagnosing Crohn's disease, comprising the following processes:

(a) extracting DNAs from bacteria isolated from a normal individual and a subject sample;

(b) performing polymerase chain reaction (PCR) on the extracted DNA using a pair of primers comprising SEQ ID NO: 1 and SEQ ID NO: 2; and (c) comparing the increase or decrease in content of bacteria of the subject-derived sample with that of a normal individual-derived sample through sequencing of the PCR product.

The present invention also provides a method of diagnosing Crohn's disease, comprising the following processes:
(a) extracting DNAs from bacteria isolated from a normal individual and a subject sample;
(b) performing polymerase chain reaction (PCR) on the extracted DNA using a pair of primers comprising SEQ ID NO: 1 and SEQ ID NO: 2; and
(c) comparing the increase or decrease in content of bacteria of the subject-derived sample with that of a normal individual-derived sample through sequencing of the PCR product.

The present invention also provides a method of predicting a risk for Crohn's disease, comprising the following processes:
(a) extracting DNAs from bacteria isolated from a normal individual and a subject sample;
(b) performing polymerase chain reaction (PCR) on the extracted DNA using a pair of primers comprising SEQ ID NO: 1 and SEQ ID NO: 2; and
(c) comparing the increase or decrease in content of bacteria of the subject-derived sample with that of a normal individual-derived sample through sequencing of the PCR product.

In one embodiment of the present invention, in process (c), Crohn's disease may be diagnosed by comparing an increase or decrease in content of one or more bacteria selected from the group consisting of the phylum Cyanobacteria, the phylum Tenericutes, the phylum Proteobacteria, and the phylum TM7 in stool.

In another embodiment of the present invention, in process (c), Crohn's disease may be diagnosed by comparing an increase or decrease in content of one or more bacteria selected from the group consisting of the class Alphaproteobacteria, the class Betaproteobacteria, the class Chloroplast, the class Mollicutes, and the class TM7-3 in stool.

In another embodiment of the present invention, in process (c), Crohn's disease may be diagnosed by comparing an increase or decrease in content of one or more bacteria selected from the group consisting of the order Pseudomonadales, the order Rhizobiales, the order Sphingomonadales, the order Burkholderiales, the order Bacillales, the order Streptophyta, the order RF39, the order Lactobacillales, the order Bifidobacteriales, and the order Gemellales in stool.

In another embodiment of the present invention, in process (c), Crohn's disease may be diagnosed by comparing an increase or decrease in content of one or more bacteria selected from the group consisting of the family Pseudomonadaceae, the family Oxalobacteraceae, the family Moraxellaceae, the family Propionibacteriaceae, the family Corynebacteriaceae, the family Sphingomonadaceae, the family Staphylococcaceae, the family Prevotellaceae, the family Micrococcaceae, the family S24-7, the family Leuconostocaceae, the family Bifidobacteriaceae, the family Lachnospiraceae, the family Actinomycetaceae, the family Gemellaceae, and the family Eubacteriaceae in stool.

In another embodiment of the present invention, in process (c), Crohn's disease may be diagnosed by comparing an increase or decrease in content of one or more bacteria selected from the group consisting of the genus *Cupriavidus*, the genus *Enhydrobacter*, the genus *Pseudomonas*, the genus *Acinetobacter*, the genus *Propionibacterium*, the genus *Corynebacterium*, the genus *Staphylococcus*, the genus *Sphingomonas*, the genus *Prevotella*, the genus *Lachnospira*, the genus *Rothia*, the genus *Paraprevotella*, the genus *Roseburia*, the genus *Faecalibacterium*, the genus *Bifidobacterium*, the genus *Blautia*, the genus *Actinomyces*, the genus *Klebsiella*, the genus *Eggerthella*, the genus *Ruminococcus*, and the genus *Dorea* in stool.

In one embodiment of the present invention, the normal individual and subject samples are stool, and
process (c) may comprise comparing an increase or decrease in content of one or more bacteria selected from the group consisting of the phylum Cyanobacteria, the phylum Tenericutes, the phylum Proteobacteria, and the phylum TM7;
one or more bacteria selected from the group consisting of the class Alphaproteobacteria, the class Betaproteobacteria, the class Chloroplast, the class Mollicutes, and the class TM7-3;
one or more bacteria selected from the group consisting of the order Pseudomonadales, the order Rhizobiales, the order Sphingomonadales, the order Burkholderiales, the order Bacillales, the order Streptophyta, the order RF39, the order Lactobacillales, the order Bifidobacteriales, and the order Gemellales;
one or more bacteria selected from the group consisting of the family Pseudomonadaceae, the family Oxalobacteraceae, the family Moraxellaceae, the family Propionibacteriaceae, the family Corynebacteriaceae, the family Sphingomonadaceae, the family Staphylococcaceae, the family Prevotellaceae, the family Micrococcaceae, the family S24-7, the family Leuconostocaceae, the family Bifidobacteriaceae, the family Lachnospiraceae, the family Actinomycetaceae, the family Gemellaceae, and the family Eubacteriaceae; or
one or more bacteria selected from the group consisting of the genus *Cupriavidus*, the genus *Enhydrobacter*, the genus *Pseudomonas*, the genus *Acinetobacter*, the genus *Propionibacterium*, the genus *Corynebacterium*, the genus *Staphylococcus*, the genus *Sphingomonas*, the genus *Prevotella*, the genus *Lachnospira*, the genus *Rothia*, the genus *Paraprevotella*, the genus *Roseburia*, the genus *Faecalibacterium*, the genus *Bifidobacterium*, the genus *Blautia*, the genus *Actinomyces*, the genus *Klebsiella*, the genus *Eggerthella*, the genus *Ruminococcus*, and the genus *Dorea*.

In another embodiment of the present invention, in process (c), in comparison with the normal individual-derived sample, it is possible to diagnose an increase in the content of the following as Crohn's disease:
bacteria of the phylum TM7,
bacteria of the class TM7-3,
one or more bacteria selected from the group consisting of the order Lactobacillales, the order Bifidobacteriales, and the order Gemellales,
one or more bacteria selected from the group consisting of the family Bifidobacteriaceae, the family Lachnospiraceae, the family Actinomycetaceae, the family Gemellaceae, and the family Eubacteriaceae, or
one or more bacteria selected from the group consisting of the genus *Bifidobacterium*, the genus *Blautia*, the genus *Actinomyces*, the genus *Klebsiella*, the genus *Eggerthella*, the genus *Ruminococcus*, and the genus *Dorea*.

In another embodiment of the present invention, in process (c), in comparison with the normal individual-derived sample, it is possible to diagnose a decrease in the content of the following as Crohn's disease:

one or more bacteria selected from the group consisting of the phylum Cyanobacteria, the phylum Tenericutes, and the phylum Proteobacteria, one or more bacteria selected from the group consisting of the class Alphaproteobacteria, the class Betaproteobacteria, the class Chloroplast, and the class Mollicutes, one or more bacteria selected from the group consisting of the order Pseudomonadales, the order Rhizobiales, the order Sphingomonadales, the order Burkholderiales, the order Bacillales, the order Streptophyta, and the order RF39, one or more bacteria selected from the group consisting of the family Pseudomonadaceae, the family Oxalobacteraceae, the family Moraxellaceae, the family Propionibacteriaceae, the family Corynebacteriaceae, the family Sphingomonadaceae, the family Staphylococcaceae, the family Prevotellaceae, the family Micrococcaceae, the family S24-7, and the family Leuconostocaceae, or one or more bacteria selected from the group consisting of the genus *Cupriavidus*, the genus *Enhydrobacter*, the genus *Pseudomonas*, the genus *Acinetobacter*, the genus *Propionibacterium*, the genus *Corynebacterium*, the genus *Staphylococcus*, the genus *Sphingomonas*, the genus *Prevotella*, the genus *Lachnospira*, the genus *Rothia*, the genus *Paraprevotella*, the genus *Roseburia*, and the genus *Faecalibacterium*.

To achieve the above-described object of the present invention, the present invention provides a method of providing information for diagnosing Crohn's disease, comprising the following processes:

(a) extracting DNAs from vesicles isolated from a normal individual and a subject sample;
(b) performing polymerase chain reaction (PCR) on the extracted DNA using a pair of primers comprising SEQ ID NO: 1 and SEQ ID NO: 2; and
(c) comparing the increase or decrease in content of vesicles of the subject-derived sample with that of a normal individual-derived sample through sequencing of the PCR product.

The present invention also provides a method of diagnosing Crohn's disease, comprising the following processes:

(a) extracting DNAs from vesicles isolated from a normal individual and a subject sample;
(b) performing polymerase chain reaction (PCR) on the extracted DNA using a pair of primers comprising SEQ ID NO: 1 and SEQ ID NO: 2; and
(c) comparing the increase or decrease in content of vesicles of the subject-derived sample with that of a normal individual-derived sample through sequencing of the PCR product.

The present invention also provides a method of predicting a risk for Crohn's disease, comprising the following processes:

(a) extracting DNAs from vesicles isolated from a normal individual and a subject sample;
(b) performing polymerase chain reaction (PCR) on the extracted DNA using a pair of primers comprising SEQ ID NO: 1 and SEQ ID NO: 2; and
(c) comparing the increase or decrease in content of vesicles of the subject-derived sample with that of a normal individual-derived sample through sequencing of the PCR product.

In one embodiment of the present invention, in process (c), Crohn's disease may be diagnosed by comparing an increase or decrease in content of vesicles derived from one or more bacteria selected from the group consisting of the phylum Tenericutes, the phylum Cyanobacteria, the phylum Fusobacteria, the phylum Proteobacteria, and the phylum Actinobacteria in stool.

In one embodiment of the present invention, in process (c), Crohn's disease may be diagnosed by comparing an increase or decrease in content of vesicles derived from one or more bacteria selected from the group consisting of the class Sphingobacteriia, the class Mollicutes, the class Chloroplast, the class Betaproteobacteria, the class Fusobacteria, the class Alphaproteobacteria, the class Flavobacteriia, the class Coriobacteriia, and the class Erysipelotrichi in stool.

In one embodiment of the present invention, in process (c), Crohn's disease may be diagnosed by comparing an increase or decrease in content of vesicles derived from one or more bacteria selected from the group consisting of the order Rhodobacterales, the order Sphingobacteriales, the order Neisseriales, the order Rhizobiales, the order Streptophyta, the order Burkholderiales, the order Oceanospirillales, the order Fusobacteriales, the order Pseudomonadales, the order Flavobacteriales, the order Xanthomonadales, the order Coriobacteriales, the order Bifidobacteriales, and the order Erysipelotrichales in stool.

In one embodiment of the present invention, in process (c), Crohn's disease may be diagnosed by comparing an increase or decrease in content of vesicles derived from one or more bacteria selected from the group consisting of the family Intrasporangiaceae, the family Oxalobacteraceae, the family Rhizobiaceae, the family Nocardioidaceae, the family Rhodobacteraceae, the family Sphingobacteriaceae, the family Aerococcaceae, the family Leptotrichiaceae, the family Methylobacteriaceae, the family Neisseriaceae, the family Porphyromonadaceae, the family Planococcaceae, the family Bacillaceae, the family Pseudomonadaceae, the family Micrococcaceae, the family Fusobacteriaceae, the family Peptococcaceae, the family Prevotellaceae, the family Propionibacteriaceae, the family Corynebacteriaceae, the family Lachnospiraceae, the family Nocardiaceae, the family Xanthomonadaceae, the family Coriobacteriaceae, the family Bifidobacteriaceae, and the family Erysipelotrichaceae in stool.

In one embodiment of the present invention, in process (c), Crohn's disease may be diagnosed by comparing an increase or decrease in content of vesicles derived from one or more bacteria selected from the group consisting of the genus *Cupriavidus*, the genus *Citrobacter*, the genus *Methylobacterium*, the genus *Paracoccus*, the genus *Proteus*, the genus *Enhydrobacter*, the genus *Halomonas*, the genus *Neisseria*, the genus *Parabacteroides*, the genus *Rothia*, the genus *Pseudomonas*, the genus *Bacillus*, the genus *Fusobacterium*, the genus *Lactococcus*, the genus *Roseburia*, the genus *Prevotella*, the genus *Propionibacterium*, the genus *Corynebacterium*, the genus *Oscillospira*, the genus *Klebsiella*, the genus *Eggerthella*, the genus *Rhodococcus*, the genus *Blautia*, the genus *Bifidobacterium*, the genus *Coprococcus*, the genus *Eubacterium*, the genus *Collinsella*, the genus *Ruminococcus*, and the genus *Stenotrophomonas* in stool.

In one embodiment of the present invention, the normal individual and subject samples are stool, and process (c) may comprise comparing an increase or decrease in content of vesicles derived from one or more bacteria selected from the group consisting of the phylum Tenericutes, the phylum Cyanobacteria, the phylum Fusobacteria, the phylum Proteobacteria, and the phylum Actinobacteria;

vesicles derived from one or more bacteria selected from the group consisting of the class Sphingobacteriia, the class Mollicutes, the class Chloroplast, the class Betaproteobacteria, the class Fusobacteriia, the class Alphaproteobacteria, the class Flavobacteriia, the class Coriobacteriia, and the class Erysipelotrichi;

vesicles derived from one or more bacteria selected from the group consisting of the order Rhodobacterales, the order Sphingobacteriales, the order Neisseriales, the order Rhizobiales, the order Streptophyta, the order Burkholderiales, the order Oceanospirillales, the order Fusobacteriales, the order Pseudomonadales, the order Flavobacteriales, the order Xanthomonadales, the order Coriobacteriales, the order Bifidobacteriales, and the order Erysipelotrichales;

vesicles derived from one or more bacteria selected from the group consisting of the family Intrasporangiaceae, the family Oxalobacteraceae, the family Rhizobiaceae, the family Nocardioidaceae, the family Rhodobacteraceae, the family Sphingobacteriaceae, the family Aerococcaceae, the family Leptotrichiaceae, the family Methylobacteriaceae, the family Neisseriaceae, the family Porphyromonadaceae, the family Planococcaceae, the family Bacillaceae, the family Pseudomonadaceae, the family Micrococcaceae, the family Fusobacteriaceae, the family Peptococcaceae, the family Prevotellaceae, the family Propionibacteriaceae, the family Corynebacteriaceae, the family Lachnospiraceae, the family Nocardiaceae, the family Xanthomonadaceae, the family Coriobacteriaceae, the family Bifidobacteriaceae, and the family Erysipelotrichaceae; or vesicles derived from one or more bacteria selected from the group consisting of the genus *Cupriavidus*, the genus *Citrobacter*, the genus *Methylobacterium*, the genus *Paracoccus*, the genus *Proteus*, the genus *Enhydrobacter*, the genus *Halomonas*, the genus *Neisseria*, the genus *Parabacteroides*, the genus *Rothia*, the genus *Pseudomonas*, the genus *Bacillus*, the genus *Fusobacterium*, the genus *Lactococcus*, the genus *Roseburia*, the genus *Prevotella*, the genus *Propionibacterium*, the genus *Corynebacterium*, the genus *Oscillospira*, the genus *Klebsiella*, the genus *Eggerthella*, the genus *Rhodococcus*, the genus *Blautia*, the genus *Bifidobacterium*, the genus *Coprococcus*, the genus *Eubacterium*, the genus *Collinsella*, the genus *Ruminococcus*, and the genus *Stenotrophomonas*.

In another embodiment of the present invention, in process (c), in comparison with the normal individual-derived sample, it is possible to diagnose an increase in the content of the following as Crohn's disease:

vesicles derived from bacteria of the phylum Actinobacteria, vesicles derived from one or more bacteria selected from the group consisting of the class Coriobacteriia, and the class Erysipelotrichi, vesicles derived from one or more bacteria selected from the group consisting of the order Xanthomonadales, the order Coriobacteriales, the order Bifidobacteriales, and the order Erysipelotrichales, vesicles derived from one or more bacteria selected from the group consisting of the family Lachnospiraceae, the family Nocardiaceae, the family Xanthomonadaceae, the family Coriobacteriaceae, the family Bifidobacteriaceae, and the family Erysipelotrichaceae, or vesicles derived from one or more bacteria selected from the group consisting of the genus *Oscillospira*, the genus *Klebsiella*, the genus *Eggerthella*, the genus *Rhodococcus*, the genus *Blautia*, the genus *Bifidobacterium*, the genus *Coprococcus*, the genus *Eubacterium*, the genus *Collinsella*, the genus *Ruminococcus*, and the genus *Stenotrophomonas*.

In another embodiment of the present invention, in process (c), in comparison with the normal individual-derived sample, it is possible to diagnose a decrease in the content of the following as Crohn's disease:

vesicles derived from one or more bacteria selected from the group consisting of the phylum Tenericutes, the phylum Cyanobacteria, the phylum Fusobacteria, and the phylum Proteobacteria, vesicles derived from one or more bacteria selected from the group consisting of the class Sphingobacteriia, the class Mollicutes, the class Chloroplast, the class Betaproteobacteria, the class Fusobacteriia, the class Alphaproteobacteria, and the class Flavobactertiia, vesicles derived from one or more bacteria selected from the group consisting of the order Rhodobacterales, the order Sphingobacteriales, the order Neisseriales, the order Rhizobiales, the order Streptophyta, the order Burkholderiales, the order Oceanospirillales, the order Fusobacteriales, the order Pseudomonadales, and the order Flavobacteriales, vesicles derived from one or more bacteria selected from the group consisting of the family Intrasporangiaceae, the family Oxalobacteraceae, the family Rhizobiaceae, the family Nocardioidaceae, the family Rhodobacteraceae, the family Sphingobacteriaceae, the family Aerococcaceae, the family Leptotrichiaceae, the family Methylobacteriaceae, the family Neisseriaceae, the family Porphyromonadaceae, the family Planococcaceae, the family Bacillaceae, the family Pseudomonadaceae, the family Micrococcaceae, the family Fusobacteriaceae, the family Peptococcaceae, the family Prevotellaceae, the family Propionibacteriaceae, and the family Corynebacteriaceae, or vesicles derived from one or more bacteria selected from the group consisting of the genus *Cupriavidus*, the genus *Citrobacter*, the genus *Methylobacterium*, the genus *Paracoccus*, the genus *Proteus*, the genus *Enhydrobacter*, the genus *Halomonas*, the genus *Neisseria*, the genus *Parabacteroides*, the genus *Rothia*, the genus *Pseudomonas*, the genus *Bacillus*, the genus *Fusobacterium*, the genus *Lactococcus*, the genus *Roseburia*, the genus *Prevotella*, the genus *Propionibacterium*, and the genus *Corynebacterium*.

To achieve the above-described object of the present invention, the present invention provides a method of providing information for differential diagnosis of ulcerative colitis and Crohn's disease, comprising the following processes:

(a) extracting DNAs from bacteria isolated from a subject sample;

(b) performing polymerase chain reaction (PCR) on the extracted DNA using a pair of primers comprising SEQ ID NO: 1 and SEQ ID NO: 2; and (c) comparing the increase or decrease in content of bacteria of the subject-derived sample with that of ulcerative colitis patient-derived sample through sequencing of the PCR product.

The present invention also provides a method of differential diagnosis of ulcerative colitis and Crohn's disease, comprising the following processes:

(a) extracting DNAs from bacteria isolated from a subject sample;

(b) performing polymerase chain reaction (PCR) on the extracted DNA using a pair of primers comprising SEQ ID NO: 1 and SEQ ID NO: 2; and (c) comparing the increase or decrease in content of bacteria of the subject-derived sample with that of ulcerative colitis patient-derived sample through sequencing of the PCR product.

The present invention also provides a method of predicting a risk for ulcerative colitis and Crohn's disease, comprising the following processes:

(a) extracting DNAs from bacteria isolated from a subject sample;

(b) performing polymerase chain reaction (PCR) on the extracted DNA using a pair of primers comprising SEQ ID NO: 1 and SEQ ID NO: 2; and (c) comparing the increase or decrease in content of bacteria of the subject-derived sample with that of ulcerative colitis patient-derived sample through sequencing of the PCR product.

In one embodiment of the present invention, in process (c), ulcerative colitis and Crohn's disease may be subjected to differential diagnosis by comparing an increase or decrease in content of bacteria of the family Prevotellaceae in stool.

In another embodiment of the present invention, in process (c), ulcerative colitis and Crohn's disease may be subjected to differential diagnosis by comparing an increase or decrease in content of one or more bacteria selected from the group consisting of the genus *Prevotella*, the genus *Roseburia*, the genus *Faecalibacterium*, and the genus *Klebsiella* in stool.

In one embodiment of the present invention, the subject samples are stool, and process (c) may comprise comparing an increase or decrease in content of bacteria of the family Prevotellaceae; or one or more bacteria selected from the group consisting of the genus *Prevotella*, the genus *Roseburia*, the genus *Faecalibacterium*, and the genus *Klebsiella*.

In another embodiment of the present invention, in process (c), in comparison with the ulcerative colitis patient-derived sample, it is possible to differentially diagnose an increase in the content of bacteria of the genus *Klebsiella* as Crohn's disease.

In another embodiment of the present invention, in process (c), in comparison with the ulcerative colitis patient-derived sample, it is possible to differentially diagnose a decrease in the content of the following as Crohn's disease:

bacteria of the family Prevotellaceae, or one or more bacteria selected from the group consisting of the genus *Prevotella*, the genus *Roseburia*, and the genus *Faecalibacterium*.

To achieve the above-described object of the present invention, the present invention provides a method of providing information for differential diagnosis of ulcerative colitis and Crohn's disease, comprising the following processes:

(a) extracting DNAs from vesicles isolated from a subject sample;

(b) performing polymerase chain reaction (PCR) on the extracted DNA using a pair of primers comprising SEQ ID NO: 1 and SEQ ID NO: 2; and (c) comparing the increase or decrease in content of vesicles of the subject-derived sample with that of ulcerative colitis patient-derived sample through sequencing of the PCR product.

The present invention also provides a method of differential diagnosis of ulcerative colitis and Crohn's disease, comprising the following processes:

(a) extracting DNAs from vesicles isolated from a subject sample;

(b) performing polymerase chain reaction (PCR) on the extracted DNA using a pair of primers comprising SEQ ID NO: 1 and SEQ ID NO: 2; and (c) comparing the increase or decrease in content of vesicles of the subject-derived sample with that of ulcerative colitis patient-derived sample through sequencing of the PCR product.

The present invention also provides a method of predicting a risk for ulcerative colitis and Crohn's disease, comprising the following processes:

(a) extracting DNAs from vesicles isolated from a subject sample;

(b) performing polymerase chain reaction (PCR) on the extracted DNA using a pair of primers comprising SEQ ID NO: 1 and SEQ ID NO: 2; and (c) comparing the increase or decrease in content of vesicles of the subject-derived sample with that of ulcerative colitis patient-derived sample through sequencing of the PCR product.

In one embodiment of the present invention, in process (c), ulcerative colitis and Crohn's disease may be subjected to differential diagnosis by comparing an increase or decrease in content of vesicles derived from bacteria of the family Prevotellaceae in stool.

In another embodiment of the present invention, in process (c), ulcerative colitis and Crohn's disease may be subjected to differential diagnosis by comparing an increase or decrease in content of vesicles derived from one or more bacteria selected from the group consisting of the genus *Prevotella*, and the genus *Eggerthella* in stool.

In one embodiment of the present invention, the subject samples are stool, and process (c) may comprise comparing an increase or decrease in content of vesicles derived from bacteria of the family Prevotellaceae; or vesicles derived from one or more bacteria selected from the group consisting of the genus *Prevotella*, and the genus *Eggerthella*.

In another embodiment of the present invention, in process (c), in comparison with the ulcerative colitis patient-derived sample, it is possible to differentially diagnose an increase in the content of vesicles derived from bacteria of the genus *Eggerthella* as Crohn's disease.

In another embodiment of the present invention, in process (c), in comparison with the ulcerative colitis patient-derived sample, it is possible to differentially diagnose a decrease in the content of the following as Crohn's disease:

vesicles derived from bacteria of the family Prevotellaceae, or vesicles derived from bacteria of the genus *Prevotella*.

Advantageous Effects

Vesicles released from bacteria present in the environment can be absorbed into the body to have directly influence on the occurrence of inflammation and cancer, and since inflammatory bowel disease is difficult to be early diagnosed before symptoms appear, effective treatment is difficult. Therefore, by previously predicting a causative factor of inflammatory bowel disease and the risk of the onset of the disease through metagenomic analysis of bacteria or bacteria-derived vesicles using a human body-derived sample according to the present invention, it is possible to predict and diagnose the inflammatory bowel disease risk group early, and the onset of the disease can be delayed or prevented with proper care. In addition, the vesicles can be used as a marker for differential diagnosis of ulcerative colitis and Crohn's disease through the above-mentioned analysis. Ultimately, according to the present invention, the incidence of inflammatory bowel disease can be lowered and the therapeutic effect can be increased by early diagnosis even after the onset of inflammatory bowel disease. In addition, a causative factor can be predicted for a patient diagnosed with inflammatory bowel disease through metagenomic analysis to avoid exposure to the causative factor, resulting in improvement in the progression of inflammatory bowel disease, or prevention of the recurrence thereof.

DESCRIPTION OF DRAWINGS

FIGS. 1A and 1B are provided to evaluate the distribution pattern of bacteria-derived vesicles in the body, in which FIG. 1A is a set of images showing the distribution patterns of intestinal bacteria and bacteria-derived vesicles (EV) in mice after oral administration over time (0, 5 min, 3 h, 6 h and 12 h), and FIG. 1B is a set of images showing distribution patterns of the bacteria and vesicles by orally administering intestinal bacteria and bacteria-derived vesicles (EV) to mice, and extracting urine and various organs (heart, lung, liver, kidney, spleen, adipose tissue and muscle) 12 hours after administration.

[Best Model]

Figure 1A:
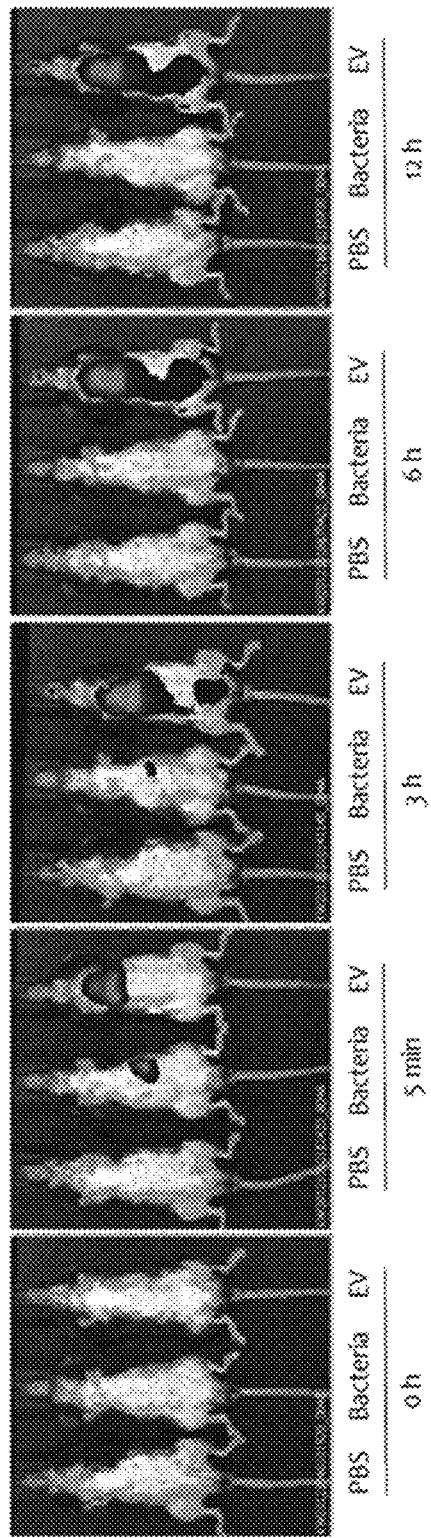

The present invention relates to a method of diagnosing inflammatory bowel disease through bacterial metagenomic analysis. The inventors of the present invention extracted genes from bacteria and bacteria-derived vesicles using a subject-derived sample, performed metagenomic analysis thereon, and identified bacteria and bacteria-derived vesicles capable of acting as a causative factor of inflammatory bowel disease such as ulcerative colitis and Crohn's disease.

Therefore, the present invention provides a method of providing information for diagnosing ulcerative colitis, which comprises:
(a) extracting DNAs from bacteria or bacteria-derived vesicles isolated from a normal individual and a subject sample;
(b) performing polymerase chain reaction (PCR) on the extracted DNA using a pair of primers comprising SEQ ID NO: 1 and SEQ ID NO: 2; and
(c) comparing the increase or decrease in content of bacteria or bacteria-derived vesicles of the subject-derived sample with that of a normal individual-derived sample through sequencing of the PCR product.

In addition, the present invention provides a method of providing information for diagnosing Crohn's disease, which comprises:
(a) extracting DNAs from bacteria or bacteria-derived vesicles isolated from a normal individual and a subject sample;
(b) performing polymerase chain reaction (PCR) on the extracted DNA using a pair of primers comprising SEQ ID NO: 1 and SEQ ID NO: 2; and
(c) comparing the increase or decrease in content of bacteria or bacteria-derived vesicles of the subject-derived sample with that of a normal individual-derived sample through sequencing of the PCR product.

In addition, the present invention provides a method of providing information for differential diagnosis of inflammatory bowel disease by comparing the increase or decrease in content of bacteria or bacteria-derived vesicles of the subject-derived sample with that of the ulcerative colitis patient-derived sample.

The inflammatory bowel disease may be ulcerative colitis and Crohn's disease.

Therefore, the present invention provides a method of providing information for differential diagnosis of ulcerative colitis and Crohn's disease, which comprises:
(a) extracting DNAs from bacteria or bacteria-derived vesicles isolated from a subject sample;
(b) performing polymerase chain reaction (PCR) on the extracted DNA using a pair of primers comprising SEQ ID NO: 1 and SEQ ID NO: 2; and
(c) comparing the increase or decrease in content of bacteria or bacteria-derived vesicles of the subject-derived sample with that of ulcerative colitis patient-derived sample through sequencing of the PCR product.

The term "inflammatory bowel disease diagnosis" as used herein refers to determining whether a patient has a risk for inflammatory bowel disease, whether the risk for inflammatory bowel disease is relatively high, or whether inflammatory bowel disease has already occurred. The method of the present invention may be used to delay the onset of inflammatory bowel disease through special and appropriate care for a specific patient, which is a patient having a high risk for inflammatory bowel disease or prevent the onset of inflammatory bowel disease. In addition, the method may be clinically used to determine treatment by selecting the most appropriate treatment method through early diagnosis of inflammatory bowel disease. In the present invention, inflammatory bowel disease is preferably, ulcerative colitis and Crohn's disease, but the present invention is not limited thereto.

The term "metagenome" as used herein refers to the total of genomes including all viruses, bacteria, fungi, and the like in isolated regions such as soil, the intestines of animals, and the like, and is mainly used as a concept of genomes that explains identification of many microorganisms at once using a sequencer to analyze non-cultured microorganisms. In particular, a metagenome does not refer to a genome of one species, but refers to a mixture of genomes, including genomes of all species of an environmental unit. This term originates from the view that, when defining one species in a process in which biology is advanced into omics, various species as well as existing one species functionally interact with each other to form a complete species. Technically, it is the subject of techniques that analyzes all DNAs and RNAs regardless of species using rapid sequencing to identify all species in one environment and verify interactions and metabolism. In the present invention, bacterial metagenomic analysis is performed using bacteria-derived extracellular vesicles isolated from, for example, serum.

In the present invention, the normal individual sample may be stool, but the present invention is not limited thereto.

In an embodiment of the present invention, metagenomic analysis was conducted on genes present in bacteria and bacteria-derived vesicles in stool samples of a normal individual, and patients with ulcerative colitis and Crohn's disease, and then the analysis results were analyzed at phylum, class, order, family and genus levels, thereby identifying bacteria and bacteria-derived vesicles, which can actually be a cause of the onset of ulcerative colitis and Crohn's disease.

Therefore, in an embodiment of the present invention, metagenomic analysis is performed on the bacteria, and bacteria capable of acting as a cause of the onset of ulcerative colitis were actually identified by analysis at phylum, class, order, family, and genus levels (see Example 4).

More particularly, in one embodiment of the present invention, as a result of performing bacterial metagenomic analysis on bacteria present in subject-derived stool samples at a phylum level, the content of bacteria belonging to the phylum Tenericutes, the phylum Cyanobacteria, and the phylum Proteobacteria was significantly different between ulcerative colitis patients and normal individuals.

In addition, in one embodiment of the present invention, as a result of performing bacterial metagenomic analysis on bacteria present in subject-derived stool samples at a class level, the content of bacteria belonging to the class Alphaproteobacteria, the class Betaproteobacteria, the class Mollicutes, the class Gammaproteobacteria, and the class Coriobacteria was significantly different between ulcerative colitis patients and normal individuals.

In addition, in one embodiment of the present invention, as a result of performing bacterial metagenomic analysis on bacteria present in subject-derived stool samples at an order level, the content of bacteria belonging to the order Rhizobiales, the order Sphingomonadales, the order Burkholderiales, the order Bacillales, the order Pseudomonadales, the order RF39, the order Enterobacteriales, the order Bifidobacteriales, and the order Coriobacteriales was significantly different between ulcerative colitis patients and normal individuals.

In addition, in one embodiment of the present invention, as a result of performing bacterial metagenomic analysis on bacteria present in subject-derived stool samples at a family level, the content of bacteria belonging to the family Oxalobacteraceae, the family Propionibacteriaceae, the family Moraxellaceae, the family Staphylococcaceae, the family Sphingomonadaceae, the family Corynebacteriaceae, the family Micrococcaceae, the family Pseudomonadaceae, the family S24-7, the family Prevotellaceae, the family Enterobacteriaceae, the family Mogibacteriaceae, the family Bifidobacteriaceae, the family Lachnospiraceae, the family Coriobacteriaceae, and the family Actinomycetaceae was significantly different between ulcerative colitis patients and normal individuals.

In addition, in one embodiment of the present invention, as a result of performing bacterial metagenomic analysis on bacteria present in subject-derived stool samples at a genus level, the content of bacteria belonging to the genus *Cupriavidus*, the genus *Enhydrobacter*, the genus *Propionibacterium*, the genus *Acinetobacter*, the genus *Staphylococcus*, the genus *Sphingomonas*, the genus *Corynebacterium*, the genus *Citrobacter*, the genus *Rothia*, the genus *Prevotella*, the genus SMB53, the genus *Bifidobacterium*, the genus *Actinomyces*, the genus *Oscillospira*, the genus *Collinsella*, the genus *Veillonella*, the genus *Dorea*, the genus *Eggerthella*, and the genus *Ruminococcus* was significantly different between ulcerative colitis patients and normal individuals.

In another embodiment of the present invention, metagenomic analysis is performed on the bacteria-derived vesicles, and bacteria-derived vesicles capable of acting as a cause of the onset of ulcerative colitis were actually identified by analysis at phylum, class, order, family, and genus levels (see Example 5).

More particularly, in one embodiment of the present invention, as a result of performing bacterial metagenomic analysis on vesicles present in subject-derived stool samples at a phylum level, the content of vesicles derived from bacteria belonging to the phylum Tenericutes, the phylum Cyanobacteria, the phylum Fusobacteria, the phylum Proteobacteria, and the phylum Armatimonadetes was significantly different between ulcerative colitis patients and normal individuals.

In addition, in one embodiment of the present invention, as a result of performing bacterial metagenomic analysis on vesicles present in subject-derived stool samples at a class level, the content of vesicles derived from bacteria belonging to the class Sphingobacteriia, the class Mollicutes, the class Betaproteobacteria, the class Chloroplast, the class Alphaproteobacteria, the class Flavobacteriia, the class Fusobacteriia, the class Erysipelotrichi, and the class Coriobacteriia was significantly different between ulcerative colitis patients and normal individuals.

In addition, in one embodiment of the present invention, as a result of performing bacterial metagenomic analysis on vesicles present in subject-derived stool samples at an order level, the content of vesicles derived from bacteria belonging to the order Rhodobacterales, the order Sphingobacteriales, the order Rhizobiales, the order Burkholderiales, the order Oceanospirillales, the order Neisseriales, the order Rhodospirillales, the order Streptophyta, the order Pseudomonadales, the order Bacillales, the order Flavobacteriales, the order Actinomycetales, the order Fusobacteriales, the order Xanthomonadales, the order Erysipelotrichales, the order Coriobacteriales, and the order Bifidobacteriales was significantly different between ulcerative colitis patients and normal individuals.

In addition, in one embodiment of the present invention, as a result of performing bacterial metagenomic analysis on vesicles present in subject-derived stool samples at a family level, the content of vesicles derived from bacteria belonging to the family Oxalobacteraceae, the family Aerococcaceae, the family Rhizobiaceae, the family Rhodobacteraceae, the family Intrasporangiaceae, the family Sphingobacteriaceae, the family Methylobacteriaceae, the family Nocardioidaceae, the family Pseudomonadaceae, the family Bacillaceae, the family Neisseriaceae, the family Acetobacteraceae, the family Micrococcaceae, the family S24-7, the family Halomonadaceae, the family Planococcaceae, the family Peptococcaceae, the family Comamonadaceae, the family Rikenellaceae, the family Moraxellaceae, the family Propionibacteriaceae, the family Staphylococcaceae, the family Weeksellaceae, the family Paraprevotellaceae, the family Corynebacteriaceae, the family Fusobacteriaceae, the family Nocardiaceae, the family Streptococcaceae, the family Lachnospiraceae, the family Fimbriimonadaceae, the family Xanthomonadaceae, the family Erysipelotrichaceae, the family Coriobacteriaceae, and the family Bifidobacteriaceae was significantly different between ulcerative colitis patients and normal individuals.

In addition, in one embodiment of the present invention, as a result of performing bacterial metagenomic analysis on vesicles present in subject-derived stool samples at a genus level, the content of vesicles derived from bacteria belonging to the genus *Cupriavidus*, the genus *Paracoccus*, the genus *Methylobacterium*, the genus *Citrobacter*, the genus *Halomonas*, the genus *Bacillus*, the genus *Pseudomonas*, the genus *Micrococcus*, the genus *Enhydrobacter*, the genus *Proteus*, the genus *Neisseria*, the genus *Rothia*, the genus *Propionibacterium*, the genus *Staphylococcus*, the genus *Acinetobacter*, the genus *Corynebacterium*, the genus *Fusobacterium*, the genus *Streptococcus*, the genus *Rhodococcus*, the genus *Klebsiella*, the genus *Blautia*, the genus *Peptoniphilus*, the genus *Bifidobacterium*, the genus *Coprococcus*, the genus *Eubacterium*, the genus *Dorea*, the genus

*Collinsella*, and the genus *Stenotrophomonas* was significantly different between ulcerative colitis patients and normal individuals.

In another embodiment of the present invention, metagenomic analysis is performed on the bacteria, and bacteria capable of acting as a cause of the onset of Crohn's disease were actually identified by analysis at phylum, class, order, family, and genus levels (see Example 6).

More particularly, in one embodiment of the present invention, as a result of performing bacterial metagenomic analysis on bacteria present in subject-derived stool samples at a phylum level, the content of bacteria belonging to the phylum Cyanobacteria, the phylum Tenericutes, the phylum Proteobacteria, and the phylum TM7 was significantly different between Crohn's disease patients and normal individuals.

In addition, in one embodiment of the present invention, as a result of performing bacterial metagenomic analysis on bacteria present in subject-derived stool samples at a class level, the content of bacteria belonging to the class Alphaproteobacteria, the class Betaproteobacteria, the class Chloroplast, the class Mollicutes, and the class TM7-3 was significantly different between Crohn's disease patients and normal individuals.

In addition, in one embodiment of the present invention, as a result of performing bacterial metagenomic analysis on bacteria present in subject-derived stool samples at an order level, the content of bacteria belonging to the order Pseudomonadales, the order Rhizobiales, the order Sphingomonadales, the order Burkholderiales, the order Bacillales, the order Streptophyta, the order RF39, the order Lactobacillales, the order Bifidobacteriales, and the order Gemellales was significantly different between Crohn's disease patients and normal individuals.

In addition, in one embodiment of the present invention, as a result of performing bacterial metagenomic analysis on bacteria present in subject-derived stool samples at a family level, the content of bacteria belonging to the family Pseudomonadaceae, the family Oxalobacteraceae, the family Moraxellaceae, the family Propionibacteriaceae, the family Corynebacteriaceae, the family Sphingomonadaceae, the family Staphylococcaceae, the family Prevotellaceae, the family Micrococcaceae, the family S24-7, the family Leuconostocaceae, the family Bifidobacteriaceae, the family Lachnospiraceae, the family Actinomycetaceae, the family Gemellaceae, and the family Eubacteriaceae was significantly different between Crohn's disease patients and normal individuals.

In addition, in one embodiment of the present invention, as a result of performing bacterial metagenomic analysis on bacteria present in subject-derived stool samples at a genus level, the content of bacteria belonging to the genus *Cupriavidus*, the genus *Enhydrobacter*, the genus *Pseudomonas*, the genus *Acinetobacter*, the genus *Propionibacterium*, the genus *Corynebacterium*, the genus *Staphylococcus*, the genus *Sphingomonas*, the genus *Prevotella*, the genus *Lachnospira*, the genus *Rothia*, the genus *Paraprevotella*, the genus *Roseburia*, the genus *Faecalibacterium*, the genus *Bifidobacterium*, the genus *Blautia*, the genus *Actinomyces*, the genus *Klebsiella*, the genus *Eggerthella*, the genus *Ruminococcus*, and the genus *Dorea* was significantly different between Crohn's disease patients and normal individuals.

In another embodiment of the present invention, metagenomic analysis is performed on the bacteria-derived vesicles, and bacteria-derived vesicles capable of acting as a cause of the onset of Crohn's disease were actually identified by analysis at phylum, class, order, family, and genus levels (see Example 7).

More particularly, in one embodiment of the present invention, as a result of performing bacterial metagenomic analysis on vesicles present in subject-derived stool samples at a phylum level, the content of vesicles derived from bacteria belonging to the phylum Tenericutes, the phylum Cyanobacteria, the phylum Fusobacteria, the phylum Proteobacteria, and the phylum Actinobacteria was significantly different between Crohn's disease patients and normal individuals.

In addition, in one embodiment of the present invention, as a result of performing bacterial metagenomic analysis on vesicles present in subject-derived stool samples at a class level, the content of vesicles derived from bacteria belonging to the class Sphingobacteriia, the class Mollicutes, the class Chloroplast, the class Betaproteobacteria, the class Fusobacteriia, the class Alphaproteobacteria, the class Flavobacteriia, the class Coriobacteriia, and the class Erysipelotrichi was significantly different between Crohn's disease patients and normal individuals.

In addition, in one embodiment of the present invention, as a result of performing bacterial metagenomic analysis on vesicles present in subject-derived stool samples at an order level, the content of vesicles derived from bacteria belonging to the order Rhodobacterales, the order Sphingobacteriales, the order Neisseriales, the order Rhizobiales, the order Streptophyta, the order Burkholderiales, the order Oceanospirillales, the order Fusobacteriales, the order Pseudomonadales, the order Flavobacteriales, the order Xanthomonadales, the order Coriobacteriales, the order Bifidobacteriales, and the order Erysipelotrichales was significantly different between Crohn's disease patients and normal individuals.

In addition, in one embodiment of the present invention, as a result of performing bacterial metagenomic analysis on vesicles present in subject-derived stool samples at a family level, the content of vesicles derived from bacteria belonging to the family Intrasporangiaceae, the family Oxalobacteraceae, the family Rhizobiaceae, the family Nocardioidaceae, the family Rhodobacteraceae, the family Sphingobacteriaceae, the family Aerococcaceae, the family Leptotrichiaceae, the family Methylobacteriaceae, the family Neisseriaceae, the family Porphyromonadaceae, the family Planococcaceae, the family Bacillaceae, the family Pseudomonadaceae, the family Micrococcaceae, the family Fusobacteriaceae, the family Peptococcaceae, the family Prevotellaceae, the family Propionibacteriaceae, the family Corynebacteriaceae, the family Lachnospiraceae, the family Nocardiaceae, the family Xanthomonadaceae, the family Coriobacteriaceae, the family Bifidobacteriaceae, and the family Erysipelotrichaceae was significantly different between Crohn's disease patients and normal individuals.

In addition, in one embodiment of the present invention, as a result of performing bacterial metagenomic analysis on vesicles present in subject-derived stool samples at a genus level, the content of vesicles derived from bacteria belonging to the genus *Cupriavidus*, the genus *Citrobacter*, the genus *Methylobacterium*, the genus *Paracoccus*, the genus *Proteus*, the genus *Enhydrobacter*, the genus *Halomonas*, the genus *Neisseria*, the genus *Parabacteroides*, the genus *Rothia*, the genus *Pseudomonas*, the genus *Bacillus*, the genus *Fusobacterium*, the genus *Lactococcus*, the genus *Roseburia*, the genus *Prevotella*, the genus *Propionibacterium*, the genus *Corynebacterium*, the genus *Oscillospira*, the genus *Klebsiella*, the genus *Eggerthella*, the genus *Rhodococcus*, the genus *Blautia*, the genus *Bifidobacterium*, the genus *Coprococcus*, the genus *Eubacterium*, the genus *Collinsella*, the genus *Ruminococcus*, and the genus *Stenotrophomonas* was significantly different between Crohn's disease patients and normal individuals.

In another embodiment of the present invention, metagenomic analysis is performed on the bacteria, and bacteria capable of acting as a cause of the onset of ulcerative colitis and Crohn's disease were actually identified by analysis at phylum, class, order, family, and genus levels (see Example 8).

More particularly, in one embodiment of the present invention, as a result of performing bacterial metagenomic analysis on bacteria present in subject-derived stool samples at a family level, the content of bacteria belonging to the family Prevotellaceae was significantly different between Crohn's disease patients and ulcerative colitis patients.

In addition, in one embodiment of the present invention, as a result of performing bacterial metagenomic analysis on bacteria present in subject-derived stool samples at a genus level, the content of bacteria belonging to the genus *Prevotella*, the genus *Roseburia*, the genus *Faecalibacterium*, and the genus *Klebsiella* was significantly different between Crohn's disease patients and ulcerative colitis patients.

In another embodiment of the present invention, metagenomic analysis is performed on the bacteria-derived vesicles, and bacteria-derived vesicles capable of acting as a cause of the onset of ulcerative colitis and Crohn's disease were actually identified by analysis at phylum, class, order, family, and genus levels (see Example 9).

More particularly, in one embodiment of the present invention, as a result of performing bacterial metagenomic analysis on vesicles present in subject-derived stool samples at a family level, the content of vesicles derived from bacteria belonging to the family Prevotellaceae was significantly different between Crohn's disease patients and ulcerative colitis patients.

In addition, in one embodiment of the present invention, as a result of performing bacterial metagenomic analysis on vesicles present in subject-derived stool samples at a genus level, the content of vesicles derived from bacteria belonging to the genus *Prevotella*, and the genus *Eggerthella* was significantly different between Crohn's disease patients and ulcerative colitis patients.

Through the results of the examples, it was confirmed that distribution variables of the identified bacteria or bacteria-derived vesicles could be usefully used for the prediction of the onset of inflammatory bowel disease.

Hereinafter, the present invention will be described with reference to exemplary examples to aid in understanding of the present invention. However, these examples are provided only for illustrative purposes and are not intended to limit the scope of the present invention.

EXAMPLES

Example 1. Analysis of In Vivo Absorption, Distribution, and Excretion Patterns of Intestinal Bacteria and Bacteria-Derived Extracellular Vesicles To evaluate whether intestinal bacteria and bacteria-derived extracellular vesicles are systematically absorbed through the gastrointestinal tract, an experiment was conducted using the following method. More particularly, 50 µg of each of intestinal bacteria and the bacteria-derived extracellular vesicles (EVs), labeled with fluorescence, were orally administered to the gastrointestinal tracts of mice, and fluorescence was measured at 0 h, and after 5 min, 3 h, 6 h, and 12 h. As a result of observing the entire images of mice, as illustrated in FIG. 1A, the bacteria were not systematically absorbed when administered, while the bacteria-derived EVs were systematically absorbed at 5 min after administration, and, at 3 h after administration, fluorescence was strongly observed in the bladder, from which it was confirmed that the EVs were excreted via the urinary system, and were present in the bodies up to 12 h after administration.

Figure 1B:
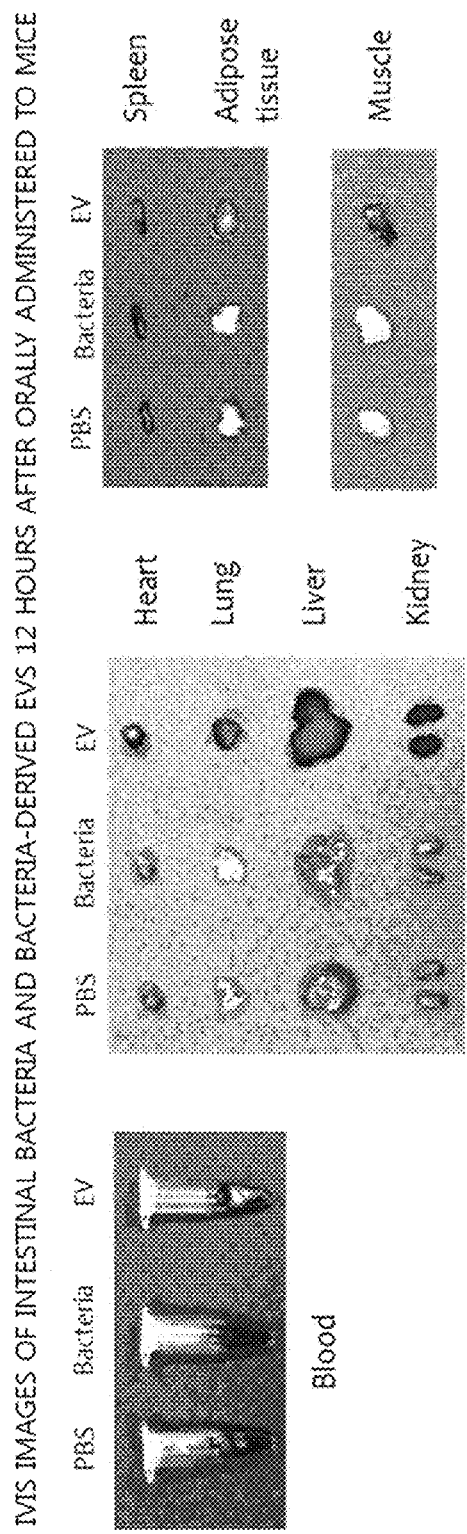

After intestinal bacteria and intestinal bacteria-derived extracellular vesicles were systematically absorbed, to evaluate a pattern of invasion of intestinal bacteria and the bacteria-derived EVs into various organs in the human body after being systematically absorbed, 50 µg of each of the bacteria and bacteria-derived EVs, labeled with fluorescence, were administered using the same method as that used above, and then, at 12 h after administration, blood, the heart, the lungs, the liver, the kidneys, the spleen, adipose tissue, and muscle were extracted from each mouse. As a result of observing fluorescence in the extracted tissues, as illustrated in FIG. 1B, it was confirmed that the intestinal bacteria were not absorbed into each organ, while the bacteria-derived EVs were distributed in the blood, heart, lungs, liver, kidneys, spleen, adipose tissue, and muscle.

Example 2. Bacteria and Bacteria-Derived Vesicle Isolation and DNA Extraction from Stool To isolate bacteria and bacteria-derived vesicles from stool and extract DNA, first, stool was added to a 10 mL tube and subjected to centrifugation (3,500×g, 10 min, 4° C.) to precipitate suspended matter, thereby collecting a pellet and a suspension, followed by transferring the suspension to a new 10 mL tube. To isolate bacteria-derived vesicles, a 0.22 µm filter was used to remove bacteria and impurities, and then the filtrate was transferred to a Centriprep tube (centrifugal filters; 50 kD) and subjected to centrifugation at 1500×g and 4° C. for 15 minutes to discard substances smaller than 50 kD and concentrate the remainder to 10 mL. A 0.22-µm filter was used again to remove bacteria and impurities.

100 µl of the bacteria and bacteria-derived vesicles isolated from the stool according to the above-described method was boiled at 100° C. to allow the internal DNA to come out of the lipid and then cooled on ice. Next, the resulting vesicles were centrifuged at 10,000×g and 4° C. for 30 minutes to remove the remaining suspension, only the supernatant was collected, and then the amount of DNA extracted was quantified using a NanoDrop sprectrophotometer. In addition, to verify whether bacteria-derived DNA was present in the extracted DNA, PCR was performed using 16s rDNA primers shown in Table 1 below.

Table 1

| Primer | | Sequence | SEQ ID NO. |
|---|---|---|---|
| 16S rDNA | 16S_V3_F | 5'-TCGTCGGCAGC GTCAGATGTGTATA AGAGACAGCCTACG GGNGGCWGCAG-3' | 1 |
| | 16S_V4_R | 5'-GTCTCGTGGGC TCGGAGATGTGTAT AAGA | 2 |

Example 3. Metagenomic Analysis Using DNA Extracted from Bacteria and Bacteria-Derived Vesicles in Stool DNA was extracted from bacteria and bacteria-derived vesicles using the same method as that used in Example 2, and then PCR was performed thereon using 16S rDNA primers shown in Table 1 to amplify DNA, followed by sequencing (Illumina MiSeq sequencer). The results were output as standard flowgram format (SFF) files, and the SFF files were converted into sequence files (.fasta) and nucleotide quality score files using GS FLX software (v2.9), and then credit rating for reads was identified, and portions with a window (20 bps) average base call accuracy of less than 99% (Phred score<20) were removed. After removing the low-quality portions, only reads having a length of 300 bps or more were used (Sickle version 1.33), and, for operational taxonomy unit (OTU) analysis, clustering was performed using UCLUST and USEARCH according to sequence similarity. In particular, clustering was performed based on sequence similarity values of 94% for genus, 90% for family, 85% for order, 80% for class, and 75% for phylum, and phylum, class, order, family, and genus levels of each OTU were classified, and bacteria with a sequence similarity of 97% or more were analyzed (QIIME) using 16S DNA sequence databases (108,453 sequences) of BLASTN and GreenGenes.

Example 4. Ulcerative Colitis Diagnostic Model Based on Metagenomic Analysis of Bacteria Isolated from Stool of Normal Individual and Ulcerative Colitis Patient Bacteria was isolated from stool samples of 70 ulcerative colitis patients and 76 normal individuals, the two groups matched in age and gender, and then metagenomic sequencing was performed thereon using the method of Example 3. For the development of a diagnostic model, first, a strain exhibiting a p value of less than 0.05 between two groups in a t-test and a difference of two-fold or more between two groups was selected, and then an area under curve (AUC), sensitivity, and specificity, which are diagnostic performance indexes, were calculated by logistic regression analysis.

Figure 2:
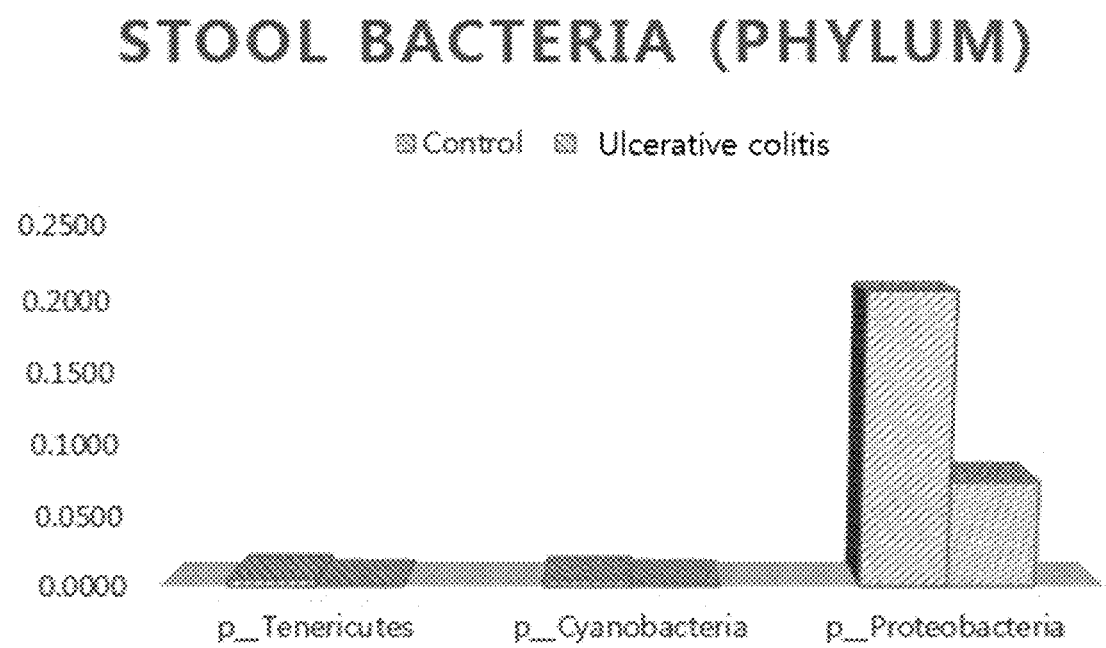
FIG. 2 is a result showing the distribution of bacteria, which is significant in diagnostic performance at the phylum level by isolating bacteria from stool of a patient with ulcerative colitis and a normal individual, and then performing a metagenomic analysis.

As a result of analyzing bacteria in stool at a phylum level, a diagnostic model developed using bacteria belonging to the phylum Tenericutes, the phylum Cyanobacteria, and the phylum Proteobacteria as a biomarker exhibited significant diagnostic performance for ulcerative colitis (see Table 2 and FIG. 2).

TABLE 2

| Phylum | Normal individual | | Ulcerative colitis | | t-test p-value | Ratio | Training Set | | | | Testing Set | | | |
|---|---|---|---|---|---|---|---|---|---|---|---|---|---|---|
| | Mean | SD | Mean | SD | | | AUC | Accuracy | sensitivity | specificity | AUC | Accuracy | sensitivity | specificity |
| Tenericutes | 0.0049 | 0.0094 | 0.0008 | 0.0028 | 0.0006 | 0.17 | 0.85 | 0.75 | 0.73 | 0.76 | 0.85 | 0.73 | 0.71 | 0.77 |
| Cyanobacteria | 0.0034 | 0.0072 | 0.0007 | 0.0040 | 0.0058 | 0.21 | 0.88 | 0.73 | 0.75 | 0.73 | 0.80 | 0.60 | 0.47 | 0.77 |
| Proteobacteria | 0.2047 | 0.2231 | 0.0740 | 0.1355 | 0.0000 | 0.36 | 0.85 | 0.83 | 0.75 | 0.78 | 0.86 | 0.60 | 0.82 | 0.77 |

Figure 3:
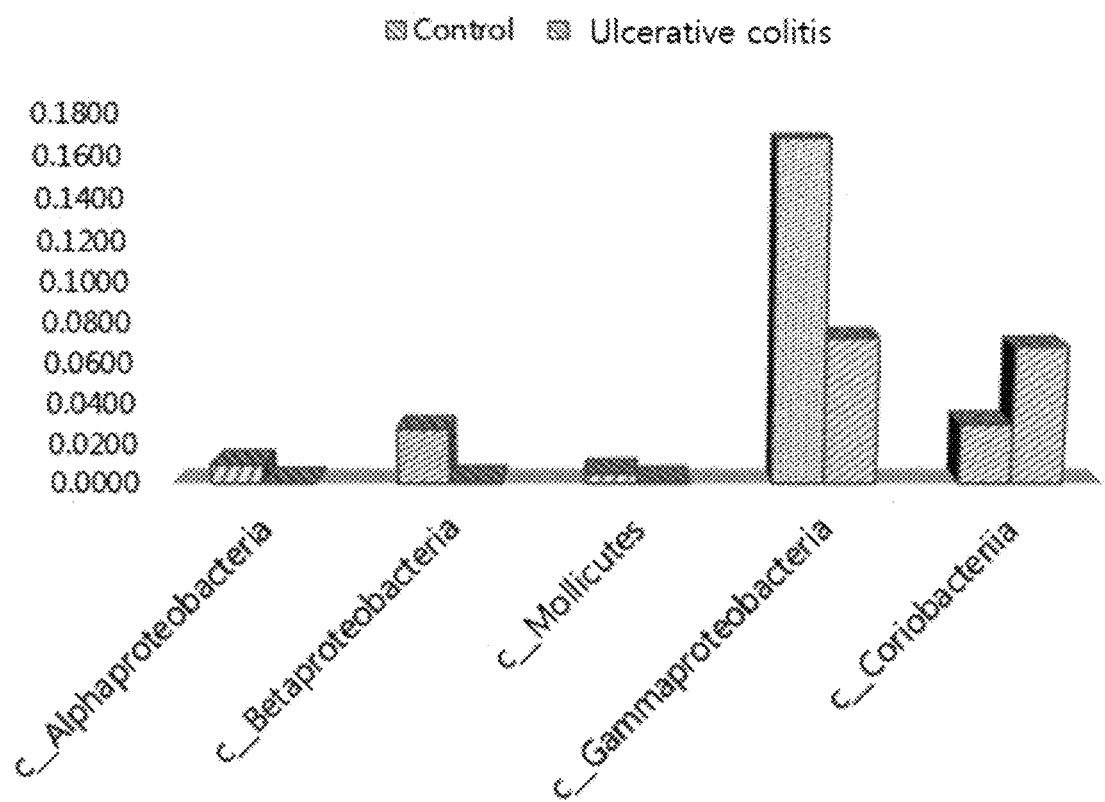
FIG. 3 is a result showing the distribution of bacteria, which is significant in diagnostic performance at the class level by isolating bacteria from stool of a patient with ulcerative colitis and a normal individual, and then performing a metagenomic analysis.

As a result of analyzing bacteria in stool at a class level, a diagnostic model developed using bacteria belonging to the class Alphaproteobacteria, the class Betaproteobacteria, the class Mollicutes, the class Gammaproteobacteria, and the class Coriobacteriia as a biomarker exhibited significant diagnostic performance for ulcerative colitis (see Table 3 and FIG. 3).

TABLE 3

| Class | Normal individual | | Ulcerative colitis | | t-test p-value | Ratio | Training Set | | | | Testing Set | | | |
|---|---|---|---|---|---|---|---|---|---|---|---|---|---|---|
| | Mean | SD | Mean | SD | | | AUC | Accuracy | sensitivity | specificity | AUC | Accuracy | sensitivity | specificity |
| Alphaproteobacteria | 0.0093 | 0.0230 | 0.0002 | 0.0005 | 0.0009 | 0.02 | 0.86 | 0.76 | 0.78 | 0.74 | 0.88 | 0.70 | 0.65 | 0.77 |
| Betaproteobacteria | 0.0270 | 0.0638 | 0.0012 | 0.0021 | 0.0008 | 0.04 | 0.90 | 0.77 | 0.78 | 0.75 | 0.88 | 0.73 | 0.71 | 0.77 |
| Mollicutes | 0.0048 | 0.0094 | 0.0008 | 0.0028 | 0.0006 | 0.16 | 0.85 | 0.73 | 0.76 | 0.70 | 0.85 | 0.73 | 0.71 | 0.77 |
| Gammaproteobacteria | 0.1670 | 0.2140 | 0.0717 | 0.1360 | 0.0017 | 0.43 | 0.84 | 0.76 | 0.78 | 0.74 | 0.84 | 0.80 | 0.82 | 0.77 |
| Coriobacteriia | 0.0293 | 0.0336 | 0.0676 | 0.0695 | 0.0001 | 2.31 | 0.86 | 0.85 | 0.92 | 0.79 | 0.86 | 0.80 | 0.76 | 0.85 |

Figure 4:
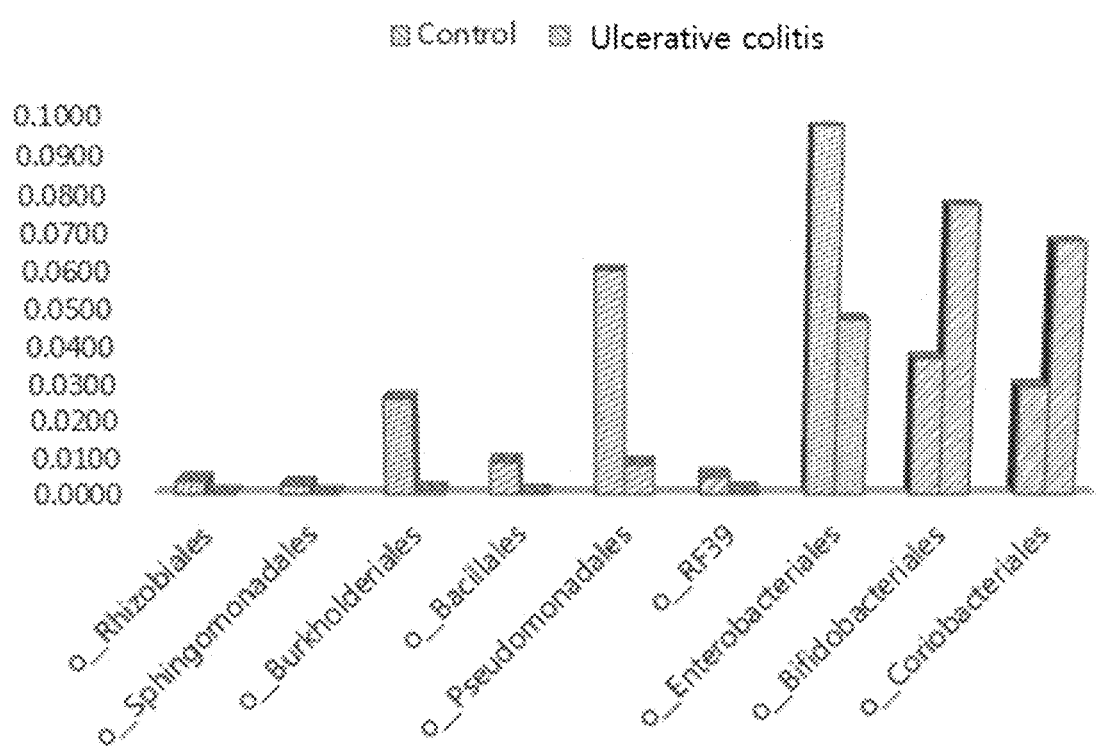
FIG. 4 is a result showing the distribution of bacteria, which is significant in diagnostic performance at the order level by isolating bacteria from stool of a patient with ulcerative colitis and a normal individual, and then performing a metagenomic analysis.

As a result of analyzing bacteria in stool at an order level, a diagnostic model developed using bacteria belonging to the order Rhizobiales, the order Sphingomonadales, the order Burkholderiales, the order Bacillales, the order Pseudomonadales, the order RF39, the order Enterobacteriales, the order Bifidobacteriales, and the order Coriobacteriales as a biomarker exhibited significant diagnostic performance for ulcerative colitis (see Table 4 and FIG. 4).

TABLE 4

| Order | Normal individual Mean | SD | Ulcerative colitis Mean | SD | t-test p-value | Ratio | AUC | Training Set Accuracy | sensitivity | specificity | AUC | Testing Set Accuracy | sensitivity | specificity |
|---|---|---|---|---|---|---|---|---|---|---|---|---|---|---|
| Rhizobiales | 0.0037 | 0.0102 | 0.0000 | 0.0000 | 0.0024 | 0.00 | 0.89 | 0.77 | 0.78 | 0.75 | 0.89 | 0.70 | 0.65 | 0.77 |
| Sphingomonadales | 0.0025 | 0.0080 | 0.0000 | 0.0000 | 0.0101 | 0.01 | 0.85 | 0.76 | 0.78 | 0.74 | 0.86 | 0.73 | 0.71 | 0.77 |
| Burkholderiales | 0.0261 | 0.0634 | 0.0011 | 0.0021 | 0.0010 | 0.04 | 0.89 | 0.77 | 0.78 | 0.75 | 0.88 | 0.73 | 0.71 | 0.77 |
| Bacillales | 0.0088 | 0.0282 | 0.0004 | 0.0006 | 0.0116 | 0.04 | 0.85 | 0.75 | 0.76 | 0.74 | 0.85 | 0.70 | 0.65 | 0.77 |
| Pseudomonadales | 0.0601 | 0.1633 | 0.0082 | 0.0654 | 0.0126 | 0.14 | 0.84 | 0.76 | 0.78 | 0.74 | 0.83 | 0.80 | 0.82 | 0.77 |
| RF39 | 0.0048 | 0.0094 | 0.0008 | 0.0028 | 0.0006 | 0.16 | 0.85 | 0.73 | 0.76 | 0.70 | 0.85 | 0.73 | 0.71 | 0.77 |
| Enterobacteriales | 0.0974 | 0.1520 | 0.0472 | 0.1167 | 0.0270 | 0.48 | 0.83 | 0.76 | 0.78 | 0.74 | 0.83 | 0.80 | 0.82 | 0.77 |
| Bifidobacteriales | 0.0367 | 0.0507 | 0.0772 | 0.0744 | 0.0002 | 2.10 | 0.84 | 0.80 | 0.88 | 0.72 | 0.79 | 0.73 | 0.71 | 0.77 |
| Coriobacteriales | 0.0293 | 0.0336 | 0.0676 | 0.0695 | 0.0001 | 2.31 | 0.86 | 0.85 | 0.92 | 0.79 | 0.86 | 0.80 | 0.76 | 0.85 |

Figure 5:
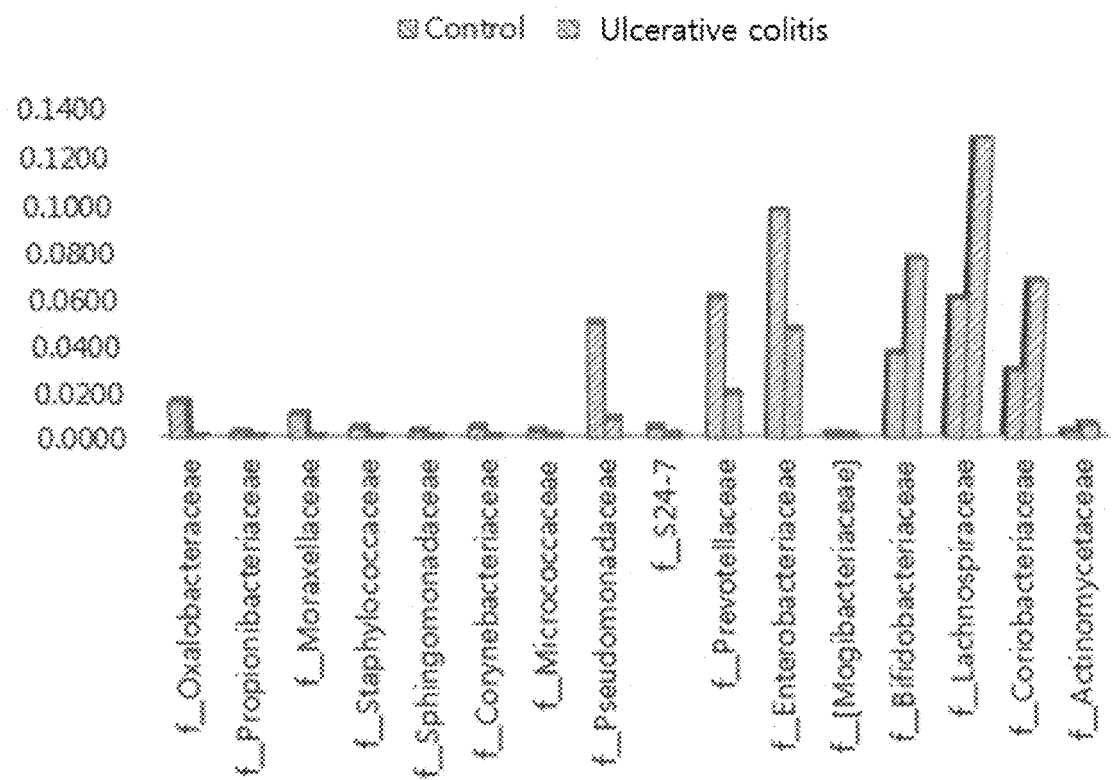
FIG. 5 is a result showing the distribution of bacteria, which is significant in diagnostic performance at the family level by isolating bacteria from stool of a patient with ulcerative colitis and a normal individual, and then performing a metagenomic analysis.

As a result of analyzing bacteria in stool at a family level, a diagnostic model developed using bacteria belonging to the family Oxalobacteraceae, the family Propionibacteriaceae, the family Moraxellaceae, the family Staphylococcaceae, the family Sphingomonadaceae, the family Corynebacteriaceae, the family Micrococcaceae, the family Pseudomonadaceae, the family S24-7, the family Prevotellaceae, the family Enterobacteriaceae, the family Mogibacteriaceae, the family Bifidobacteriaceae, the family Lachnospiraceae, the family Coriobacteriaceae, and the family Actinomycetaceae as a biomarker exhibited significant diagnostic performance for ulcerative colitis (see Table 5 and FIG. 5).

TABLE 5

| Family | Normal individual Mean | SD | Ulcerative colitis Mean | SD | t-test p-value | Ratio | AUC | Training Set Accuracy | sensitivity | specificity | AUC | Testing Set Accuracy | sensitivity | specificity |
|---|---|---|---|---|---|---|---|---|---|---|---|---|---|---|
| Oxalobacteraceae | 0.0157 | 0.0451 | 0.0000 | 0.0002 | 0.0035 | 0.00 | 0.92 | 0.80 | 0.83 | 0.77 | 0.92 | 0.83 | 0.76 | 0.92 |
| Propionibacteriaceae | 0.0018 | 0.0056 | 0.0000 | 0.0000 | 0.0062 | 0.00 | 0.85 | 0.77 | 0.78 | 0.75 | 0.85 | 0.67 | 0.59 | 0.77 |
| Moraxellaceae | 0.0102 | 0.0289 | 0.0000 | 0.0001 | 0.0031 | 0.00 | 0.87 | 0.76 | 0.78 | 0.74 | 0.86 | 0.67 | 0.53 | 0.85 |
| Staphylococcaceae | 0.0041 | 0.0122 | 0.0000 | 0.0002 | 0.0053 | 0.01 | 0.85 | 0.75 | 0.76 | 0.74 | 0.85 | 0.67 | 0.59 | 0.77 |
| Sphingomonadaceae | 0.0024 | 0.0075 | 0.0000 | 0.0000 | 0.0087 | 0.01 | 0.85 | 0.76 | 0.78 | 0.74 | 0.86 | 0.73 | 0.71 | 0.77 |
| Corynebacteriaceae | 0.0043 | 0.0138 | 0.0001 | 0.0003 | 0.0091 | 0.02 | 0.85 | 0.75 | 0.76 | 0.74 | 0.85 | 0.70 | 0.65 | 0.77 |
| Micrococcaceae | 0.0025 | 0.0066 | 0.0003 | 0.0007 | 0.0056 | 0.13 | 0.85 | 0.75 | 0.76 | 0.74 | 0.84 | 0.63 | 0.53 | 0.77 |
| Pseudomonadaceae | 0.0498 | 0.1541 | 0.0081 | 0.0654 | 0.0347 | 0.16 | 0.83 | 0.76 | 0.78 | 0.74 | 0.81 | 0.80 | 0.82 | 0.77 |
| S24-7 | 0.0043 | 0.0107 | 0.0012 | 0.0055 | 0.0296 | 0.27 | 0.84 | 0.76 | 0.78 | 0.74 | 0.81 | 0.70 | 0.65 | 0.77 |
| Prevotellaceae | 0.0608 | 0.0848 | 0.0195 | 0.0451 | 0.0003 | 0.32 | 0.84 | 0.75 | 0.76 | 0.74 | 0.86 | 0.70 | 0.65 | 0.77 |
| Enterobacteriaceae | 0.0974 | 0.1520 | 0.0472 | 0.1167 | 0.0270 | 0.48 | 0.83 | 0.76 | 0.78 | 0.74 | 0.83 | 0.80 | 0.82 | 0.77 |
| [Mogibacteriaceae] | 0.0014 | 0.0026 | 0.0007 | 0.0016 | 0.0497 | 0.49 | 0.83 | 0.76 | 0.80 | 0.72 | 0.81 | 0.73 | 0.71 | 0.77 |
| Bifidobacteriaceae | 0.0367 | 0.0507 | 0.0772 | 0.0744 | 0.0002 | 2.10 | 0.84 | 0.80 | 0.88 | 0.72 | 0.79 | 0.73 | 0.71 | 0.77 |
| Lachnospiraceae | 0.0603 | 0.0376 | 0.1271 | 0.0896 | 0.0000 | 2.11 | 0.85 | 0.80 | 0.85 | 0.75 | 0.90 | 0.83 | 0.82 | 0.85 |
| Coriobacteriaceae | 0.0293 | 0.0336 | 0.0676 | 0.0695 | 0.0001 | 2.31 | 0.86 | 0.85 | 0.92 | 0.79 | 0.86 | 0.80 | 0.76 | 0.85 |
| Actinomycetaceae | 0.0025 | 0.0036 | 0.0058 | 0.0115 | 0.0248 | 2.33 | 0.84 | 0.76 | 0.76 | 0.75 | 0.85 | 0.80 | 0.82 | 0.77 |

Figure 6:
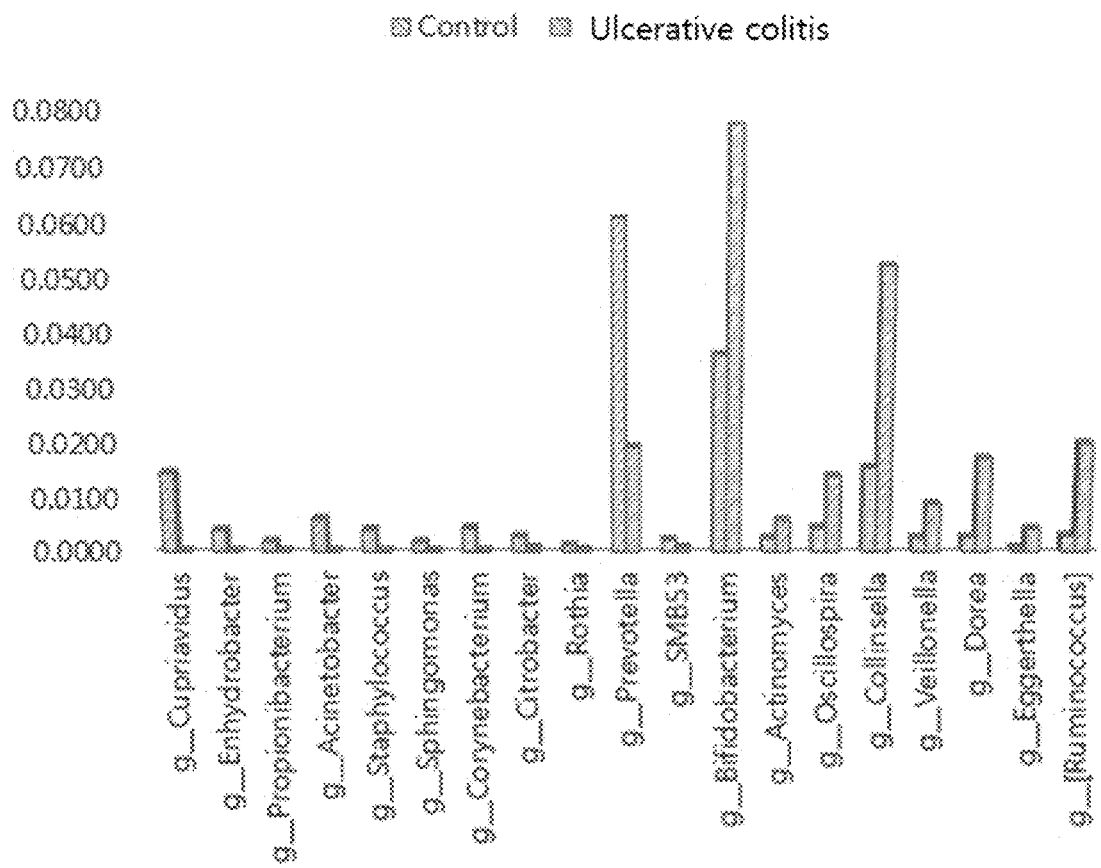
FIG. 6 is a result showing the distribution of bacteria, which is significant in diagnostic performance at the genus level by isolating bacteria from stool of a patient with ulcerative colitis and a normal individual, and then performing a metagenomic analysis.

As a result of analyzing bacteria in stool at a genus level, a diagnostic model developed using bacteria belonging to the genus *Cupriavidus*, the genus *Enhydrobacter*, the genus *Propionibacterium*, the genus *Acinetobacter*, the genus *Staphylococcus*, the genus *Sphingomonas*, the genus *Corynebacterium*, the genus *Citrobacter*, the genus *Rothia*, the genus *Prevotella*, the genus SMB53, the genus *Bifidobacterium*, the genus *Actinomyces*, the genus *Oscillospira*, the genus *Collinsella*, the genus *Veillonella*, the genus *Dorea*, the genus *Eggerthella*, and the genus *Ruminococcus* as a biomarker exhibited significant diagnostic performance for ulcerative colitis (see Table 6 and FIG. 6).

TABLE 6

| Genus | Normal individual Mean | SD | Ulcerative colitis Mean | SD | t-test p-value | Ratio | AUC | Training Set Accuracy | sensitivity | specificity | AUC | Testing Set Accuracy | sensitivity | specificity |
|---|---|---|---|---|---|---|---|---|---|---|---|---|---|---|
| Cupriavidus | 0.0147 | 0.0438 | 0.0000 | 0.0000 | 0.0060 | 0.00 | 0.97 | 0.89 | 0.86 | 0.91 | 0.93 | 0.87 | 0.82 | 0.92 |
| Enhydrobacter | 0.0040 | 0.0164 | 0.0000 | 0.0000 | 0.0386 | 0.00 | 0.86 | 0.76 | 0.78 | 0.74 | 0.87 | 0.73 | 0.71 | 0.77 |
| Propionibacterium | 0.0018 | 0.0056 | 0.0000 | 0.0000 | 0.0061 | 0.00 | 0.85 | 0.77 | 0.78 | 0.75 | 0.85 | 0.67 | 0.59 | 0.77 |
| Acinetobacter | 0.0061 | 0.0176 | 0.0000 | 0.0001 | 0.0041 | 0.00 | 0.86 | 0.76 | 0.78 | 0.74 | 0.86 | 0.67 | 0.59 | 0.77 |
| Staphylococcus | 0.0041 | 0.0121 | 0.0000 | 0.0001 | 0.0053 | 0.01 | 0.85 | 0.75 | 0.76 | 0.74 | 0.85 | 0.67 | 0.59 | 0.77 |
| Sphingomonas | 0.0017 | 0.0052 | 0.0000 | 0.0000 | 0.0057 | 0.01 | 0.85 | 0.76 | 0.78 | 0.74 | 0.86 | 0.73 | 0.71 | 0.77 |
| Corynebacterium | 0.0043 | 0.0138 | 0.0001 | 0.0003 | 0.0091 | 0.02 | 0.85 | 0.75 | 0.76 | 0.74 | 0.85 | 0.70 | 0.65 | 0.77 |
| Citrobacter | 0.0028 | 0.0085 | 0.0005 | 0.0018 | 0.0271 | 0.19 | 0.84 | 0.75 | 0.78 | 0.72 | 0.86 | 0.73 | 0.71 | 0.77 |
| Rothia | 0.0011 | 0.0027 | 0.0003 | 0.0006 | 0.0218 | 0.29 | 0.84 | 0.75 | 0.76 | 0.74 | 0.83 | 0.63 | 0.53 | 0.77 |
| Prevotella | 0.0608 | 0.0847 | 0.0195 | 0.0451 | 0.0003 | 0.32 | 0.84 | 0.75 | 0.76 | 0.74 | 0.86 | 0.70 | 0.65 | 0.77 |
| SMB53 | 0.0021 | 0.0039 | 0.0007 | 0.0015 | 0.0043 | 0.32 | 0.84 | 0.75 | 0.76 | 0.74 | 0.85 | 0.73 | 0.71 | 0.77 |
| Bifidobacterium | 0.0364 | 0.0507 | 0.0771 | 0.0744 | 0.0002 | 2.12 | 0.84 | 0.80 | 0.88 | 0.72 | 0.79 | 0.73 | 0.71 | 0.77 |
| Actinomyces | 0.0024 | 0.0036 | 0.0057 | 0.0115 | 0.0247 | 2.37 | 0.84 | 0.76 | 0.76 | 0.75 | 0.85 | 0.80 | 0.82 | 0.77 |
| Oscillospira | 0.0044 | 0.0050 | 0.0140 | 0.0264 | 0.0041 | 3.16 | 0.87 | 0.78 | 0.83 | 0.72 | 0.81 | 0.77 | 0.76 | 0.77 |
| Collinsella | 0.0157 | 0.0231 | 0.0524 | 0.0677 | 0.0000 | 3.34 | 0.86 | 0.86 | 0.93 | 0.79 | 0.86 | 0.77 | 0.76 | 0.77 |
| Veillonella | 0.0025 | 0.0071 | 0.0088 | 0.0254 | 0.0478 | 3.57 | 0.85 | 0.79 | 0.83 | 0.75 | 0.90 | 0.80 | 0.76 | 0.85 |
| Dorea | 0.0027 | 0.0031 | 0.0173 | 0.0206 | 0.0000 | 6.44 | 0.90 | 0.86 | 0.93 | 0.79 | 0.86 | 0.83 | 0.82 | 0.85 |
| Eggerthella | 0.0006 | 0.0019 | 0.0042 | 0.0105 | 0.0065 | 6.76 | 0.83 | 0.78 | 0.86 | 0.70 | 0.80 | 0.80 | 0.82 | 0.77 |
| [Ruminococcus] | 0.0029 | 0.0039 | 0.0202 | 0.0338 | 0.0001 | 7.02 | 0.90 | 0.85 | 0.92 | 0.79 | 0.88 | 0.80 | 0.71 | 0.92 |

Example 5. Ulcerative Colitis Diagnostic Model Based on MetaQenomic Analysis of Bacteria-Derived Vesicles Isolated from Stool of Normal Individual and Ulcerative Colitis Patient Vesicles were isolated from stool samples of 70 ulcerative colitis patients and 76 normal individuals, the two groups matched in age and gender, and then metagenomic sequencing was performed thereon using the method of Example 3. For the development of a diagnostic model, first, a strain exhibiting a p value of less than 0.05 between two groups in a t-test and a difference of two-fold or more between two groups was selected, and then an area under curve (AUC), sensitivity, and specificity, which are diagnostic performance indexes, were calculated by logistic regression analysis.

Figure 7:
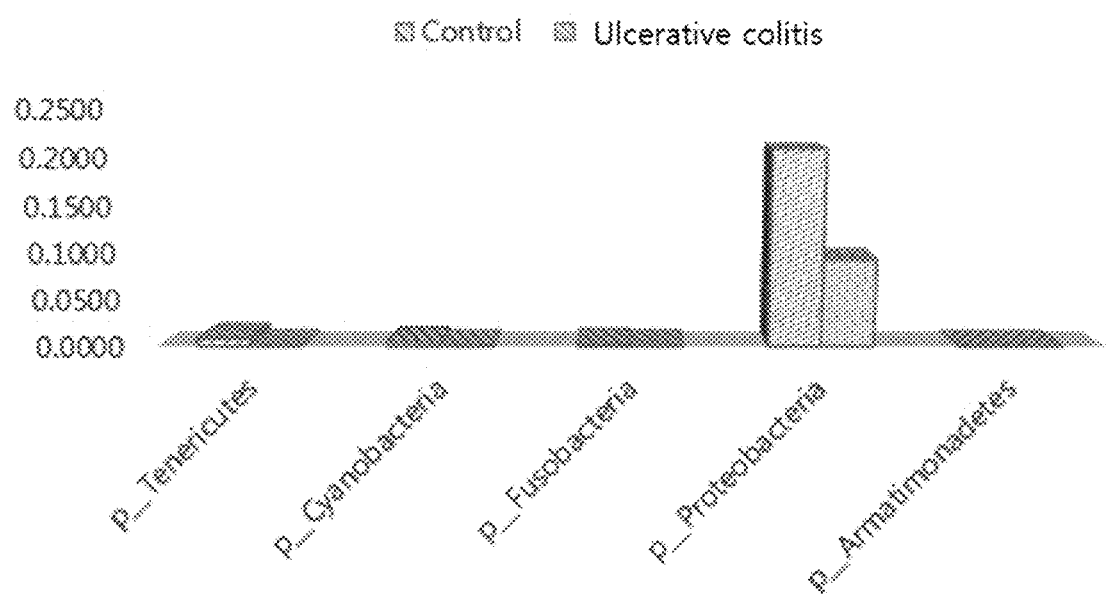
FIG. 7 is a result showing the distribution of bacteria-derived vesicles (EVs), which is significant in diagnostic performance at the phylum level by isolating bacteria-derived vesicles from stool of a patient with ulcerative colitis and a normal individual, and then performing a metagenomic analysis.

As a result of analyzing vesicles derived from bacteria in stool at a phylum level, a diagnostic model developed using vesicles derived from bacteria belonging to the phylum Tenericutes, the phylum Cyanobacteria, the phylum Fusobacteria, the phylum Proteobacteria, and the phylum Armatimonadetes as a biomarker exhibited significant diagnostic performance for ulcerative colitis (see Table 7 and FIG. 7).

TABLE 7

| Phylum | Normal individual Mean | SD | Ulcerative colitis Mean | SD | t-test p-value | Ratio | AUC | Training Set Accuracy | sensitivity | specificity | AUC | Testing Set Accuracy | sensitivity | specificity |
|---|---|---|---|---|---|---|---|---|---|---|---|---|---|---|
| Tenericutes | 0.0086 | 0.0286 | 0.0010 | 0.0056 | 0.0275 | 0.12 | 0.83 | 0.79 | 0.85 | 0.73 | 0.87 | 0.83 | 0.87 | 0.79 |
| Cyanobacteria | 0.0046 | 0.0066 | 0.0008 | 0.0015 | 0.0000 | 0.17 | 0.91 | 0.83 | 0.85 | 0.80 | 0.89 | 0.76 | 0.73 | 0.79 |
| Fusobacteria | 0.0028 | 0.0062 | 0.0011 | 0.0025 | 0.0354 | 0.41 | 0.84 | 0.80 | 0.87 | 0.73 | 0.87 | 0.86 | 0.93 | 0.79 |
| Proteobacteria | 0.2071 | 0.1832 | 0.0925 | 0.1312 | 0.0000 | 0.45 | 0.87 | 0.81 | 0.87 | 0.75 | 0.87 | 0.79 | 0.73 | 0.86 |
| Armatimonadetes | 0.0002 | 0.0007 | 0.0005 | 0.0010 | 0.0335 | 2.35 | 0.83 | 0.78 | 0.87 | 0.67 | 0.88 | 0.79 | 0.80 | 0.79 |

Figure 8:
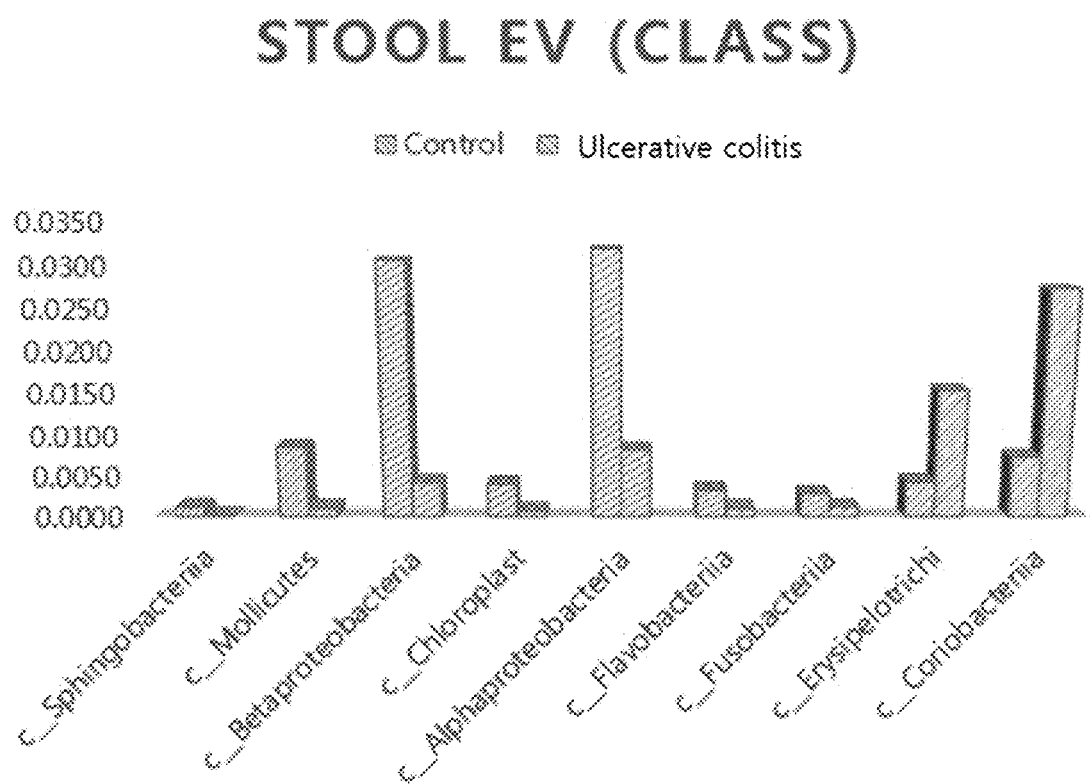
FIG. 8 is a result showing the distribution of bacteria-derived vesicles (EVs), which is significant in diagnostic performance at the class level by isolating bacteria-derived vesicles from stool of a patient with ulcerative colitis and a normal individual, and then performing a metagenomic analysis.

As a result of analyzing vesicles derived from bacteria in stool at a class level, a diagnostic model developed using vesicles derived from bacteria belonging to the class Sphingobacteriia, the class Mollicutes, the class Betaproteobacteria, the class Chloroplast, the class Alphaproteobacteria, the class Flavobacteriia, the class Fusobacteriia, the class Erysipelotrichi, and the class Coriobacteriia as a biomarker exhibited significant diagnostic performance for ulcerative colitis (see Table 8 and FIG. 8).

TABLE 8

| Class | Normal individual Mean | Normal individual SD | Ulcerative colitis Mean | Ulcerative colitis SD | t-test p-value | Ratio | AUC | Training Set Accuracy | Training Set sensitivity | Training Set specificity | AUC | Testing Set Accuracy | Testing Set sensitivity | Testing Set specificity |
|---|---|---|---|---|---|---|---|---|---|---|---|---|---|---|
| Sphingobacteriia | 0.0012 | 0.0021 | 0.0001 | 0.0003 | 0.0000 | 0.05 | 0.91 | 0.78 | 0.79 | 0.78 | 0.92 | 0.79 | 0.73 | 0.86 |
| Mollicutes | 0.0085 | 0.0285 | 0.0010 | 0.0056 | 0.0289 | 0.12 | 0.83 | 0.79 | 0.85 | 0.73 | 0.87 | 0.83 | 0.87 | 0.79 |
| Betaproteobacteria | 0.0305 | 0.0666 | 0.0042 | 0.0061 | 0.0010 | 0.14 | 0.95 | 0.85 | 0.89 | 0.82 | 0.91 | 0.79 | 0.67 | 0.93 |
| Chloroplast | 0.0040 | 0.0061 | 0.0007 | 0.0015 | 0.0000 | 0.16 | 0.90 | 0.79 | 0.82 | 0.76 | 0.87 | 0.72 | 0.67 | 0.79 |
| Alphaproteobacteria | 0.0318 | 0.0415 | 0.0082 | 0.0089 | 0.0000 | 0.26 | 0.91 | 0.82 | 0.84 | 0.80 | 0.90 | 0.79 | 0.73 | 0.86 |
| Flavobacteriia | 0.0032 | 0.0048 | 0.0010 | 0.0015 | 0.0002 | 0.31 | 0.87 | 0.78 | 0.82 | 0.73 | 0.90 | 0.83 | 0.87 | 0.79 |
| Fusobacteriia | 0.0028 | 0.0062 | 0.0011 | 0.0025 | 0.0354 | 0.41 | 0.84 | 0.80 | 0.87 | 0.73 | 0.87 | 0.86 | 0.93 | 0.79 |
| Erysipelotrichi | 0.0043 | 0.0058 | 0.0153 | 0.0193 | 0.0000 | 3.59 | 0.87 | 0.82 | 0.90 | 0.73 | 0.92 | 0.90 | 0.93 | 0.86 |
| Coriobacteriia | 0.0073 | 0.0131 | 0.0272 | 0.0405 | 0.0002 | 3.74 | 0.86 | 0.84 | 0.92 | 0.75 | 0.93 | 0.86 | 0.93 | 0.79 |

Figure 9:
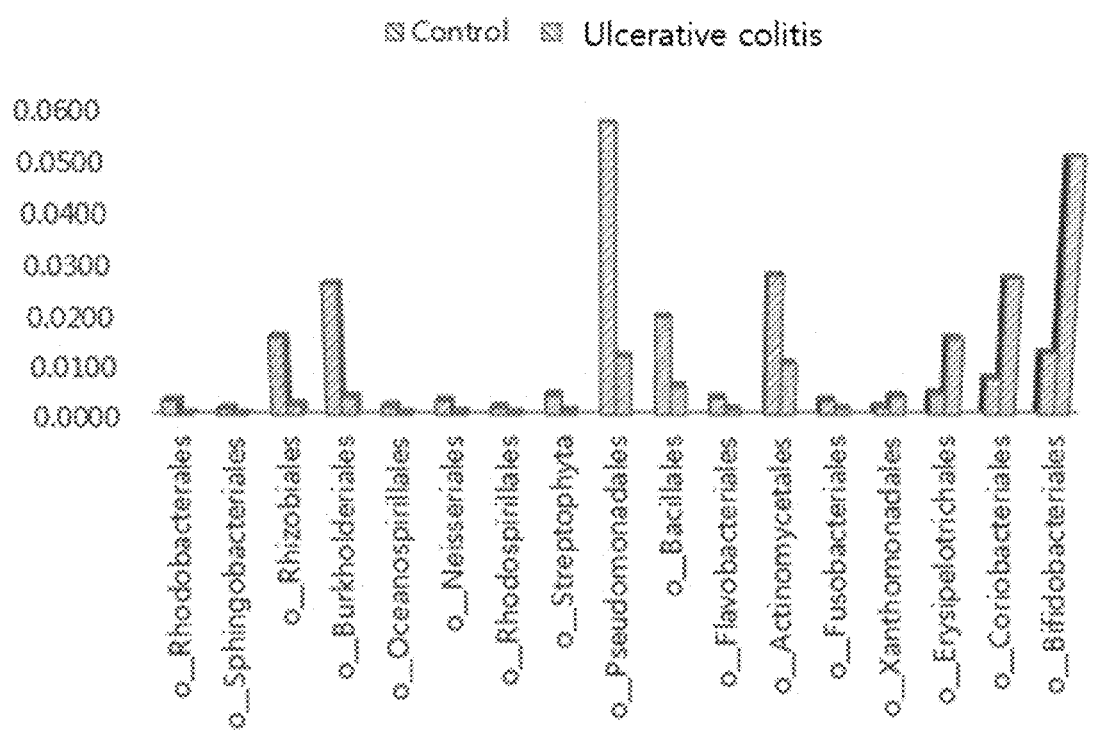
FIG. 9 is a result showing the distribution of bacteria-derived vesicles (EVs), which is significant in diagnostic performance at the order level by isolating bacteria-derived vesicles from stool of a patient with ulcerative colitis and a normal individual, and then performing a metagenomic analysis.

As a result of analyzing vesicles derived from bacteria in stool at an order level, a diagnostic model developed using vesicles derived from bacteria belonging to the order Rhodobacterales, the order Sphingobacteriales, the order Rhizobiales, the order Burkholderiales, the order Oceanospirillales, the order Neisseriales, the order Rhodospirillales, the order Streptophyta, the order Pseudomonadales, the order Bacillales, the order Flavobacteriales, the order Actinomycetales, the order Fusobacteriales, the order Xanthomonadales, the order Erysipelotrichales, the order Coriobacteriales, and the order Bifidobacteriales as a biomarker exhibited significant diagnostic performance for ulcerative colitis (see Table 9 and FIG. 9).

Intrasporangiaceae, the family Sphingobacteriaceae, the family Methylobacteriaceae, the family Nocardioidaceae, the family Pseudomonadaceae, the family Bacillaceae, the family Neisseriaceae, the family Acetobacteraceae, the family Micrococcaceae, the family 524-7, the family Halomonadaceae, the family Planococcaceae, the family Peptococcaceae, the family Comamonadaceae, the family Rikenellaceae, the family Moraxellaceae, the family Propionibacteriaceae, the family Staphylococcaceae, the family Weeksellaceae, the family Paraprevotellaceae, the family Corynebacteriaceae, the family Fusobacteriaceae, the family Nocardiaceae, the family Streptococcaceae, the family

TABLE 9

| Order | Normal individual Mean | Normal individual SD | Ulcerative colitis Mean | Ulcerative colitis SD | t-test p-value | Ratio | AUC | Training Set Accuracy | Training Set sensitivity | Training Set specificity | AUC | Testing Set Accuracy | Testing Set sensitivity | Testing Set specificity |
|---|---|---|---|---|---|---|---|---|---|---|---|---|---|---|
| Rhodobacterales | 0.0029 | 0.0048 | 0.0001 | 0.0004 | 0.0000 | 0.03 | 0.93 | 0.82 | 0.82 | 0.82 | 0.91 | 0.79 | 0.73 | 0.86 |
| Sphingobacteriales | 0.0012 | 0.0021 | 0.0001 | 0.0003 | 0.0000 | 0.05 | 0.91 | 0.78 | 0.79 | 0.78 | 0.92 | 0.79 | 0.73 | 0.86 |
| Rhizobiales | 0.0157 | 0.0312 | 0.0020 | 0.0030 | 0.0003 | 0.13 | 0.91 | 0.83 | 0.84 | 0.82 | 0.92 | 0.76 | 0.67 | 0.86 |
| Burkholderiales | 0.0262 | 0.0658 | 0.0035 | 0.0059 | 0.0040 | 0.13 | 0.93 | 0.83 | 0.84 | 0.82 | 0.90 | 0.79 | 0.73 | 0.86 |
| Oceanospirillales | 0.0016 | 0.0051 | 0.0003 | 0.0007 | 0.0219 | 0.15 | 0.85 | 0.81 | 0.85 | 0.76 | 0.88 | 0.83 | 0.87 | 0.79 |
| Neisseriales | 0.0028 | 0.0054 | 0.0004 | 0.0011 | 0.0003 | 0.15 | 0.89 | 0.78 | 0.80 | 0.75 | 0.84 | 0.83 | 0.87 | 0.79 |
| Rhodospirillales | 0.0014 | 0.0047 | 0.0002 | 0.0006 | 0.0310 | 0.16 | 0.87 | 0.79 | 0.82 | 0.76 | 0.89 | 0.79 | 0.73 | 0.86 |
| Streptophyta | 0.0039 | 0.0061 | 0.0007 | 0.0015 | 0.0000 | 0.17 | 0.90 | 0.79 | 0.82 | 0.76 | 0.86 | 0.69 | 0.60 | 0.79 |
| Pseudomonadales | 0.0571 | 0.0526 | 0.0117 | 0.0117 | 0.0000 | 0.21 | 0.93 | 0.84 | 0.87 | 0.80 | 0.91 | 0.83 | 0.80 | 0.86 |
| Bacillales | 0.0196 | 0.0300 | 0.0056 | 0.0059 | 0.0002 | 0.29 | 0.87 | 0.78 | 0.84 | 0.73 | 0.89 | 0.83 | 0.80 | 0.86 |
| Flavobacteriales | 0.0032 | 0.0048 | 0.0010 | 0.0015 | 0.0002 | 0.31 | 0.87 | 0.78 | 0.82 | 0.73 | 0.90 | 0.83 | 0.87 | 0.79 |
| Actinomycetales | 0.0278 | 0.0333 | 0.0103 | 0.0101 | 0.0000 | 0.37 | 0.89 | 0.81 | 0.84 | 0.78 | 0.89 | 0.79 | 0.73 | 0.86 |
| Fusobacteriales | 0.0028 | 0.0062 | 0.0011 | 0.0025 | 0.0354 | 0.41 | 0.84 | 0.80 | 0.87 | 0.73 | 0.87 | 0.86 | 0.93 | 0.79 |
| Xanthomonadales | 0.0014 | 0.0029 | 0.0037 | 0.0055 | 0.0034 | 2.58 | 0.83 | 0.78 | 0.85 | 0.71 | 0.86 | 0.79 | 0.80 | 0.79 |
| Erysipelotrichales | 0.0043 | 0.0058 | 0.0153 | 0.0193 | 0.0000 | 3.59 | 0.87 | 0.82 | 0.90 | 0.73 | 0.92 | 0.90 | 0.93 | 0.86 |
| Coriobacteriales | 0.0073 | 0.0131 | 0.0272 | 0.0405 | 0.0002 | 3.74 | 0.86 | 0.84 | 0.92 | 0.75 | 0.93 | 0.86 | 0.93 | 0.79 |
| Bifidobacteriales | 0.0124 | 0.0126 | 0.0506 | 0.1112 | 0.0063 | 4.08 | 0.86 | 0.82 | 0.92 | 0.71 | 0.91 | 0.83 | 0.87 | 0.79 |

Figure 10:
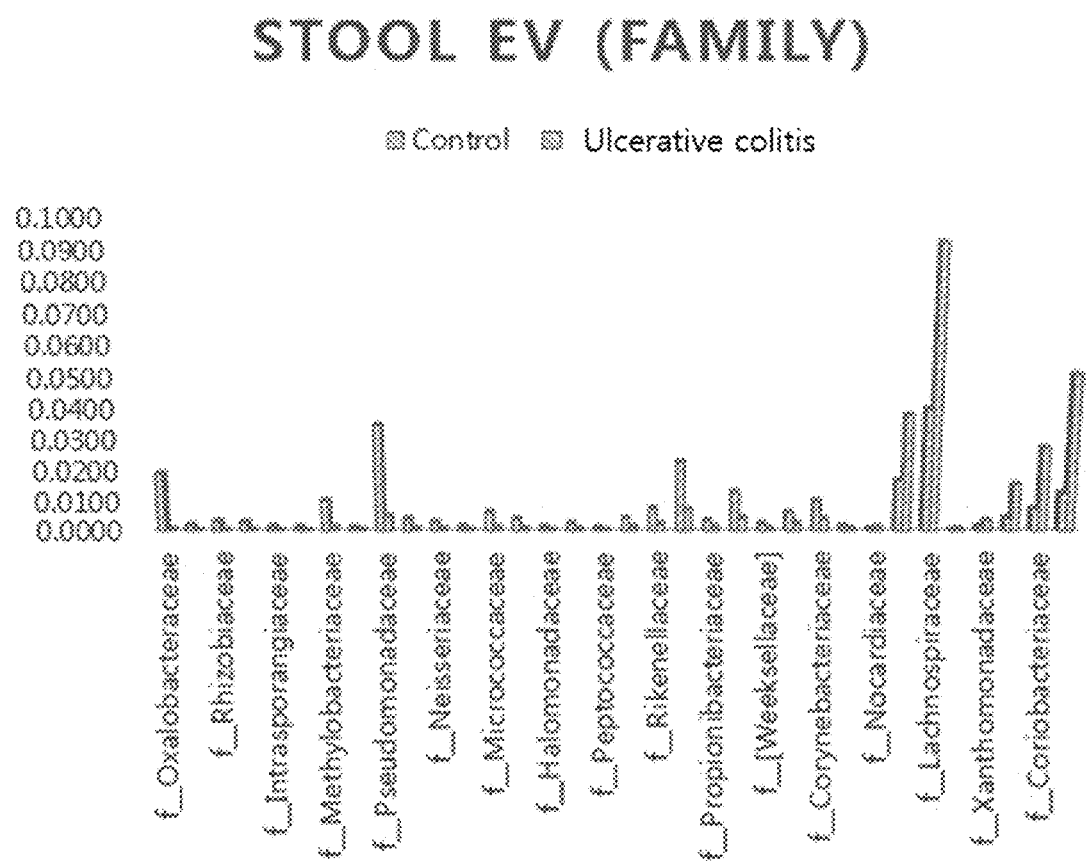
FIG. 10 is a result showing the distribution of bacteria-derived vesicles (EVs), which is significant in diagnostic performance at the family level by isolating bacteria-derived vesicles from stool of a patient with ulcerative colitis and a normal individual, and then performing a metagenomic analysis.

As a result of analyzing vesicles derived from bacteria in stool at a family level, a diagnostic model developed using vesicles derived from bacteria belonging to the family Oxalobacteraceae, the family Aerococcaceae, the family Rhizobiaceae, the family Rhodobacteraceae, the family Lachnospiraceae, the family Fimbriimonadaceae, the family Xanthomonadaceae, the family Erysipelotrichaceae, the family Coriobacteriaceae, and the family Bifidobacteriaceae as a biomarker exhibited significant diagnostic performance for ulcerative colitis (see Table 10 and FIG. 10).

TABLE 10

| Family | Normal individual Mean | SD | Ulcerative colitis Mean | SD | t-test p-value | Ratio | Training Set AUC | Accuracy | sensitivity | specificity | Testing Set AUC | Accuracy | sensitivity | specificity |
|---|---|---|---|---|---|---|---|---|---|---|---|---|---|---|
| Oxalobacteraceae | 0.0187 | 0.0635 | 0.0003 | 0.0005 | 0.0140 | 0.02 | 0.97 | 0.90 | 0.92 | 0.87 | 0.95 | 0.83 | 0.73 | 0.93 |
| Aerococcaceae | 0.0018 | 0.0038 | 0.0000 | 0.0002 | 0.0001 | 0.03 | 0.94 | 0.84 | 0.84 | 0.84 | 0.89 | 0.86 | 0.93 | 0.79 |
| Rhizobiaceae | 0.0032 | 0.0048 | 0.0001 | 0.0003 | 0.0000 | 0.03 | 0.96 | 0.89 | 0.90 | 0.87 | 0.95 | 0.83 | 0.80 | 0.86 |
| Rhodobacteraceae | 0.0029 | 0.0048 | 0.0001 | 0.0004 | 0.0000 | 0.03 | 0.93 | 0.82 | 0.82 | 0.82 | 0.91 | 0.79 | 0.73 | 0.86 |
| Intrasporangiaceae | 0.0012 | 0.0021 | 0.0000 | 0.0001 | 0.0000 | 0.04 | 0.91 | 0.80 | 0.82 | 0.78 | 0.92 | 0.76 | 0.67 | 0.86 |
| Sphingobacteriaceae | 0.0011 | 0.0019 | 0.0001 | 0.0003 | 0.0000 | 0.05 | 0.91 | 0.78 | 0.77 | 0.78 | 0.92 | 0.79 | 0.73 | 0.86 |
| Methylobacteriaceae | 0.0099 | 0.0300 | 0.0010 | 0.0017 | 0.0129 | 0.10 | 0.86 | 0.83 | 0.90 | 0.75 | 0.90 | 0.86 | 0.87 | 0.86 |
| Nocardioidaceae | 0.0010 | 0.0032 | 0.0001 | 0.0004 | 0.0245 | 0.12 | 0.88 | 0.78 | 0.84 | 0.73 | 0.86 | 0.76 | 0.67 | 0.86 |
| Pseudomonadaceae | 0.0345 | 0.0325 | 0.0048 | 0.0053 | 0.0000 | 0.14 | 0.95 | 0.86 | 0.87 | 0.85 | 0.93 | 0.83 | 0.73 | 0.93 |
| Bacillaceae | 0.0038 | 0.0061 | 0.0006 | 0.0025 | 0.0001 | 0.15 | 0.88 | 0.81 | 0.85 | 0.76 | 0.87 | 0.83 | 0.80 | 0.86 |
| Neisseriaceae | 0.0028 | 0.0054 | 0.0004 | 0.0011 | 0.0003 | 0.15 | 0.89 | 0.78 | 0.80 | 0.75 | 0.84 | 0.83 | 0.87 | 0.79 |
| Acetobacteraceae | 0.0012 | 0.0043 | 0.0002 | 0.0006 | 0.0414 | 0.17 | 0.87 | 0.80 | 0.85 | 0.75 | 0.89 | 0.79 | 0.73 | 0.86 |
| Micrococcaceae | 0.0062 | 0.0071 | 0.0011 | 0.0014 | 0.0000 | 0.18 | 0.93 | 0.82 | 0.85 | 0.78 | 0.89 | 0.83 | 0.80 | 0.86 |
| S24-7 | 0.0037 | 0.0107 | 0.0007 | 0.0030 | 0.0236 | 0.19 | 0.83 | 0.79 | 0.85 | 0.73 | 0.87 | 0.83 | 0.87 | 0.79 |
| Halomonadaceae | 0.0011 | 0.0033 | 0.0002 | 0.0007 | 0.0254 | 0.21 | 0.84 | 0.80 | 0.85 | 0.75 | 0.88 | 0.83 | 0.87 | 0.79 |
| Planococcaceae | 0.0024 | 0.0035 | 0.0005 | 0.0009 | 0.0000 | 0.23 | 0.88 | 0.78 | 0.84 | 0.71 | 0.90 | 0.79 | 0.73 | 0.86 |
| Peptococcaceae | 0.0010 | 0.0022 | 0.0002 | 0.0006 | 0.0087 | 0.25 | 0.83 | 0.79 | 0.85 | 0.73 | 0.88 | 0.86 | 0.93 | 0.79 |
| Comamonadaceae | 0.0041 | 0.0062 | 0.0011 | 0.0015 | 0.0001 | 0.27 | 0.87 | 0.75 | 0.79 | 0.71 | 0.89 | 0.83 | 0.80 | 0.86 |
| Rikenellaceae | 0.0074 | 0.0126 | 0.0022 | 0.0069 | 0.0026 | 0.30 | 0.84 | 0.80 | 0.87 | 0.73 | 0.88 | 0.79 | 0.80 | 0.79 |
| Moraxellaceae | 0.0226 | 0.0231 | 0.0069 | 0.0077 | 0.0000 | 0.31 | 0.89 | 0.79 | 0.84 | 0.75 | 0.89 | 0.86 | 0.87 | 0.86 |
| Propionibacteriaceae | 0.0034 | 0.0050 | 0.0011 | 0.0015 | 0.0003 | 0.33 | 0.88 | 0.79 | 0.85 | 0.73 | 0.89 | 0.83 | 0.80 | 0.86 |
| Staphylococcaceae | 0.0128 | 0.0260 | 0.0042 | 0.0048 | 0.0064 | 0.33 | 0.85 | 0.78 | 0.84 | 0.73 | 0.89 | 0.86 | 0.87 | 0.86 |
| [Weeksellaceae] | 0.0023 | 0.0036 | 0.0008 | 0.0012 | 0.0010 | 0.35 | 0.85 | 0.79 | 0.85 | 0.73 | 0.90 | 0.83 | 0.87 | 0.79 |
| [Paraprevotellaceae] | 0.0061 | 0.0130 | 0.0023 | 0.0080 | 0.0379 | 0.38 | 0.83 | 0.80 | 0.85 | 0.75 | 0.86 | 0.86 | 0.93 | 0.79 |
| Corynebacteriaceae | 0.0097 | 0.0164 | 0.0038 | 0.0050 | 0.0037 | 0.39 | 0.87 | 0.82 | 0.87 | 0.76 | 0.87 | 0.86 | 0.87 | 0.86 |
| Fusobacteriaceae | 0.0016 | 0.0033 | 0.0007 | 0.0018 | 0.0408 | 0.44 | 0.83 | 0.80 | 0.87 | 0.73 | 0.87 | 0.86 | 0.93 | 0.79 |
| Nocardiaceae | 0.0005 | 0.0007 | 0.0011 | 0.0021 | 0.0257 | 2.17 | 0.84 | 0.78 | 0.80 | 0.75 | 0.87 | 0.86 | 0.93 | 0.79 |
| Streptococcaceae | 0.0164 | 0.0187 | 0.0377 | 0.0763 | 0.0281 | 2.30 | 0.83 | 0.82 | 0.87 | 0.76 | 0.86 | 0.86 | 0.93 | 0.79 |
| Lachnospiraceae | 0.0396 | 0.0324 | 0.0918 | 0.1073 | 0.0002 | 2.32 | 0.87 | 0.80 | 0.84 | 0.76 | 0.91 | 0.86 | 0.93 | 0.79 |
| [Fimbriimonadaceae] | 0.0002 | 0.0007 | 0.0005 | 0.0010 | 0.0354 | 2.34 | 0.83 | 0.78 | 0.87 | 0.67 | 0.88 | 0.79 | 0.80 | 0.79 |
| Xanthomonadaceae | 0.0013 | 0.0027 | 0.0035 | 0.0054 | 0.0029 | 2.72 | 0.83 | 0.77 | 0.82 | 0.71 | 0.85 | 0.76 | 0.80 | 0.71 |
| Erysipelotrichaceae | 0.0043 | 0.0058 | 0.0153 | 0.0193 | 0.0000 | 3.59 | 0.87 | 0.82 | 0.90 | 0.73 | 0.92 | 0.90 | 0.93 | 0.86 |
| Coriobacteriaceae | 0.0073 | 0.0131 | 0.0272 | 0.0405 | 0.0002 | 3.74 | 0.86 | 0.84 | 0.92 | 0.75 | 0.93 | 0.86 | 0.93 | 0.79 |
| Bifidobacteriaceae | 0.0124 | 0.0126 | 0.0506 | 0.1112 | 0.0063 | 4.08 | 0.86 | 0.82 | 0.92 | 0.71 | 0.91 | 0.83 | 0.87 | 0.79 |

Figure 11:
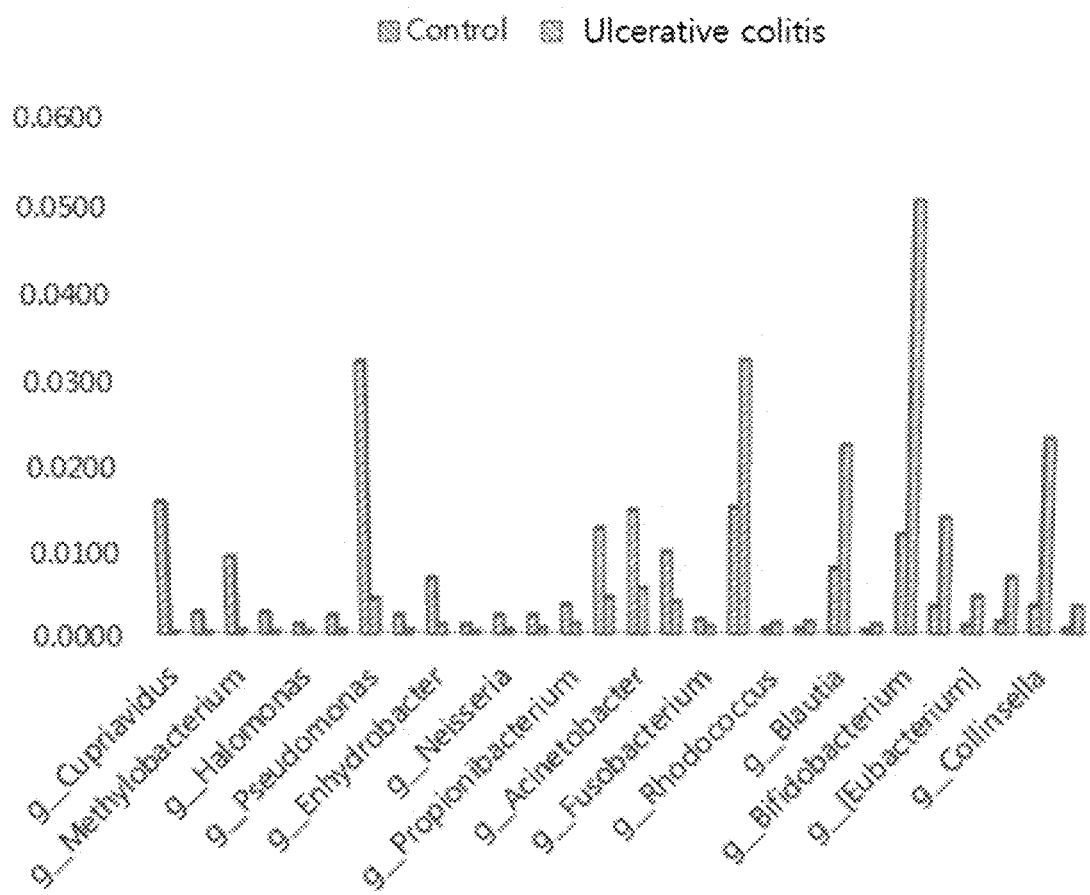
FIG. 11 is a result showing the distribution of bacteria-derived vesicles (EVs), which is significant in diagnostic performance at the genus level by isolating bacteria-derived vesicles from stool of a patient with ulcerative colitis and a normal individual, and then performing a metagenomic analysis.

As a result of analyzing vesicles derived from bacteria in stool at a genus level, a diagnostic model developed using vesicles derived from bacteria belonging to the genus Cupriavidus, the genus Paracoccus, the genus Methylobacterium, the genus Citrobacter, the genus Halomonas, the genus Bacillus, the genus Pseudomonas, the genus Micrococcus, the genus Enhydrobacter, the genus Proteus, the genus Neisseria, the genus Rothia, the genus Propionibacterium, the genus Staphylococcus, the genus Acinetobacter, the genus Corynebacterium, the genus Fusobacterium, the genus Streptococcus, the genus Rhodococcus, the genus Klebsiella, the genus Blautia, the genus Peptoniphilus, the genus Bifidobacterium, the genus Coprococcus, the genus Eubacterium, the genus Dorea, the genus Collinsella, and the genus Stenotrophomonas as a biomarker exhibited significant diagnostic performance for ulcerative colitis (see Table 11 and FIG. 11).

TABLE 11

| Genus | Normal individual Mean | SD | Ulcerative colitis Mean | SD | t-test p-value | Ratio | Training Set AUC | Accuracy | sensitivity | specificity | Testing Set AUC | Accuracy | sensitivity | specificity |
|---|---|---|---|---|---|---|---|---|---|---|---|---|---|---|
| Cupriavidus | 0.0157 | 0.0619 | 0.0000 | 0.0000 | 0.0382 | 0.00 | 0.98 | 0.95 | 0.90 | 1.00 | 0.92 | 0.90 | 0.87 | 0.93 |
| Paracoccus | 0.0025 | 0.0047 | 0.0001 | 0.0003 | 0.0000 | 0.03 | 0.93 | 0.81 | 0.82 | 0.80 | 0.90 | 0.72 | 0.60 | 0.86 |
| Methylobacterium | 0.0092 | 0.0301 | 0.0003 | 0.0008 | 0.0127 | 0.03 | 0.87 | 0.83 | 0.89 | 0.76 | 0.90 | 0.83 | 0.80 | 0.86 |
| Citrobacter | 0.0025 | 0.0044 | 0.0001 | 0.0003 | 0.0000 | 0.05 | 0.92 | 0.80 | 0.82 | 0.78 | 0.86 | 0.79 | 0.73 | 0.86 |
| Halomonas | 0.0011 | 0.0032 | 0.0001 | 0.0003 | 0.0115 | 0.10 | 0.86 | 0.78 | 0.82 | 0.75 | 0.88 | 0.83 | 0.87 | 0.79 |
| Bacillus | 0.0021 | 0.0038 | 0.0003 | 0.0005 | 0.0001 | 0.12 | 0.89 | 0.78 | 0.80 | 0.75 | 0.90 | 0.83 | 0.80 | 0.86 |
| Pseudomonas | 0.0322 | 0.0306 | 0.0042 | 0.0048 | 0.0000 | 0.13 | 0.95 | 0.87 | 0.89 | 0.85 | 0.94 | 0.83 | 0.73 | 0.93 |
| Micrococcus | 0.0022 | 0.0034 | 0.0003 | 0.0005 | 0.0000 | 0.14 | 0.89 | 0.79 | 0.84 | 0.75 | 0.90 | 0.79 | 0.80 | 0.79 |
| Enhydrobacter | 0.0066 | 0.0089 | 0.0010 | 0.0019 | 0.0000 | 0.15 | 0.90 | 0.78 | 0.79 | 0.78 | 0.93 | 0.83 | 0.80 | 0.86 |
| Proteus | 0.0010 | 0.0024 | 0.0002 | 0.0007 | 0.0053 | 0.16 | 0.86 | 0.81 | 0.87 | 0.75 | 0.85 | 0.83 | 0.93 | 0.71 |
| Neisseria | 0.0021 | 0.0048 | 0.0003 | 0.0010 | 0.0034 | 0.17 | 0.86 | 0.81 | 0.85 | 0.76 | 0.82 | 0.76 | 0.80 | 0.71 |
| Rothia | 0.0021 | 0.0032 | 0.0006 | 0.0012 | 0.0001 | 0.27 | 0.87 | 0.78 | 0.84 | 0.71 | 0.89 | 0.79 | 0.73 | 0.86 |
| Propionibacterium | 0.0034 | 0.0050 | 0.0011 | 0.0015 | 0.0003 | 0.33 | 0.88 | 0.80 | 0.87 | 0.73 | 0.89 | 0.83 | 0.80 | 0.86 |
| Staphylococcus | 0.0125 | 0.0260 | 0.0042 | 0.0048 | 0.0080 | 0.34 | 0.85 | 0.78 | 0.84 | 0.71 | 0.89 | 0.86 | 0.87 | 0.86 |
| Acinetobacter | 0.0147 | 0.0165 | 0.0054 | 0.0058 | 0.0000 | 0.36 | 0.88 | 0.77 | 0.80 | 0.73 | 0.88 | 0.86 | 0.87 | 0.86 |
| Corynebacterium | 0.0097 | 0.0164 | 0.0038 | 0.0050 | 0.0037 | 0.39 | 0.87 | 0.82 | 0.87 | 0.76 | 0.87 | 0.86 | 0.87 | 0.86 |
| Fusobacterium | 0.0016 | 0.0033 | 0.0007 | 0.0018 | 0.0416 | 0.44 | 0.83 | 0.80 | 0.87 | 0.73 | 0.87 | 0.86 | 0.93 | 0.79 |

TABLE 11-continued

| Genus | Normal individual Mean | SD | Ulcerative colitis Mean | SD | t-test p-value | Ratio | AUC | Training Set Accuracy | sensi-tivity | speci-ficity | AUC | Testing Set Accuracy | sensi-tivity | speci-ficity |
|---|---|---|---|---|---|---|---|---|---|---|---|---|---|---|
| *Streptococcus* | 0.0150 | 0.0180 | 0.0323 | 0.0662 | 0.0401 | 2.15 | 0.83 | 0.82 | 0.89 | 0.75 | 0.85 | 0.86 | 0.93 | 0.79 |
| *Rhodococcus* | 0.0005 | 0.0007 | 0.0011 | 0.0021 | 0.0261 | 2.17 | 0.84 | 0.78 | 0.80 | 0.75 | 0.87 | 0.86 | 0.93 | 0.79 |
| *Klebsiella* | 0.0005 | 0.0010 | 0.0013 | 0.0030 | 0.0325 | 2.70 | 0.83 | 0.82 | 0.87 | 0.76 | 0.87 | 0.86 | 0.93 | 0.79 |
| *Blautia* | 0.0078 | 0.0190 | 0.0223 | 0.0294 | 0.0007 | 2.87 | 0.83 | 0.78 | 0.85 | 0.71 | 0.87 | 0.86 | 0.93 | 0.79 |
| *Peptoniphilus* | 0.0002 | 0.0014 | 0.0010 | 0.0027 | 0.0416 | 4.11 | 0.84 | 0.81 | 0.89 | 0.73 | 0.90 | 0.86 | 0.93 | 0.79 |
| *Bifidobacterium* | 0.0118 | 0.0124 | 0.0505 | 0.1112 | 0.0057 | 4.28 | 0.86 | 0.81 | 0.90 | 0.71 | 0.92 | 0.83 | 0.87 | 0.79 |
| *Coprococcus* | 0.0032 | 0.0035 | 0.0138 | 0.0167 | 0.0000 | 4.29 | 0.89 | 0.87 | 0.92 | 0.82 | 0.93 | 0.83 | 0.87 | 0.79 |
| [*Eubacterium*] | 0.0009 | 0.0016 | 0.0043 | 0.0080 | 0.0008 | 4.87 | 0.84 | 0.78 | 0.84 | 0.73 | 0.91 | 0.83 | 0.87 | 0.79 |
| *Dorea* | 0.0013 | 0.0029 | 0.0067 | 0.0101 | 0.0001 | 5.22 | 0.86 | 0.81 | 0.89 | 0.73 | 0.90 | 0.86 | 0.93 | 0.79 |
| *Collinsella* | 0.0032 | 0.0059 | 0.0231 | 0.0402 | 0.0001 | 7.25 | 0.91 | 0.86 | 0.92 | 0.80 | 0.99 | 0.90 | 1.00 | 0.79 |
| *Stenotrophomonas* | 0.0004 | 0.0014 | 0.0032 | 0.0050 | 0.0000 | 7.59 | 0.86 | 0.85 | 0.95 | 0.75 | 0.95 | 0.76 | 0.87 | 0.64 |

Example 6. Crohn's Disease Diagnostic Model Based on Metagenomic Analysis of Bacteria Isolated from Stool of Normal Individual and Crohn's Disease Patient Bacteria was isolated from stool samples of 40 Crohn's disease patients and 76 normal individuals, the two groups matched in age and gender, and then metagenomic sequencing was performed thereon using the method of Example 3. For the development of a diagnostic model, first, a strain exhibiting a p value of less than 0.05 between two groups in a t-test and a difference of two-fold or more between two groups was selected, and then an area under curve (AUC), sensitivity, and specificity, which are diagnostic performance indexes, were calculated by logistic regression analysis.

Figure 12:
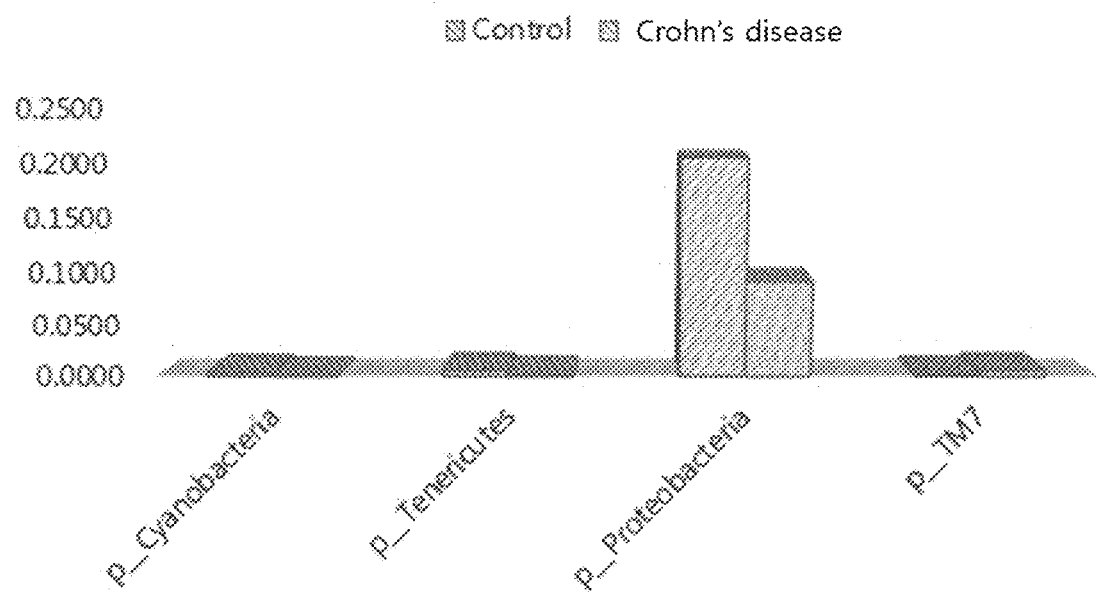
FIG. 12 is a result showing the distribution of bacteria, which is significant in diagnostic performance at the phylum level by isolating bacteria from stool of a patient with Crohn's disease and a normal individual, and then performing a metagenomic analysis.

As a result of analyzing bacteria in stool at a phylum level, a diagnostic model developed using bacteria belonging to the phylum Cyanobacteria, the phylum Tenericutes, the phylum Proteobacteria, and the phylum TM7 as a biomarker exhibited significant diagnostic performance for Crohn's disease (see Table 12 and FIG. 12).

TABLE 12

| Phylum | Normal individual Mean | SD | Crohn's disease Mean | SD | t-test p-value | Ratio | AUC | Training Set Accuracy | sensi-tivity | speci-ficity | AUC | Testing Set Accuracy | sensi-tivity | speci-ficity |
|---|---|---|---|---|---|---|---|---|---|---|---|---|---|---|
| Cyanobacteria | 0.0034 | 0.0072 | 0.0002 | 0.0007 | 0.0003 | 0.07 | 0.98 | 0.96 | 0.98 | 0.90 | 1.00 | 1.00 | 1.00 | 1.00 |
| Tenericutes | 0.0049 | 0.0094 | 0.0013 | 0.0052 | 0.0115 | 0.27 | 0.97 | 0.95 | 0.98 | 0.87 | 1.00 | 1.00 | 1.00 | 1.00 |
| Proteobacteria | 0.2047 | 0.2231 | 0.0903 | 0.0992 | 0.0003 | 0.44 | 0.97 | 0.95 | 1.00 | 0.84 | 1.00 | 1.00 | 1.00 | 1.00 |
| TM7 | 0.0015 | 0.0038 | 0.0050 | 0.0105 | 0.0497 | 3.29 | 0.97 | 0.95 | 0.98 | 0.87 | 1.00 | 1.00 | 1.00 | 1.00 |

Figure 13:
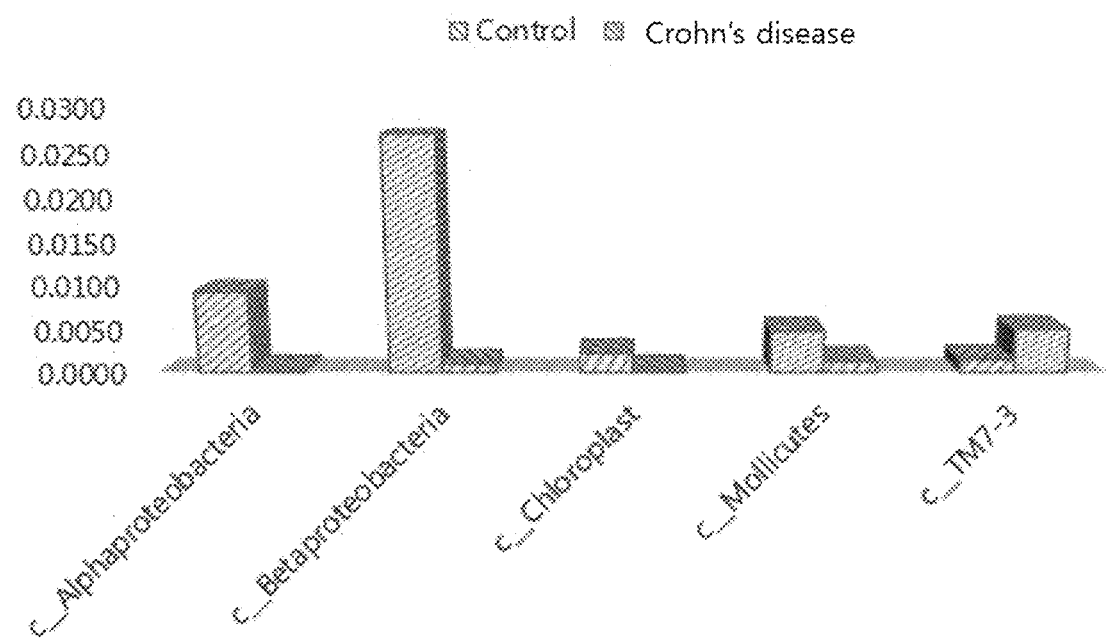
FIG. 13 is a result showing the distribution of bacteria, which is significant in diagnostic performance at the class level by isolating bacteria from stool of a patient with Crohn's disease and a normal individual, and then performing a metagenomic analysis.

As a result of analyzing bacteria in stool at a class level, a diagnostic model developed using bacteria belonging to the class Alphaproteobacteria, the class Betaproteobacteria, the class Chloroplast, the class Mollicutes, and the class TM7-3 as a biomarker exhibited significant diagnostic performance for Crohn's disease (see Table 13 and FIG. 13).

TABLE 13

| Class | Normal individual Mean | SD | Crohn's disease Mean | SD | t-test p-value | Ratio | AUC | Training Set Accuracy | sensi-tivity | speci-ficity | AUC | Testing Set Accuracy | sensi-tivity | speci-ficity |
|---|---|---|---|---|---|---|---|---|---|---|---|---|---|---|
| Alphaproteobacteria | 0.0093 | 0.0230 | 0.0002 | 0.0010 | 0.0010 | 0.03 | 0.98 | 0.97 | 1.00 | 0.90 | 1.00 | 1.00 | 1.00 | 1.00 |
| Betaproteobacteria | 0.0270 | 0.0638 | 0.0009 | 0.0021 | 0.0007 | 0.04 | 0.98 | 0.97 | 1.00 | 0.90 | 1.00 | 1.00 | 1.00 | 1.00 |
| Chloroplast | 0.0022 | 0.0054 | 0.0002 | 0.0007 | 0.0023 | 0.10 | 0.97 | 0.97 | 1.00 | 0.90 | 1.00 | 1.00 | 1.00 | 1.00 |
| Mollicutes | 0.0048 | 0.0094 | 0.0013 | 0.0052 | 0.0117 | 0.27 | 0.97 | 0.95 | 0.98 | 0.87 | 1.00 | 1.00 | 1.00 | 1.00 |
| TM7-3 | 0.0015 | 0.0038 | 0.0050 | 0.0105 | 0.0470 | 3.39 | 0.97 | 0.95 | 0.98 | 0.87 | 1.00 | 1.00 | 1.00 | 1.00 |

Figure 14:
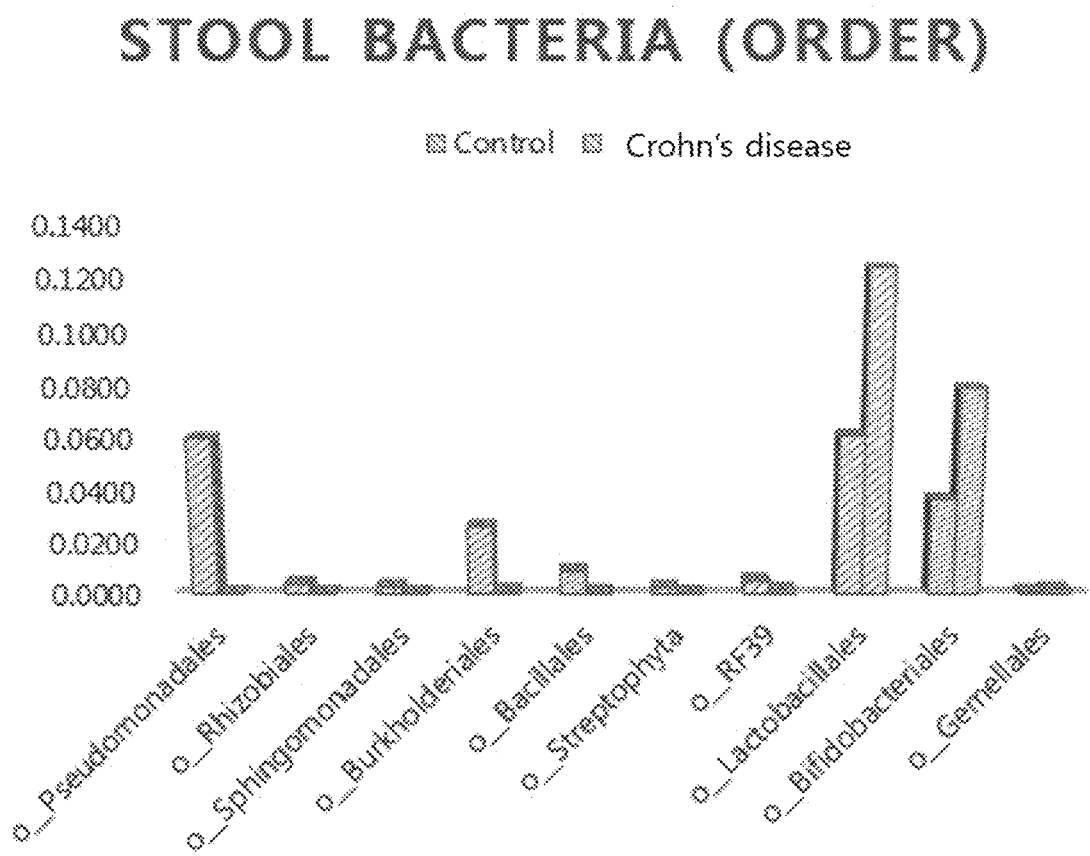
FIG. 14 is a result showing the distribution of bacteria, which is significant in diagnostic performance at the order level by isolating bacteria from stool of a patient with Crohn's disease and a normal individual, and then performing a metagenomic analysis.

As a result of analyzing bacteria in stool at an order level, a diagnostic model developed using bacteria belonging to the order Pseudomonadales, the order Rhizobiales, the order Sphingomonadales, the order Burkholderiales, the order Bacillales, the order Streptophyta, the order RF39, the order Lactobacillales, the order Bifidobacteriales, and the order Gemellales as a biomarker exhibited significant diagnostic performance for Crohn's disease (see Table 14 and FIG. 14).

TABLE 14

| Order | Normal individual Mean | SD | Crohn's disease Mean | SD | t-test p-value | Ratio | AUC | Training Set Accuracy | sensitivity | specificity | AUC | Testing Set Accuracy | sensitivity | specificity |
|---|---|---|---|---|---|---|---|---|---|---|---|---|---|---|
| Pseudomonadales | 0.0601 | 0.1633 | 0.0000 | 0.0000 | 0.0021 | 0.00 | 0.99 | 0.95 | 0.97 | 0.90 | 1.00 | 1.00 | 1.00 | 1.00 |
| Rhizobiales | 0.0037 | 0.0102 | 0.0000 | 0.0000 | 0.0024 | 0.00 | 0.99 | 0.96 | 0.98 | 0.90 | 0.93 | 0.96 | 1.00 | 0.89 |
| Sphingomonadales | 0.0025 | 0.0080 | 0.0000 | 0.0000 | 0.0099 | 0.01 | 0.98 | 0.93 | 0.98 | 0.84 | 1.00 | 1.00 | 1.00 | 1.00 |
| Burkholderiales | 0.0261 | 0.0634 | 0.0009 | 0.0021 | 0.0009 | 0.03 | 0.98 | 0.97 | 1.00 | 0.90 | 1.00 | 1.00 | 1.00 | 1.00 |
| Bacillales | 0.0088 | 0.0282 | 0.0004 | 0.0006 | 0.0116 | 0.04 | 0.98 | 0.97 | 1.00 | 0.90 | 1.00 | 1.00 | 1.00 | 1.00 |
| Streptophyta | 0.0022 | 0.0053 | 0.0002 | 0.0007 | 0.0022 | 0.10 | 0.97 | 0.97 | 1.00 | 0.90 | 1.00 | 1.00 | 1.00 | 1.00 |
| RF39 | 0.0048 | 0.0094 | 0.0013 | 0.0052 | 0.0117 | 0.28 | 0.97 | 0.95 | 0.98 | 0.87 | 1.00 | 1.00 | 1.00 | 1.00 |
| Lactobacillales | 0.0612 | 0.0798 | 0.1238 | 0.1647 | 0.0296 | 2.02 | 0.96 | 0.93 | 0.98 | 0.84 | 1.00 | 1.00 | 1.00 | 1.00 |
| Bifidobacteriales | 0.0367 | 0.0507 | 0.0790 | 0.0855 | 0.0063 | 2.15 | 0.97 | 0.97 | 1.00 | 0.90 | 1.00 | 1.00 | 1.00 | 1.00 |
| Gemellales | 0.0005 | 0.0014 | 0.0014 | 0.0028 | 0.0497 | 3.00 | 0.97 | 0.95 | 1.00 | 0.84 | 1.00 | 1.00 | 1.00 | 1.00 |

Figure 15:
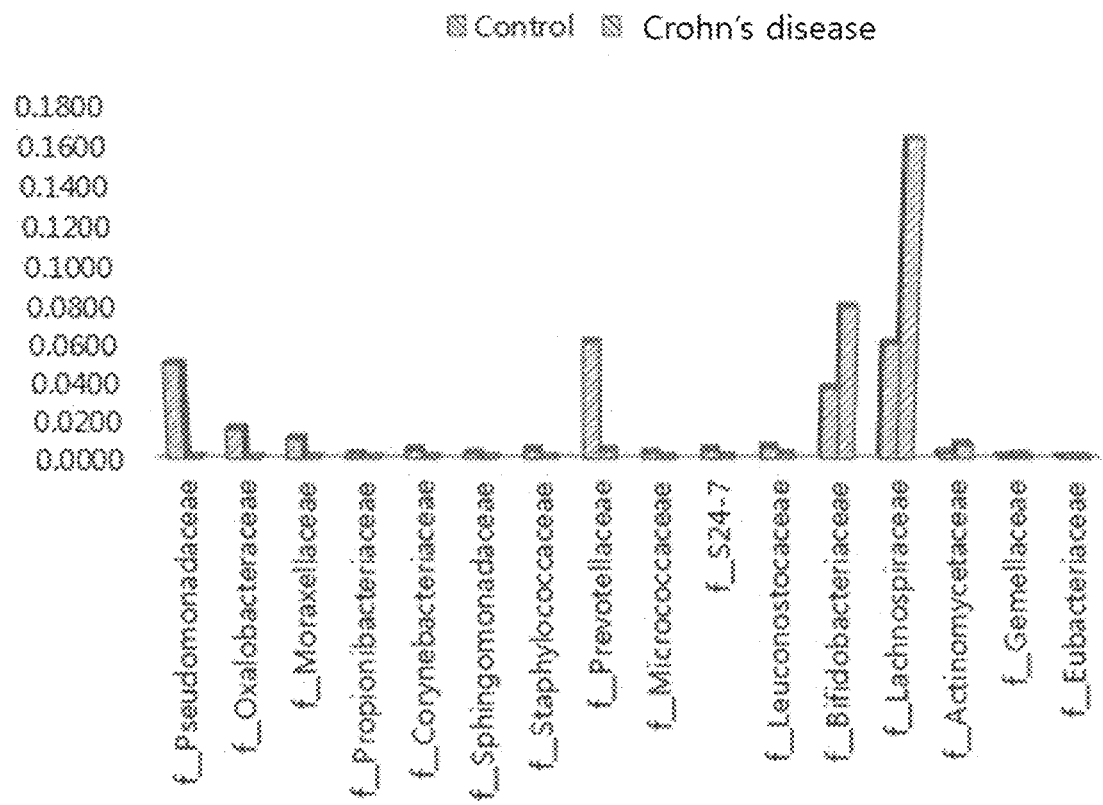
FIG. 15 is a result showing the distribution of bacteria, which is significant in diagnostic performance at the family level by isolating bacteria from stool of a patient with Crohn's disease and a normal individual, and then performing a metagenomic analysis.

As a result of analyzing bacteria in stool at a family level, a diagnostic model developed using bacteria belonging to the family Pseudomonadaceae, the family Oxalobacteraceae, the family Moraxellaceae, the family Propionibacteriaceae, the family Corynebacteriaceae, the family Sphingomonadaceae, the family Staphylococcaceae, the family Prevotellaceae, the family Micrococcaceae, the family 524-7, the family Leuconostocaceae, the family Bifidobacteriaceae, the family Lachnospiraceae, the family Actinomycetaceae, the family Gemellaceae, and the family Eubacteriaceae as a biomarker exhibited significant diagnostic performance for Crohn's disease (see Table 15 and FIG. 15).

TABLE 15

| Family | Normal individual Mean | SD | Crohn's disease Mean | SD | t-test p-value | Ratio | AUC | Training Set Accuracy | sensitivity | specificity | AUC | Testing Set Accuracy | sensitivity | specificity |
|---|---|---|---|---|---|---|---|---|---|---|---|---|---|---|
| Pseudomonadaceae | 0.0498 | 0.1541 | 0.0000 | 0.0000 | 0.0066 | 0.00 | 0.99 | 0.95 | 0.97 | 0.90 | 1.00 | 1.00 | 1.00 | 1.00 |
| Oxalobacteraceae | 0.0157 | 0.0451 | 0.0000 | 0.0000 | 0.0034 | 0.00 | 0.99 | 0.95 | 0.97 | 0.90 | 1.00 | 0.96 | 0.93 | 1.00 |
| Moraxellaceae | 0.0102 | 0.0289 | 0.0000 | 0.0000 | 0.0030 | 0.00 | 0.99 | 0.96 | 0.98 | 0.90 | 1.00 | 1.00 | 1.00 | 1.00 |
| Propionibacteriaceae | 0.0018 | 0.0056 | 0.0000 | 0.0000 | 0.0062 | 0.00 | 0.98 | 0.97 | 1.00 | 0.90 | 1.00 | 1.00 | 1.00 | 1.00 |
| Corynebacteriaceae | 0.0043 | 0.0138 | 0.0000 | 0.0001 | 0.0084 | 0.01 | 0.98 | 0.97 | 1.00 | 0.90 | 1.00 | 1.00 | 1.00 | 1.00 |
| Sphingomonadaceae | 0.0024 | 0.0075 | 0.0000 | 0.0000 | 0.0085 | 0.01 | 0.98 | 0.93 | 0.98 | 0.84 | 1.00 | 1.00 | 1.00 | 1.00 |
| Staphylococcaceae | 0.0041 | 0.0122 | 0.0000 | 0.0001 | 0.0053 | 0.01 | 0.98 | 0.97 | 1.00 | 0.90 | 1.00 | 1.00 | 1.00 | 1.00 |
| Prevotellaceae | 0.0608 | 0.0848 | 0.0039 | 0.0082 | 0.0000 | 0.06 | 0.98 | 0.96 | 0.98 | 0.90 | 1.00 | 1.00 | 1.00 | 1.00 |
| Micrococcaceae | 0.0025 | 0.0066 | 0.0002 | 0.0002 | 0.0036 | 0.09 | 0.97 | 0.96 | 1.00 | 0.87 | 1.00 | 1.00 | 1.00 | 1.00 |
| S24-7 | 0.0043 | 0.0107 | 0.0006 | 0.0028 | 0.0068 | 0.14 | 0.97 | 0.95 | 0.98 | 0.87 | 1.00 | 1.00 | 1.00 | 1.00 |
| Leuconostocaceae | 0.0057 | 0.0151 | 0.0020 | 0.0026 | 0.0423 | 0.35 | 0.97 | 0.96 | 1.00 | 0.87 | 1.00 | 1.00 | 1.00 | 1.00 |
| Bifidobacteriaceae | 0.0367 | 0.0507 | 0.0790 | 0.0855 | 0.0063 | 2.15 | 0.97 | 0.97 | 1.00 | 0.90 | 1.00 | 1.00 | 1.00 | 1.00 |
| Lachnospiraceae | 0.0603 | 0.0376 | 0.1635 | 0.1208 | 0.0000 | 2.71 | 0.97 | 0.97 | 1.00 | 0.90 | 1.00 | 1.00 | 1.00 | 1.00 |
| Actinomycetaceae | 0.0025 | 0.0036 | 0.0073 | 0.0101 | 0.0065 | 2.91 | 0.97 | 0.96 | 1.00 | 0.87 | 1.00 | 1.00 | 1.00 | 1.00 |
| Gemellaceae | 0.0005 | 0.0014 | 0.0014 | 0.0027 | 0.0481 | 3.02 | 0.97 | 0.95 | 1.00 | 0.84 | 1.00 | 1.00 | 1.00 | 1.00 |
| Eubacteriaceae | 0.0000 | 0.0001 | 0.0005 | 0.0013 | 0.0179 | 18.89 | 0.99 | 0.96 | 1.00 | 0.87 | 1.00 | 1.00 | 1.00 | 1.00 |

Figure 16:
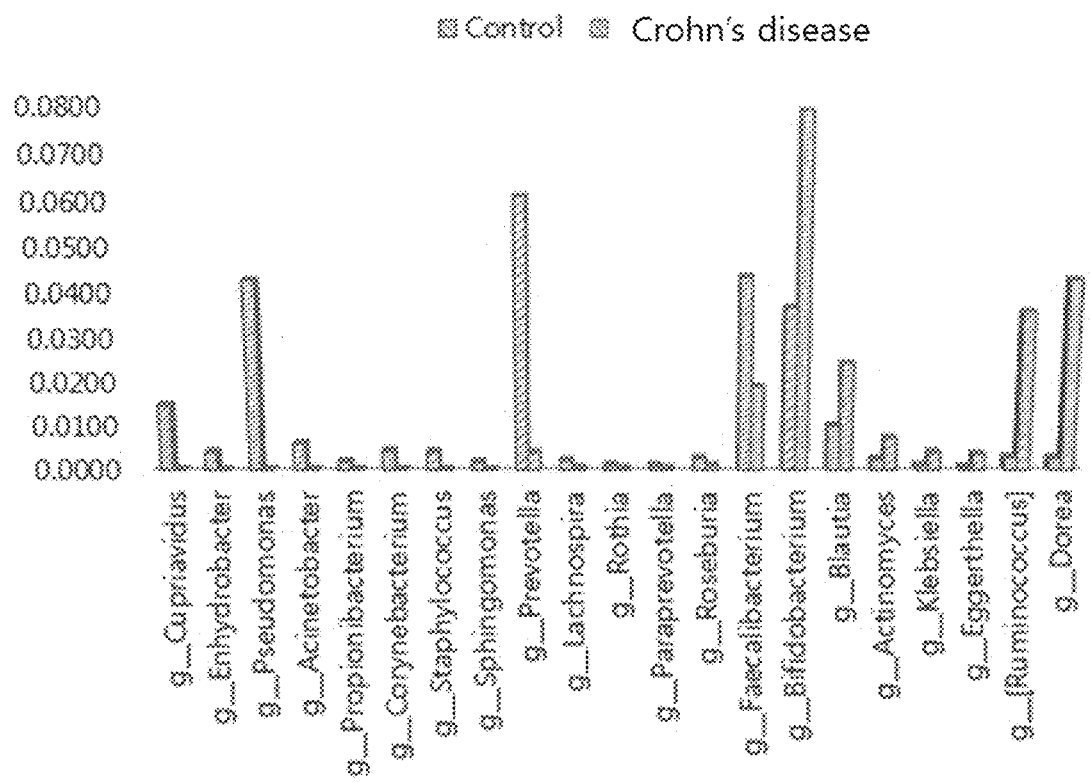
FIG. 16 is a result showing the distribution of bacteria, which is significant in diagnostic performance at the genus level by isolating bacteria from stool of a patient with Crohn's disease and a normal individual, and then performing a metagenomic analysis.

As a result of analyzing bacteria in stool at a genus level, a diagnostic model developed using bacteria belonging to the genus *Cupriavidus*, the genus *Enhydrobacter*, the genus *Pseudomonas*, the genus *Acinetobacter*, the genus *Propionibacterium*, the genus *Corynebacterium*, the genus *Staphylococcus*, the genus *Sphingomonas*, the genus *Prevotella*, the genus *Lachnospira*, the genus *Rothia*, the genus *Paraprevotella*, the genus *Roseburia*, the genus *Faecalibacterium*, the genus *Bifidobacterium*, the genus *Blautia*, the genus *Actinomyces*, the genus *Klebsiella*, the genus *Eggerthella*, the genus *Ruminococcus*, and the genus *Dorea* as a biomarker exhibited significant diagnostic performance for Crohn's disease (see Table 16 and FIG. 16).

TABLE 16

| | Normal individual | | Crohn's disease | | t-test | | | Training Set | | | | Testing Set | | | |
|---|---|---|---|---|---|---|---|---|---|---|---|---|---|---|---|
| Genus | Mean | SD | Mean | SD | p-value | Ratio | AUC | Accuracy | sensitivity | specificity | AUC | Accuracy | sensitivity | specificity |
| *Cupriavidus* | 0.0147 | 0.0438 | 0.0000 | 0.0000 | 0.0376 | 0.00 | 0.99 | 0.95 | 0.97 | 0.90 | 1.00 | 0.96 | 0.93 | 1.00 |
| *Enhydrobacter* | 0.0040 | 0.0164 | 0.0000 | 0.0000 | 0.0385 | 0.00 | 0.98 | 0.95 | 0.97 | 0.90 | 1.00 | 1.00 | 1.00 | 1.00 |
| *Pseudomonas* | 0.0425 | 0.1427 | 0.0000 | 0.0000 | 0.0119 | 0.00 | 0.99 | 0.93 | 0.95 | 0.90 | 1.00 | 1.00 | 1.00 | 1.00 |
| *Acinetobacter* | 0.0061 | 0.0176 | 0.0000 | 0.0000 | 0.0040 | 0.00 | 0.99 | 0.95 | 0.98 | 0.87 | 1.00 | 1.00 | 1.00 | 1.00 |
| *Propionibacterium* | 0.0018 | 0.0056 | 0.0000 | 0.0000 | 0.0062 | 0.00 | 0.98 | 0.97 | 1.00 | 0.90 | 1.00 | 1.00 | 1.00 | 1.00 |
| *Corynebacterium* | 0.0043 | 0.0138 | 0.0000 | 0.0001 | 0.0084 | 0.01 | 0.98 | 0.97 | 1.00 | 0.90 | 1.00 | 1.00 | 1.00 | 1.00 |
| *Staphylococcus* | 0.0041 | 0.0121 | 0.0000 | 0.0001 | 0.0053 | 0.01 | 0.98 | 0.97 | 1.00 | 0.90 | 1.00 | 1.00 | 1.00 | 1.00 |
| *Sphingomonas* | 0.0017 | 0.0052 | 0.0000 | 0.0000 | 0.0056 | 0.01 | 0.98 | 0.95 | 1.00 | 0.84 | 1.00 | 1.00 | 1.00 | 1.00 |
| *Prevotella* | 0.0608 | 0.0847 | 0.0039 | 0.0082 | 0.0000 | 0.06 | 0.98 | 0.96 | 0.98 | 0.90 | 1.00 | 1.00 | 1.00 | 1.00 |
| *Lachnospira* | 0.0020 | 0.0033 | 0.0004 | 0.0008 | 0.0001 | 0.18 | 0.97 | 0.95 | 0.98 | 0.87 | 1.00 | 1.00 | 1.00 | 1.00 |
| *Rothia* | 0.0011 | 0.0027 | 0.0002 | 0.0002 | 0.0092 | 0.20 | 0.97 | 0.93 | 0.98 | 0.84 | 1.00 | 1.00 | 1.00 | 1.00 |
| *Paraprevotella* | 0.0009 | 0.0021 | 0.0003 | 0.0010 | 0.0292 | 0.30 | 0.97 | 0.95 | 1.00 | 0.84 | 1.00 | 1.00 | 1.00 | 1.00 |
| *Roseburia* | 0.0026 | 0.0057 | 0.0010 | 0.0016 | 0.0252 | 0.38 | 0.97 | 0.95 | 1.00 | 0.84 | 1.00 | 1.00 | 1.00 | 1.00 |
| *Faecalibacterium* | 0.0432 | 0.0478 | 0.0189 | 0.0332 | 0.0020 | 0.44 | 0.98 | 0.96 | 0.98 | 0.90 | 1.00 | 1.00 | 1.00 | 1.00 |
| *Bifidobacterium* | 0.0364 | 0.0507 | 0.0789 | 0.0855 | 0.0060 | 2.17 | 0.96 | 0.97 | 1.00 | 0.90 | 1.00 | 1.00 | 1.00 | 1.00 |
| *Blautia* | 0.0100 | 0.0118 | 0.0241 | 0.0218 | 0.0004 | 2.42 | 0.97 | 0.96 | 1.00 | 0.87 | 1.00 | 1.00 | 1.00 | 1.00 |
| *Actinomyces* | 0.0024 | 0.0036 | 0.0072 | 0.0101 | 0.0061 | 2.98 | 0.97 | 0.96 | 1.00 | 0.87 | 1.00 | 1.00 | 1.00 | 1.00 |
| *Klebsiella* | 0.0010 | 0.0024 | 0.0039 | 0.0086 | 0.0461 | 3.78 | 0.97 | 0.95 | 1.00 | 0.84 | 1.00 | 1.00 | 1.00 | 1.00 |
| *Eggerthella* | 0.0006 | 0.0019 | 0.0037 | 0.0076 | 0.0179 | 5.86 | 0.99 | 0.95 | 0.98 | 0.87 | 0.98 | 0.96 | 0.93 | 1.00 |
| [*Ruminococcus*] | 0.0029 | 0.0039 | 0.0356 | 0.0475 | 0.0001 | 12.40 | 0.99 | 0.96 | 0.98 | 0.90 | 0.99 | 0.96 | 0.93 | 1.00 |
| *Dorea* | 0.0027 | 0.0031 | 0.0426 | 0.0788 | 0.0030 | 15.84 | 0.98 | 0.97 | 1.00 | 0.90 | 1.00 | 1.00 | 1.00 | 1.00 |

Example 7. Crohn's Disease Diagnostic Model Based on Metagenomic Analysis of Bacteria-Derived Vesicles Isolated from Stool of Normal Individual and Crohn's Disease Patient Bacteria-derived vesicles were isolated from stool samples of 40 Crohn's disease patients and 76 normal individuals, the two groups matched in age and gender, and then metagenomic sequencing was performed thereon using the method of Example 3. For the development of a diagnostic model, first, a strain exhibiting a p value of less than 0.05 between two groups in a t-test and a difference of two-fold or more between two groups was selected, and then an area under curve (AUC), sensitivity, and specificity, which are diagnostic performance indexes, were calculated by logistic regression analysis.

Figure 17:
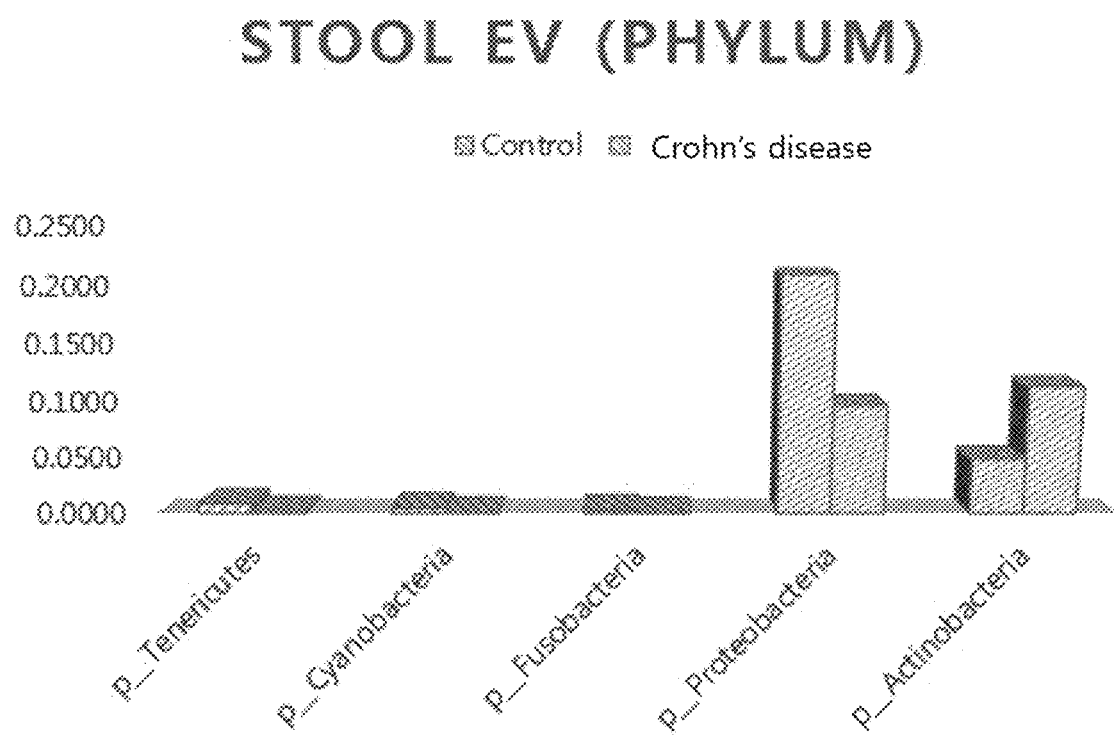
FIG. 17 is a result showing the distribution of bacteria-derived vesicles (EVs), which is significant in diagnostic performance at the phylum level by isolating bacteria-derived vesicles from stool of a patient with Crohn's disease and a normal individual, and then performing a metagenomic analysis.

As a result of analyzing vesicles derived from bacteria in stool at a phylum level, a diagnostic model developed using vesicles derived from bacteria belonging to the phylum Tenericutes, the phylum Cyanobacteria, the phylum Fusobacteria, the phylum Proteobacteria, and the phylum Actinobacteria as a biomarker exhibited significant diagnostic performance for Crohn's disease (see Table 17 and FIG. 17).

TABLE 17

| | Normal individual | | Crohn's disease | | t-test | | | Training Set | | | | Testing Set | | | |
|---|---|---|---|---|---|---|---|---|---|---|---|---|---|---|---|
| Phylum | Mean | SD | Mean | SD | p-value | Ratio | AUC | Accuracy | sensitivity | specificity | AUC | Accuracy | sensitivity | specificity |
| Tenericutes | 0.0086 | 0.0286 | 0.0012 | 0.0033 | 0.0299 | 0.14 | 0.96 | 0.95 | 1.00 | 0.84 | 1.00 | 1.00 | 1.00 | 1.00 |
| Cyanobacteria | 0.0046 | 0.0066 | 0.0008 | 0.0020 | 0.0000 | 0.18 | 0.99 | 0.96 | 0.98 | 0.90 | 1.00 | 1.00 | 1.00 | 1.00 |
| Fusobacteria | 0.0028 | 0.0062 | 0.0007 | 0.0015 | 0.0056 | 0.24 | 0.98 | 0.93 | 0.97 | 0.87 | 1.00 | 1.00 | 1.00 | 1.00 |

TABLE 17-continued

| Phylum | Normal individual Mean | Normal individual SD | Crohn's disease Mean | Crohn's disease SD | t-test p-value | Ratio | AUC | Training Set Accuracy | Training Set sensitivity | Training Set specificity | AUC | Testing Set Accuracy | Testing Set sensitivity | Testing Set specificity |
|---|---|---|---|---|---|---|---|---|---|---|---|---|---|---|
| Proteobacteria | 0.2071 | 0.1832 | 0.0951 | 0.0960 | 0.0000 | 0.46 | 0.97 | 0.95 | 1.00 | 0.84 | 1.00 | 1.00 | 1.00 | 1.00 |
| Actinobacteria | 0.0480 | 0.0478 | 0.1116 | 0.0804 | 0.0000 | 2.33 | 0.98 | 0.93 | 0.98 | 0.84 | 1.00 | 1.00 | 1.00 | 1.00 |

Figure 18:
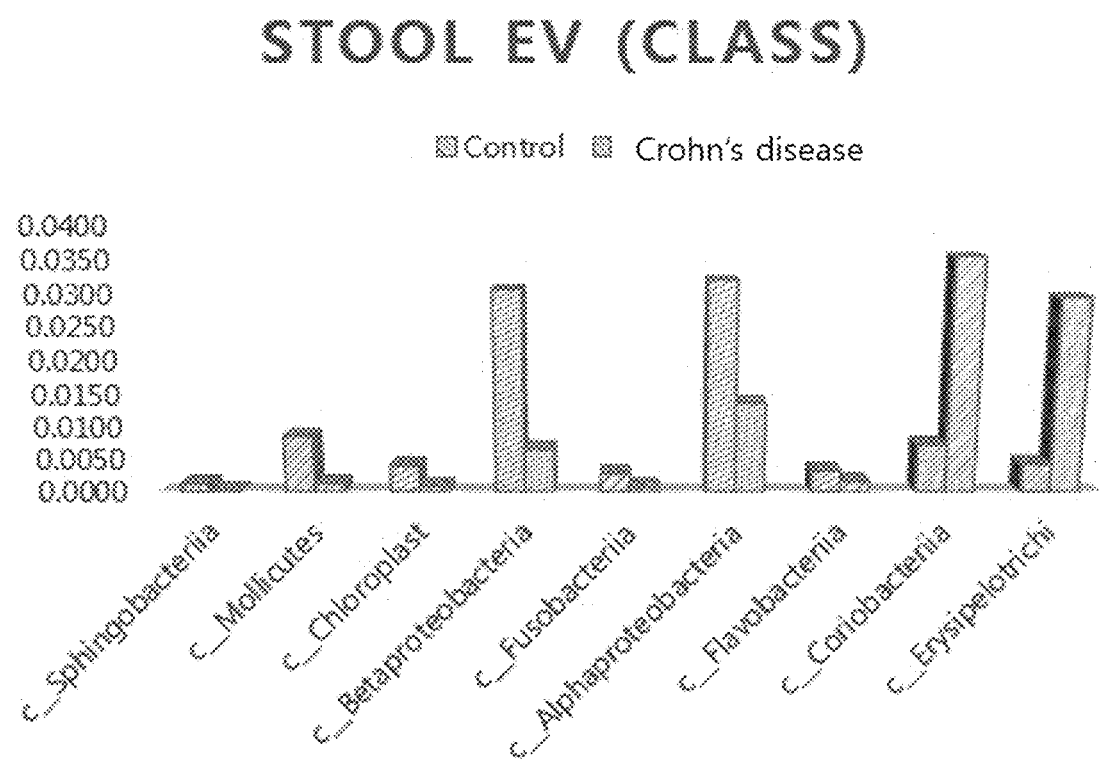
FIG. 18 is a result showing the distribution of bacteria-derived vesicles (EVs), which is significant in diagnostic performance at the class level by isolating bacteria-derived vesicles from stool of a patient with Crohn's disease and a normal individual, and then performing a metagenomic analysis.

As a result of analyzing vesicles derived from bacteria in stool at a class level, a diagnostic model developed using vesicles derived from bacteria belonging to the class Sphingobacteriia, the class Mollicutes, the class Chloroplast, the class Betaproteobacteria, the class Fusobacteriia, the class Alphaproteobacteria, the class Flavobacteriia, the class Coriobacteria, and the class Erysipelotrichi as a biomarker exhibited significant diagnostic performance for Crohn's disease (see Table 18 and FIG. 18).

TABLE 18

| Class | Normal individual Mean | Normal individual SD | Crohn's disease Mean | Crohn's disease SD | t-test p-value | Ratio | AUC | Training Set Accuracy | Training Set sensitivity | Training Set specificity | AUC | Testing Set Accuracy | Testing Set sensitivity | Testing Set specificity |
|---|---|---|---|---|---|---|---|---|---|---|---|---|---|---|
| Sphingobacteriia | 0.0012 | 0.0021 | 0.0001 | 0.0003 | 0.0000 | 0.08 | 0.98 | 0.96 | 0.98 | 0.90 | 1.00 | 1.00 | 1.00 | 1.00 |
| Mollicutes | 0.0085 | 0.0285 | 0.0012 | 0.0033 | 0.0318 | 0.14 | 0.96 | 0.95 | 1.00 | 0.84 | 1.00 | 1.00 | 1.00 | 1.00 |
| Chloroplast | 0.0040 | 0.0061 | 0.0008 | 0.0020 | 0.0001 | 0.19 | 0.99 | 0.96 | 0.98 | 0.90 | 1.00 | 1.00 | 1.00 | 1.00 |
| Betaproteobacteria | 0.0305 | 0.0666 | 0.0066 | 0.0138 | 0.0036 | 0.21 | 0.99 | 0.96 | 0.98 | 0.90 | 1.00 | 1.00 | 1.00 | 1.00 |
| Fusobacteriia | 0.0028 | 0.0062 | 0.0007 | 0.0015 | 0.0056 | 0.24 | 0.98 | 0.93 | 0.97 | 0.87 | 1.00 | 1.00 | 1.00 | 1.00 |
| Alphaproteobacteria | 0.0318 | 0.0415 | 0.0136 | 0.0178 | 0.0014 | 0.43 | 0.98 | 0.96 | 0.98 | 0.90 | 1.00 | 1.00 | 1.00 | 1.00 |
| Flavobacteriia | 0.0032 | 0.0048 | 0.0016 | 0.0022 | 0.0121 | 0.48 | 0.97 | 0.96 | 0.98 | 0.90 | 1.00 | 1.00 | 1.00 | 1.00 |
| Coriobacteriia | 0.0073 | 0.0131 | 0.0352 | 0.0301 | 0.0000 | 4.84 | 0.99 | 0.97 | 0.98 | 0.94 | 1.00 | 1.00 | 1.00 | 1.00 |
| Erysipelotrichi | 0.0043 | 0.0058 | 0.0293 | 0.0605 | 0.0137 | 6.88 | 0.98 | 0.93 | 0.98 | 0.84 | 1.00 | 1.00 | 1.00 | 1.00 |

Figure 19:
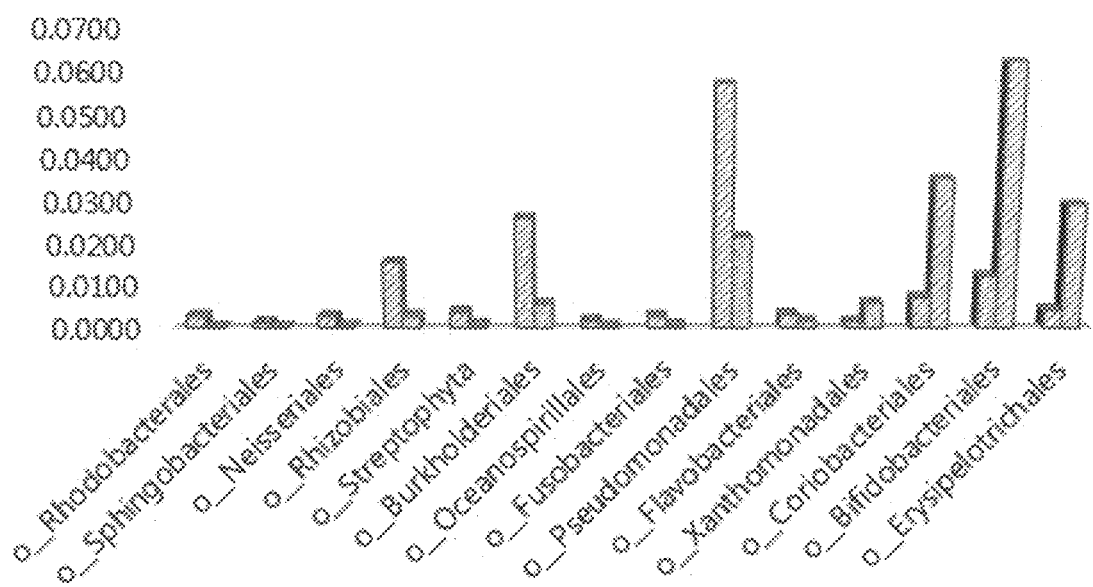
FIG. 19 is a result showing the distribution of bacteria-derived vesicles (EVs), which is significant in diagnostic performance at the order level by isolating bacteria-derived vesicles from stool of a patient with Crohn's disease and a normal individual, and then performing a metagenomic analysis.

As a result of analyzing vesicles derived from bacteria in stool at an order level, a diagnostic model developed using vesicles derived from bacteria belonging to the order Rhodobacterales, the order Sphingobacteriales, the order Neisseriales, the order Rhizobiales, the order Streptophyta, the order Burkholderiales, the order Oceanospirillales, the order Fusobacteriales, the order Pseudomonadales, the order Flavobacteriales, the order Xanthomonadales, the order Coriobacteriales, the order Bifidobacteriales, and the order Erysipelotrichales as a biomarker exhibited significant diagnostic performance for Crohn's disease (see Table 19 and FIG. 19).

TABLE 19

| Order | Normal individual Mean | Normal individual SD | Crohn's disease Mean | Crohn's disease SD | t-test p-value | Ratio | AUC | Training Set Accuracy | Training Set sensitivity | Training Set specificity | AUC | Testing Set Accuracy | Testing Set sensitivity | Testing Set specificity |
|---|---|---|---|---|---|---|---|---|---|---|---|---|---|---|
| Rhodobacterales | 0.0029 | 0.0048 | 0.0002 | 0.0005 | 0.0000 | 0.07 | 0.98 | 0.95 | 0.98 | 0.87 | 1.00 | 1.00 | 1.00 | 1.00 |
| Sphingobacteriales | 0.0012 | 0.0021 | 0.0001 | 0.0003 | 0.0000 | 0.08 | 0.98 | 0.96 | 0.98 | 0.90 | 1.00 | 1.00 | 1.00 | 1.00 |
| Neisseriales | 0.0028 | 0.0054 | 0.0005 | 0.0010 | 0.0005 | 0.17 | 0.98 | 0.95 | 0.98 | 0.87 | 1.00 | 1.00 | 1.00 | 1.00 |
| Rhizobiales | 0.0157 | 0.0312 | 0.0029 | 0.0033 | 0.0007 | 0.18 | 0.98 | 0.95 | 0.98 | 0.87 | 1.00 | 1.00 | 1.00 | 1.00 |
| Streptophyta | 0.0039 | 0.0061 | 0.0008 | 0.0020 | 0.0001 | 0.19 | 0.99 | 0.96 | 0.98 | 0.90 | 1.00 | 1.00 | 1.00 | 1.00 |
| Burkholderiales | 0.0262 | 0.0658 | 0.0058 | 0.0128 | 0.0111 | 0.22 | 0.98 | 0.96 | 0.98 | 0.90 | 1.00 | 1.00 | 1.00 | 1.00 |
| Oceanospirillales | 0.0016 | 0.0051 | 0.0004 | 0.0010 | 0.0413 | 0.23 | 0.98 | 0.96 | 0.98 | 0.90 | 0.90 | 0.96 | 1.00 | 0.89 |
| Fusobacteriales | 0.0028 | 0.0062 | 0.0007 | 0.0015 | 0.0056 | 0.24 | 0.98 | 0.93 | 0.97 | 0.87 | 1.00 | 1.00 | 1.00 | 1.00 |
| Pseudomonadales | 0.0571 | 0.0526 | 0.0216 | 0.0380 | 0.0001 | 0.38 | 0.97 | 0.95 | 1.00 | 0.84 | 1.00 | 1.00 | 1.00 | 1.00 |
| Flavobacteriales | 0.0032 | 0.0048 | 0.0016 | 0.0022 | 0.0121 | 0.48 | 0.97 | 0.96 | 0.98 | 0.90 | 1.00 | 1.00 | 1.00 | 1.00 |
| Xanthomonadales | 0.0014 | 0.0029 | 0.0059 | 0.0063 | 0.0001 | 4.17 | 0.98 | 0.96 | 1.00 | 0.87 | 1.00 | 1.00 | 1.00 | 1.00 |
| Coriobacteriales | 0.0073 | 0.0131 | 0.0352 | 0.0301 | 0.0000 | 4.84 | 0.99 | 0.97 | 0.98 | 0.94 | 1.00 | 1.00 | 1.00 | 1.00 |
| Bifidobacteriales | 0.0124 | 0.0126 | 0.0620 | 0.0513 | 0.0000 | 5.00 | 0.99 | 0.95 | 0.97 | 0.90 | 1.00 | 1.00 | 1.00 | 1.00 |
| Erysipelotrichales | 0.0043 | 0.0058 | 0.0293 | 0.0605 | 0.0137 | 6.88 | 0.98 | 0.93 | 0.98 | 0.84 | 1.00 | 1.00 | 1.00 | 1.00 |

Figure 20:
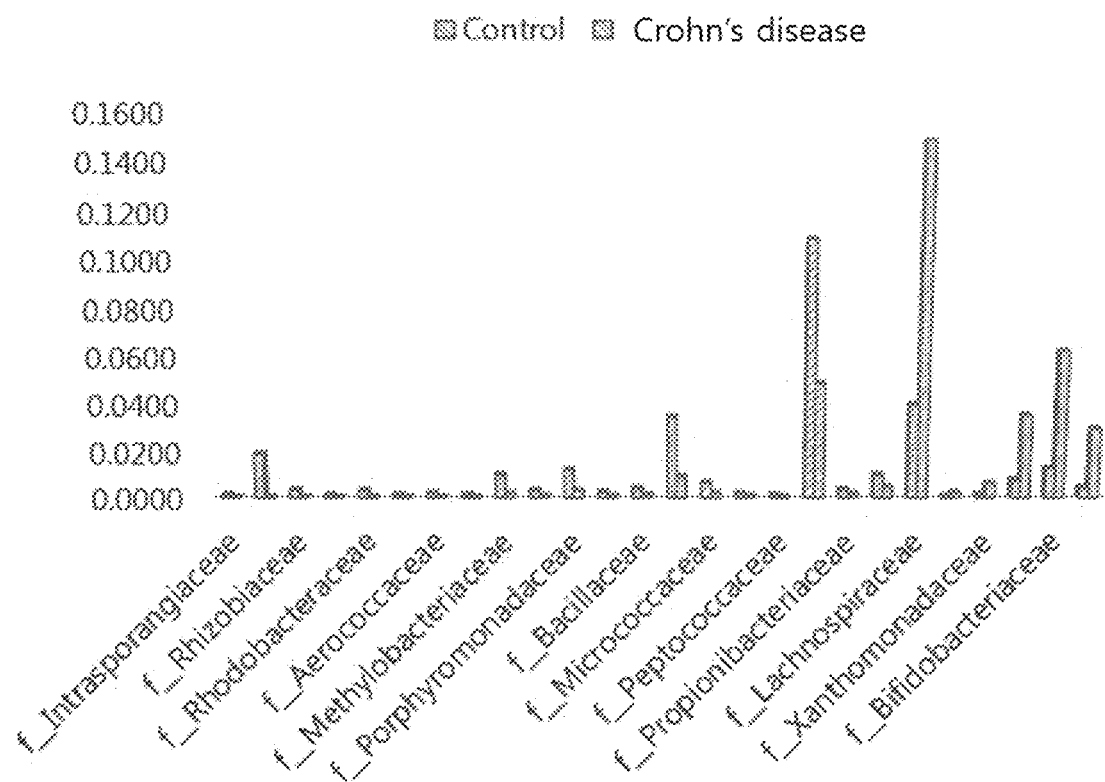
FIG. 20 is a result showing the distribution of bacteria-derived vesicles (EVs), which is significant in diagnostic performance at the family level by isolating bacteria-derived vesicles from stool of a patient with Crohn's disease and a normal individual, and then performing a metagenomic analysis.

As a result of analyzing vesicles derived from bacteria in stool at a family level, a diagnostic model developed using vesicles derived from bacteria belonging to the family Intrasporangiaceae, the family Oxalobacteraceae, the family Rhizobiaceae, the family Nocardioidaceae, the family Rhodobacteraceae, the family Sphingobacteriaceae, the family Aerococcaceae, the family Leptotrichiaceae, the family Methylobacteriaceae, the family Neisseriaceae, the family Porphyromonadaceae, the family Planococcaceae, the family Bacillaceae, the family Pseudomonadaceae, the family Micrococcaceae, the family Fusobacteriaceae, the family Peptococcaceae, the family Prevotellaceae, the family Propionibacteriaceae, the family Corynebacteriaceae, the family Lachnospiraceae, the family Nocardiaceae, the family Xanthomonadaceae, the family Coriobacteriaceae, the family Bifidobacteriaceae, and the family Erysipelotrichaceae as a biomarker exhibited significant diagnostic performance for Crohn's disease (see Table 20 and FIG. 20).

TABLE 20

| Family | Normal individual Mean | Normal individual SD | Crohn's disease Mean | Crohn's disease SD | t-test p-value | Ratio | Training Set AUC | Training Set Accuracy | Training Set sensitivity | Training Set specificity | Testing Set AUC | Testing Set Accuracy | Testing Set sensitivity | Testing Set specificity |
|---|---|---|---|---|---|---|---|---|---|---|---|---|---|---|
| Intrasporangiaceae | 0.0012 | 0.0021 | 0.0000 | 0.0001 | 0.0000 | 0.01 | 0.99 | 0.96 | 0.98 | 0.90 | 1.00 | 1.00 | 1.00 | 1.00 |
| Oxalobacteraceae | 0.0187 | 0.0635 | 0.0003 | 0.0008 | 0.0142 | 0.02 | 0.99 | 0.96 | 0.97 | 0.94 | 1.00 | 1.00 | 1.00 | 1.00 |
| Rhizobiaceae | 0.0032 | 0.0048 | 0.0001 | 0.0003 | 0.0000 | 0.03 | 0.99 | 0.96 | 0.98 | 0.90 | 1.00 | 1.00 | 1.00 | 1.00 |
| Nocardioidaceae | 0.0010 | 0.0032 | 0.0000 | 0.0002 | 0.0136 | 0.04 | 0.98 | 0.95 | 0.98 | 0.87 | 0.94 | 0.96 | 1.00 | 0.89 |
| Rhodobacteraceae | 0.0029 | 0.0048 | 0.0002 | 0.0005 | 0.0000 | 0.07 | 0.98 | 0.95 | 0.98 | 0.87 | 1.00 | 1.00 | 1.00 | 1.00 |
| Sphingobacteriaceae | 0.0011 | 0.0019 | 0.0001 | 0.0003 | 0.0000 | 0.09 | 0.98 | 0.95 | 0.98 | 0.87 | 1.00 | 1.00 | 1.00 | 1.00 |
| Aerococcaceae | 0.0018 | 0.0038 | 0.0002 | 0.0005 | 0.0005 | 0.12 | 0.98 | 0.95 | 0.98 | 0.87 | 1.00 | 1.00 | 1.00 | 1.00 |
| Leptotrichiaceae | 0.0012 | 0.0042 | 0.0001 | 0.0004 | 0.0405 | 0.13 | 0.98 | 0.96 | 0.98 | 0.90 | 1.00 | 1.00 | 1.00 | 1.00 |
| Methylobacteriaceae | 0.0099 | 0.0300 | 0.0016 | 0.0023 | 0.0196 | 0.16 | 0.98 | 0.95 | 0.98 | 0.87 | 1.00 | 1.00 | 1.00 | 1.00 |
| Neisseriaceae | 0.0028 | 0.0054 | 0.0005 | 0.0010 | 0.0005 | 0.17 | 0.98 | 0.95 | 0.98 | 0.87 | 1.00 | 1.00 | 1.00 | 1.00 |
| Porphyromonadaceae | 0.0116 | 0.0269 | 0.0026 | 0.0032 | 0.0054 | 0.23 | 0.97 | 0.95 | 0.98 | 0.87 | 1.00 | 1.00 | 1.00 | 1.00 |
| Planococcaceae | 0.0024 | 0.0035 | 0.0006 | 0.0011 | 0.0001 | 0.23 | 0.98 | 0.96 | 0.98 | 0.90 | 1.00 | 1.00 | 1.00 | 1.00 |
| Bacillaceae | 0.0038 | 0.0061 | 0.0010 | 0.0019 | 0.0004 | 0.26 | 0.98 | 0.96 | 0.98 | 0.90 | 1.00 | 1.00 | 1.00 | 1.00 |
| Pseudomonadaceae | 0.0345 | 0.0325 | 0.0090 | 0.0182 | 0.0000 | 0.26 | 0.97 | 0.95 | 0.98 | 0.87 | 1.00 | 1.00 | 1.00 | 1.00 |
| Micrococcaceae | 0.0062 | 0.0071 | 0.0019 | 0.0037 | 0.0000 | 0.30 | 0.99 | 0.96 | 0.98 | 0.90 | 1.00 | 1.00 | 1.00 | 1.00 |
| Fusobacteriaceae | 0.0016 | 0.0033 | 0.0005 | 0.0013 | 0.0128 | 0.31 | 0.97 | 0.95 | 0.98 | 0.87 | 1.00 | 1.00 | 1.00 | 1.00 |
| Peptococcaceae | 0.0010 | 0.0022 | 0.0003 | 0.0008 | 0.0298 | 0.35 | 0.97 | 0.96 | 1.00 | 0.87 | 1.00 | 1.00 | 1.00 | 1.00 |
| Prevotellaceae | 0.1083 | 0.1515 | 0.0485 | 0.1046 | 0.0152 | 0.45 | 0.97 | 0.96 | 1.00 | 0.87 | 1.00 | 1.00 | 1.00 | 1.00 |
| Propionibacteriaceae | 0.0034 | 0.0050 | 0.0016 | 0.0025 | 0.0093 | 0.46 | 0.99 | 0.96 | 0.98 | 0.90 | 1.00 | 1.00 | 1.00 | 1.00 |
| Corynebacteriaceae | 0.0097 | 0.0164 | 0.0045 | 0.0058 | 0.0149 | 0.46 | 0.98 | 0.96 | 0.98 | 0.90 | 1.00 | 1.00 | 1.00 | 1.00 |
| Lachnospiraceae | 0.0396 | 0.0324 | 0.1479 | 0.1350 | 0.0000 | 3.74 | 0.99 | 0.97 | 1.00 | 0.90 | 1.00 | 0.96 | 0.93 | 1.00 |
| Nocardiaceae | 0.0005 | 0.0007 | 0.0020 | 0.0041 | 0.0283 | 3.90 | 0.99 | 0.97 | 1.00 | 0.90 | 1.00 | 1.00 | 1.00 | 1.00 |
| Xanthomonadaceae | 0.0013 | 0.0027 | 0.0058 | 0.0062 | 0.0001 | 4.53 | 0.98 | 0.96 | 1.00 | 0.87 | 1.00 | 1.00 | 1.00 | 1.00 |
| Coriobacteriaceae | 0.0073 | 0.0131 | 0.0352 | 0.0301 | 0.0000 | 4.84 | 0.99 | 0.97 | 0.98 | 0.94 | 1.00 | 1.00 | 1.00 | 1.00 |
| Bifidobacteriaceae | 0.0124 | 0.0126 | 0.0620 | 0.0513 | 0.0000 | 5.00 | 0.99 | 0.95 | 0.97 | 0.90 | 1.00 | 1.00 | 1.00 | 1.00 |
| Erysipelotrichaceae | 0.0043 | 0.0058 | 0.0293 | 0.0605 | 0.0137 | 6.88 | 0.98 | 0.93 | 0.98 | 0.84 | 1.00 | 1.00 | 1.00 | 1.00 |

Figure 21:
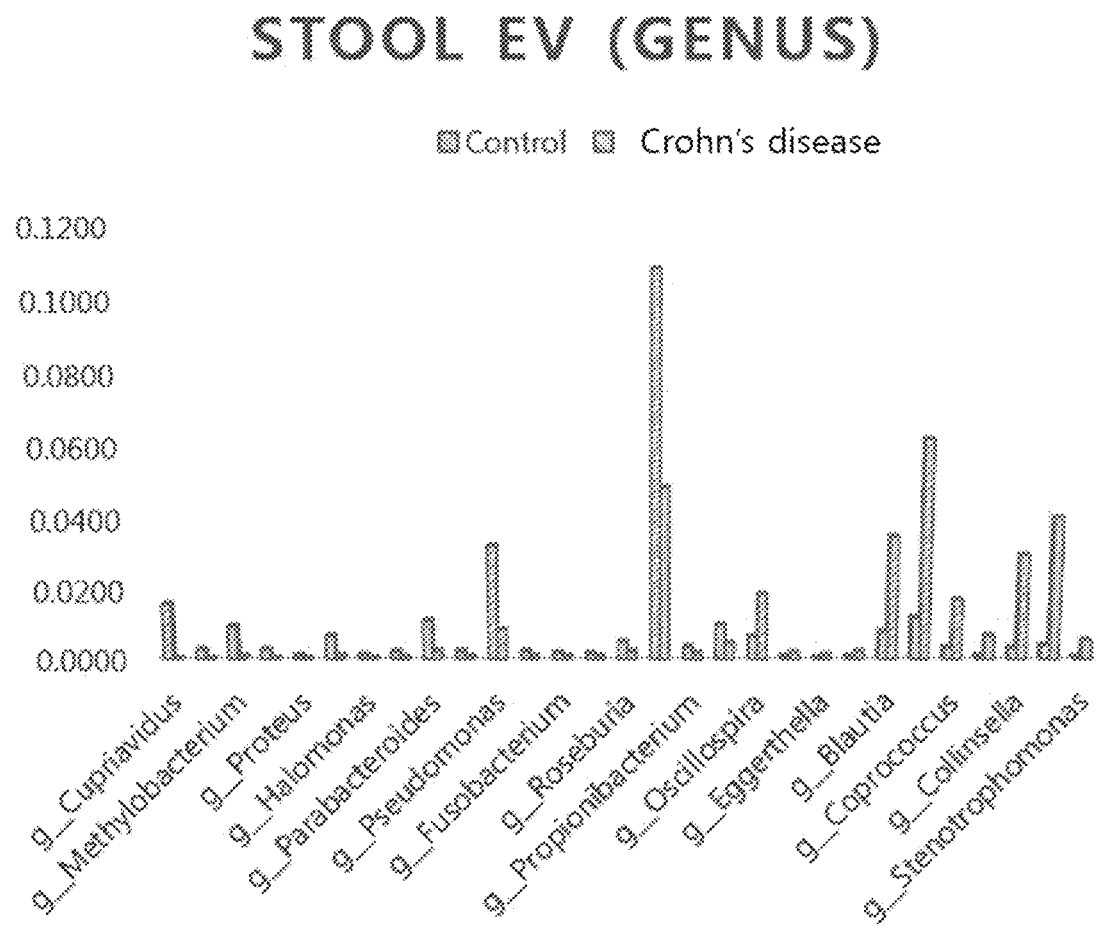
FIG. 21 is a result showing the distribution of bacteria-derived vesicles (EVs), which is significant in diagnostic performance at the genus level by isolating bacteria-derived vesicles from stool of a patient with Crohn's disease and a normal individual, and then performing a metagenomic analysis.
Figure 22:
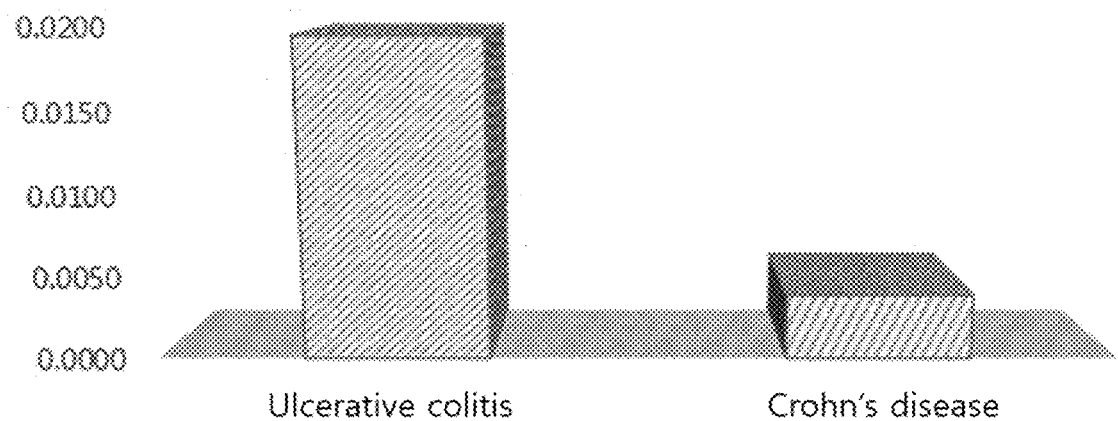
FIG. 22 is a result showing the distribution of bacteria, which is significant in diagnostic performance at the family level by isolating bacteria from stool of a patient with Crohn's disease and ulcerative colitis, and then performing a metagenomic analysis.
Figure 23:
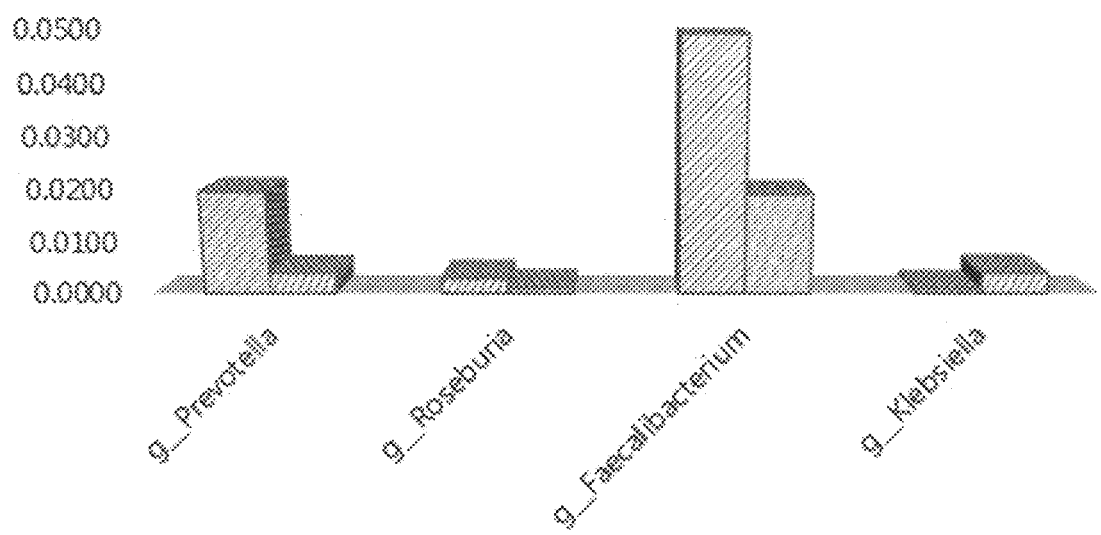
FIG. 23 is a result showing the distribution of bacteria, which is significant in diagnostic performance at the genus level by isolating bacteria from stool of a patient with Crohn's disease and ulcerative colitis, and then performing a metagenomic analysis.
Figure 24:
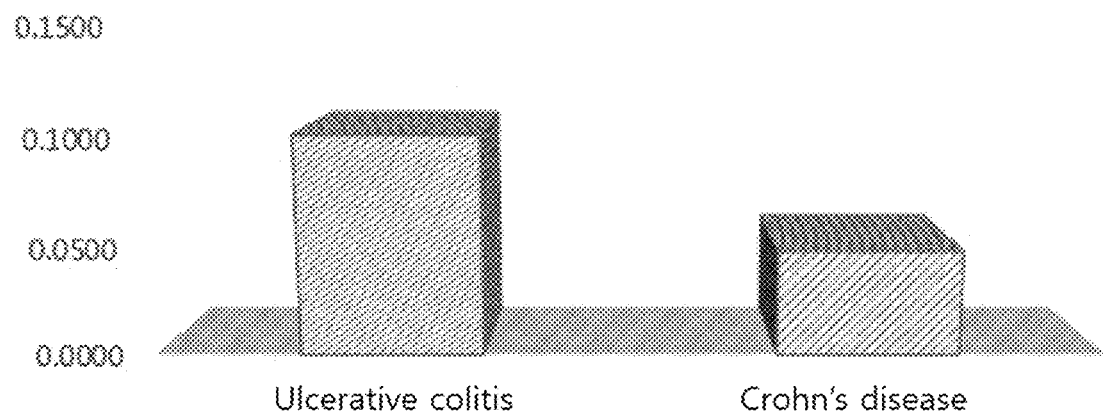
FIG. 24 is a result showing the distribution of bacteria-derived vesicles (EVs), which is significant in diagnostic performance at the family level by isolating bacteria-derived vesicles from stool of a patient with Crohn's disease and ulcerative colitis, and then performing a metagenomic analysis.
Figure 25:
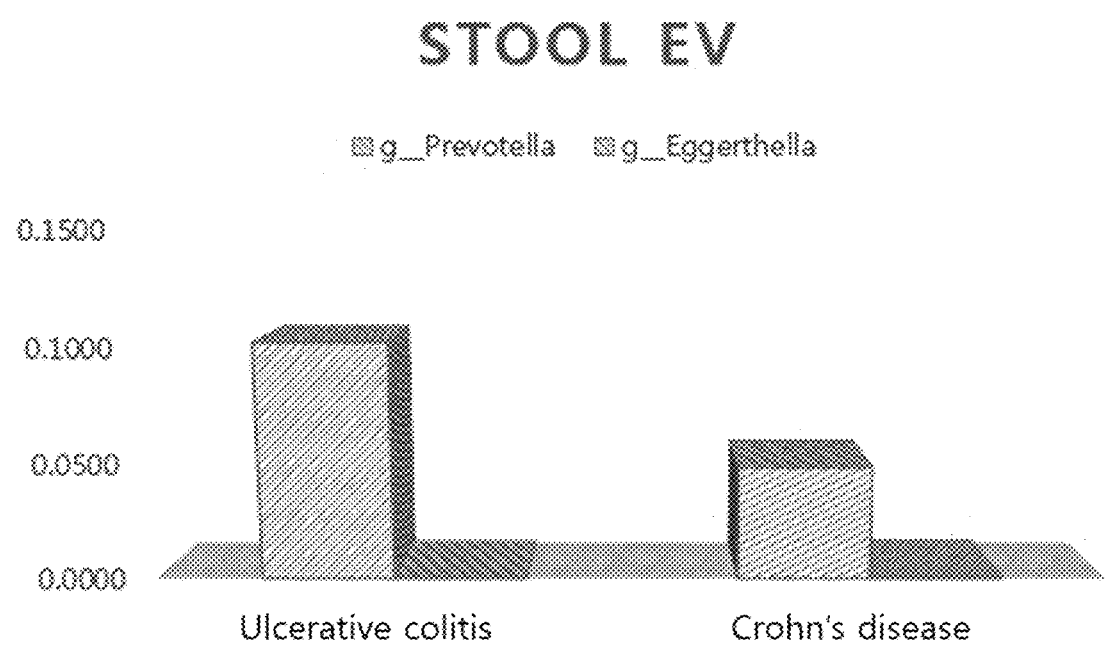
FIG. 25 is a result showing the distribution of bacteria-derived vesicles (EVs), which is significant in diagnostic performance at the genus level by isolating bacteria-derived vesicles from stool of a patient with Crohn's disease and ulcerative colitis, and then performing a metagenomic analysis.

As a result of analyzing vesicles derived from bacteria in stool at a genus level, a diagnostic model developed using vesicles derived from bacteria belonging to the genus *Cupriavidus*, the genus *Citrobacter*, the genus *Methylobacterium*, the genus *Paracoccus*, the genus *Proteus*, the genus *Enhydrobacter*, the genus *Halomonas*, the genus *Neisseria*, the genus *Parabacteroides*, the genus *Rothia*, the genus *Pseudomonas*, the genus *Bacillus*, the genus *Fusobacterium*, the genus *Lactococcus*, the genus *Roseburia*, the genus *Prevotella*, the genus *Propionibacterium*, the genus *Corynebacterium*, the genus *Oscillospira*, the genus *Klebsiella*, the genus *Eggerthella*, the genus *Rhodococcus*, the genus *Blautia*, the genus *Bifidobacterium*, the genus *Coprococcus*, the genus *Eubacterium*, the genus *Collinsella*, the genus *Ruminococcus*, and the genus *Stenotrophomonas* as a biomarker exhibited significant diagnostic performance for Crohn's disease (see Table 21 and FIG. 21).

TABLE 21

| Genus | Normal individual Mean | SD | Crohn's disease Mean | SD | t-test p-value | Ratio | AUC | Training Set Accuracy | sensitivity | specificity | AUC | Testing Set Accuracy | sensitivity | specificity |
|---|---|---|---|---|---|---|---|---|---|---|---|---|---|---|
| *Cupriavidus* | 0.0157 | 0.0619 | 0.0000 | 0.0000 | 0.0313 | 0.00 | 0.99 | 0.93 | 0.97 | 0.87 | 1.00 | 0.96 | 0.93 | 1.00 |
| *Citrobacter* | 0.0025 | 0.0044 | 0.0001 | 0.0003 | 0.0000 | 0.05 | 0.98 | 0.96 | 0.98 | 0.90 | 1.00 | 1.00 | 1.00 | 1.00 |
| *Methylobacterium* | 0.0092 | 0.0301 | 0.0006 | 0.0016 | 0.0163 | 0.07 | 0.98 | 0.93 | 0.98 | 0.84 | 1.00 | 1.00 | 1.00 | 1.00 |
| *Paracoccus* | 0.0025 | 0.0047 | 0.0002 | 0.0005 | 0.0001 | 0.07 | 0.98 | 0.95 | 0.98 | 0.87 | 1.00 | 1.00 | 1.00 | 1.00 |
| *Proteus* | 0.0010 | 0.0024 | 0.0001 | 0.0002 | 0.0015 | 0.07 | 0.97 | 0.95 | 0.98 | 0.87 | 1.00 | 1.00 | 1.00 | 1.00 |
| *Enhydrobacter* | 0.0066 | 0.0089 | 0.0010 | 0.0013 | 0.0000 | 0.15 | 0.98 | 0.96 | 0.98 | 0.90 | 1.00 | 1.00 | 1.00 | 1.00 |
| *Halomonas* | 0.0011 | 0.0032 | 0.0002 | 0.0005 | 0.0181 | 0.15 | 0.98 | 0.96 | 0.98 | 0.90 | 0.99 | 0.96 | 1.00 | 0.89 |
| *Neisseria* | 0.0021 | 0.0048 | 0.0003 | 0.0010 | 0.0032 | 0.15 | 0.97 | 0.93 | 0.98 | 0.84 | 1.00 | 1.00 | 1.00 | 1.00 |
| *Parabacteroides* | 0.0109 | 0.0268 | 0.0023 | 0.0031 | 0.0071 | 0.21 | 0.98 | 0.95 | 0.98 | 0.87 | 1.00 | 1.00 | 1.00 | 1.00 |
| *Rothia* | 0.0021 | 0.0032 | 0.0005 | 0.0009 | 0.0001 | 0.22 | 0.98 | 0.95 | 0.98 | 0.87 | 1.00 | 1.00 | 1.00 | 1.00 |
| *Pseudomonas* | 0.0322 | 0.0306 | 0.0082 | 0.0172 | 0.0000 | 0.26 | 0.97 | 0.95 | 0.98 | 0.87 | 1.00 | 1.00 | 1.00 | 1.00 |
| *Bacillus* | 0.0021 | 0.0038 | 0.0006 | 0.0016 | 0.0042 | 0.30 | 0.98 | 0.96 | 0.98 | 0.90 | 1.00 | 1.00 | 1.00 | 1.00 |
| *Fusobacterium* | 0.0016 | 0.0033 | 0.0005 | 0.0013 | 0.0133 | 0.32 | 0.97 | 0.95 | 0.98 | 0.87 | 1.00 | 1.00 | 1.00 | 1.00 |
| *Lactococcus* | 0.0014 | 0.0029 | 0.0005 | 0.0012 | 0.0345 | 0.38 | 0.98 | 0.95 | 0.98 | 0.87 | 1.00 | 1.00 | 1.00 | 1.00 |
| *Roseburia* | 0.0048 | 0.0100 | 0.0021 | 0.0037 | 0.0424 | 0.44 | 0.97 | 0.95 | 0.98 | 0.87 | 1.00 | 1.00 | 1.00 | 1.00 |
| *Prevotella* | 0.1083 | 0.1515 | 0.0485 | 0.1046 | 0.0152 | 0.45 | 0.97 | 0.96 | 1.00 | 0.87 | 1.00 | 1.00 | 1.00 | 1.00 |
| *Propionibacterium* | 0.0034 | 0.0050 | 0.0016 | 0.0025 | 0.0099 | 0.46 | 0.99 | 0.96 | 0.98 | 0.90 | 1.00 | 1.00 | 1.00 | 1.00 |
| *Corynebacterium* | 0.0097 | 0.0164 | 0.0045 | 0.0058 | 0.0149 | 0.46 | 0.98 | 0.96 | 0.98 | 0.90 | 1.00 | 1.00 | 1.00 | 1.00 |
| *Oscillospira* | 0.0063 | 0.0061 | 0.0185 | 0.0326 | 0.0263 | 2.92 | 0.97 | 0.96 | 1.00 | 0.87 | 1.00 | 1.00 | 1.00 | 1.00 |
| *Klebsiella* | 0.0005 | 0.0010 | 0.0017 | 0.0034 | 0.0333 | 3.55 | 0.99 | 0.97 | 1.00 | 0.90 | 1.00 | 1.00 | 1.00 | 1.00 |
| *Eggerthella* | 0.0003 | 0.0008 | 0.0011 | 0.0015 | 0.0030 | 3.76 | 0.97 | 0.96 | 1.00 | 0.87 | 1.00 | 1.00 | 1.00 | 1.00 |
| *Rhodococcus* | 0.0005 | 0.0007 | 0.0020 | 0.0041 | 0.0295 | 3.88 | 0.99 | 0.97 | 1.00 | 0.90 | 1.00 | 1.00 | 1.00 | 1.00 |
| *Blautia* | 0.0078 | 0.0190 | 0.0348 | 0.0312 | 0.0000 | 4.48 | 0.99 | 0.95 | 0.98 | 0.87 | 0.99 | 0.96 | 0.93 | 1.00 |
| *Bifidobacterium* | 0.0118 | 0.0124 | 0.0620 | 0.0513 | 0.0000 | 5.24 | 0.99 | 0.95 | 0.97 | 0.90 | 1.00 | 1.00 | 1.00 | 1.00 |
| *Coprococcus* | 0.0032 | 0.0035 | 0.0169 | 0.0279 | 0.0040 | 5.27 | 1.00 | 0.96 | 0.98 | 0.90 | 1.00 | 1.00 | 1.00 | 1.00 |
| [*Eubacterium*] | 0.0009 | 0.0016 | 0.0068 | 0.0100 | 0.0008 | 7.60 | 0.99 | 0.95 | 0.97 | 0.90 | 1.00 | 1.00 | 1.00 | 1.00 |
| *Collinsella* | 0.0032 | 0.0059 | 0.0296 | 0.0276 | 0.0000 | 9.29 | 0.99 | 0.95 | 0.97 | 0.90 | 1.00 | 1.00 | 1.00 | 1.00 |
| [*Ruminococcus*] | 0.0040 | 0.0092 | 0.0400 | 0.0959 | 0.0243 | 10.08 | 0.97 | 0.96 | 1.00 | 0.87 | 1.00 | 1.00 | 1.00 | 1.00 |
| *Stenotrophomonas* | 0.0004 | 0.0014 | 0.0054 | 0.0058 | 0.0000 | 12.92 | 0.98 | 0.95 | 0.98 | 0.87 | 1.00 | 1.00 | 1.00 | 1.00 |

Example 8. Inflammatory Bowel Disease Differential Diagnostic Model Based on Metagenomic Analysis of Bacteria Isolated from Stool of Ulcerative Colitis and Crohn's Disease Patient Bacteria was isolated from stool samples of 40 Crohn's disease patients and 70 ulcerative colitis patients, the two groups matched in age and gender, and then metagenomic sequencing was performed thereon using the method of Example 3. For the development of a diagnostic model, first, a strain exhibiting a p value of less than 0.05 between two groups in a t-test and a difference of two-fold or more between two groups was selected, and then an area under curve (AUC), sensitivity, and specificity, which are diagnostic performance indexes, were calculated by logistic regression analysis.

As a result of analyzing bacteria in stool at a family level, based on ulcerative colitis, the content of bacteria of the family Prevotellaceae associated with Crohn's disease was reduced. Therefore, the resulting analyte is able to be used as a marker for differential diagnosis of ulcerative colitis and Crohn's disease by development as a bacterial biomarker diagnostic model for the bacteria of the family Prevotellaceae.

TABLE 22

| Family | Ulcerative colitis Mean | SD | Crohn's disease Mean | SD | t-test p-value | Ratio | AUC | Training Set Accuracy | sensitivity | specificity | AUC | Testing Set Accuracy | sensitivity | specificity |
|---|---|---|---|---|---|---|---|---|---|---|---|---|---|---|
| Prevotellaceae | 0.0195 | 0.0451 | 0.0039 | 0.0082 | 0.0068 | 0.20 | 0.85 | 0.81 | 0.85 | 0.73 | 0.90 | 0.82 | 0.80 | 0.86 |

As a result of analyzing bacteria in stool at a genus level, based on ulcerative colitis, the content of bacteria of the genus *Klebsiella* associated with Crohn's disease was increased, whereas the contents of bacteria of the genus *Prevotella*, the genus *Roseburia* and the genus *Faecalibacterium* associated with Crohn's disease were reduced.

Therefore, the resulting analyte is able to be used as a marker for differential diagnosis of ulcerative colitis and Crohn's disease by development as a bacterial biomarker diagnostic model for bacteria of the genus *Klebsiella*, the genus *Prevotella*, the genus *Roseburia* and the genus *Faecalibacterium*.

TABLE 23

| Genus | Ulcerative colitis Mean | SD | Crohn's disease Mean | SD | t-test p-value | Ratio | AUC | Training Set Accuracy | sensitivity | specificity | AUC | Testing Set Accuracy | sensitivity | specificity |
|---|---|---|---|---|---|---|---|---|---|---|---|---|---|---|
| *Prevotella* | 0.0195 | 0.0451 | 0.0039 | 0.0082 | 0.0068 | 0.20 | 0.85 | 0.81 | 0.85 | 0.73 | 0.90 | 0.82 | 0.80 | 0.86 |
| *Roseburia* | 0.0028 | 0.0044 | 0.0010 | 0.0016 | 0.0024 | 0.35 | 0.85 | 0.81 | 0.85 | 0.73 | 0.91 | 0.82 | 0.80 | 0.86 |
| *Faecalibacterium* | 0.0485 | 0.0545 | 0.0189 | 0.0332 | 0.0007 | 0.39 | 0.88 | 0.81 | 0.85 | 0.73 | 0.87 | 0.64 | 0.60 | 0.71 |
| *Klebsiella* | 0.0007 | 0.0023 | 0.0039 | 0.0086 | 0.0286 | 5.29 | 0.87 | 0.82 | 0.87 | 0.73 | 0.90 | 0.86 | 0.87 | 0.86 |

Example 9. Inflammatory Bowel Disease Differential Diagnostic Model Based on Metagenomic Analysis of Bacteria-Derived Vesicles Isolated from Stool of Ulcerative Colitis and Crohn's Disease Patient Bacteria-derived vesicles was isolated from stool samples of 40 Crohn's disease patients and 70 ulcerative colitis patients, the two groups matched in age and gender, and then metagenomic sequencing was performed thereon using the method of Example 3. For the development of a diagnostic model, first, a strain exhibiting a p value of less than 0.05 between two groups in a t-test and a difference of two-fold or more between two groups was selected, and then an area under curve (AUC), sensitivity, and specificity, which are diagnostic performance indexes, were calculated by logistic regression analysis.

As a result of analyzing vesicles derived from bacteria in stool at a family level, based on ulcerative colitis, the content of vesicles derived from bacteria of the family Prevotellaceae associated with Crohn's disease was reduced. Therefore, the resulting analyte is able to be used as a marker for differential diagnosis of ulcerative colitis and Crohn's disease by development as a biomarker diagnostic model for the vesicles derived from bacteria of the family Prevotellaceae.

TABLE 24

| Family | Ulcerative colitis Mean | SD | Crohn's disease Mean | SD | t-test p-value | Ratio | AUC | Training Set Accuracy | sensitivity | specificity | AUC | Testing Set Accuracy | sensitivity | specificity |
|---|---|---|---|---|---|---|---|---|---|---|---|---|---|---|
| Prevotellaceae | 0.1019 | 0.1678 | 0.0485 | 0.1046 | 0.0455 | 0.48 | 0.85 | 0.79 | 0.81 | 0.76 | 0.81 | 0.86 | 0.93 | 0.71 |

As a result of analyzing vesicles derived from bacteria in stool at a genus level, based on ulcerative colitis, the content of vesicles derived from bacteria of the genus *Eggerthella* associated with Crohn's disease was increased, whereas the content of vesicles derived from bacteria of the genus *Prevotella* associated with Crohn's disease was reduced. Therefore, the resulting analyte is able to be used as a marker for differential diagnosis of ulcerative colitis and Crohn's disease by development as a biomarker diagnostic model for the vesicles derived from bacteria of the genus *Eggerthella*, and the genus *Prevotella*.

TABLE 25

| Genus | Ulcerative colitis Mean | SD | Crohn's disease Mean | SD | t-test p-value | Ratio | AUC | Training Set Accuracy | sensitivity | specificity | AUC | Testing Set Accuracy | sensitivity | specificity |
|---|---|---|---|---|---|---|---|---|---|---|---|---|---|---|
| *Prevotella* | 0.1019 | 0.1678 | 0.0485 | 0.1046 | 0.0455 | 0.48 | 0.85 | 0.79 | 0.81 | 0.76 | 0.81 | 0.86 | 0.93 | 0.71 |
| *Eggerthella* | 0.0005 | 0.0007 | 0.0011 | 0.0015 | 0.0168 | 2.37 | 0.85 | 0.80 | 0.85 | 0.73 | 0.76 | 0.82 | 0.93 | 0.57 |

INDUSTRIAL APPLICABILITY

By previously predicting a causative factor of inflammatory bowel disease and the risk of the onset of the disease through metagenomic analysis of bacteria or bacteria-derived vesicles using a human body-derived sample according to the present invention, the inflammatory bowel disease risk group may be diagnosed and predicted early, and the onset of the disease may be delayed or prevented with proper care. In addition, the vesicles may be used as a marker for differential diagnosis of ulcerative colitis and Crohn's disease through the above-mentioned analysis.

(f) analyzing the sequenced PCR products to determine the identity of the bacteria from which the EVs were derived and the and quantity of the bacteria-derived EVs; and (g-1) diagnosing ulcerative colitis by detecting an increase or decrease in the quantity of bacteria-derived EVs by two-fold or more in the stool sample of the subject as compared to that in samples obtained from normal, control individuals, (g-2) diagnosing Crohn's disease by detecting an increase or decrease in the quantity of bacteria-derived EVs by

What is claimed is:

1. A method of diagnosing an increased risk of ulcerative colitis or Crohn's disease, comprising the following processes:

(a) obtaining a stool sample from a subject;

(b) isolating extracellular vesicles (EVs) from the stool sample;

(c) extracting DNAs from the EVs;

(d) performing a polymerase chain reaction (PCR) on the extracted DNA using first primer set forth in SEQ ID NO: 1 and a second primer set forth in SEQ ID NO: 2 to produce PCR products;

(e) sequencing the PCR products;

two-fold or more in the stool sample of the subject as compared to that in samples obtained from normal, control individuals, (g-3) diagnosing Crohn's disease by detecting an increase or decrease in the quantity of bacteria-derived EVs by two-fold or more in the stool sample of the subject as compared to that in samples obtained from control patients having ulcerative colitis, wherein in (g-1), the EVs are derived from one or more bacteria selected from the group consisting of genus *Cupriavidus*, the genus *Paracoccus*, the genus *Methylobacterium*, the genus *Citrobacter*, the genus *Halomonas*, the genus *Bacillus*, the genus *Pseudomonas*, the genus *Micrococcus*, the genus *Enhydrobacter*, the genus *Proteus*, the genus *Neisseria*, the genus *Rothia*, the genus *Propionibacterium*, the genus *Staphylococcus*, the genus *Acinetobacter*, the genus *Corynebacterium*, the genus *Fusobacterium*, the genus *Streptococcus*, the genus *Rhodococcus*, the genus *Klebsiella*, the genus *Blautia*, the genus *Peptoniphilus*, the genus *Bifidobacterium*, the genus *Coprococcus*, the genus *Eubacterium*, the genus *Dorea*, the genus *Collinsella*, and the genus *Stenotrophomonas*, the increase in the quantity of bacteria-derived EVs by two-fold or more is in the EVs derived from the bacteria consisting of the genus *Streptococcus*, the genus *Rhodococcus*, the genus *Klebsiella*, the genus *Blautia*, the genus *Peptoniphilus*, the genus *Bifidobacterium*, the genus *Coprococcus*, the genus *Eubacterium*, the genus *Dorea*, the genus *Collinsella*, and the genus *Stenotrophomonas*, and the decrease in the quantity of bacteria-derived EVs by two-fold or more is in the EVs derived from the bacteria consisting of the genus *Cupriavidus*, the genus *Paracoccus*, the genus *Methylobacterium*, the genus *Citrobacter*, the genus *Halomonas*, the genus *Bacillus*, the genus *Pseudomonas*, the genus *Micrococcus*, the genus *Enhydrobacter*, the genus *Proteus*, the genus *Neisseria*, the genus *Rothia*, the genus *Propionibacterium*, the genus *Staphylococcus*, the genus *Acinetobacter*, the genus *Corynebacterium*, and the genus *Fusobacterium*, wherein in (g-2), the EVs are derived from one or more bacteria selected from the group consisting of the genus *Cupriavidus*, the genus *Citrobacter*, the genus *Methylobacterium*, the genus *Paracoccus*, the genus *Proteus*, the genus *Enhydrobacter*, the genus *Halomonas*, the genus *Neisseria*, the genus *Parabacteroides*, the genus *Rothia*, the genus *Pseudomonas*, the genus *Bacillus*, the genus *Fusobacterium*, the genus *Lactococcus*, the genus *Roseburia*, the genus *Prevotella*, the genus *Propionibacterium*, the genus *Corynebacterium*, the genus *Oscillospira*, the genus *Klebsiella*, the genus *Eggerthella*, the genus *Rhodococcus*, the genus *Blautia*, the genus *Bifidobacterium*, the genus *Coprococcus*, the genus *Eubacterium*, the genus *Collinsella*, the genus *Ruminococcus*, and the genus *Stenotrophomonas*, the increase in the quantity of bacteria-derived EVs by two-fold or more is in the EVs derived from the bacteria consisting of the group consisting of the genus *Oscillospira*, the genus *Klebsiella*, the genus *Eggerthella*, the genus *Rhodococcus*, the genus *Blautia*, the genus *Bifidobacterium*, the genus *Coprococcus*, the genus *Eubacterium*, the genus *Collinsella*, the genus *Ruminococcus*, and the genus *Stenotrophomonas*, the decrease in the quantity of bacteria-derived EVs by two-fold or more is in the EVs derived from the bacteria consisting of the genus *Cupriavidus*, the genus *Citrobacter*, the genus *Methylobacterium*, the genus *Paracoccus*, the genus *Proteus*, the genus *Enhydrobacter*, the genus *Halomonas*, the genus *Neisseria*, the genus *Parabacteroides*, the genus *Rothia*, the genus *Pseudomonas*, the genus *Bacillus*, the genus *Fusobacterium*, the genus *Lactococcus*, the genus *Roseburia*, the genus *Prevotella*, the genus *Propionibacterium*, and the genus *Corynebacterium*, and wherein in (g-3), the EVs are derived from one or more bacteria selected from the group consisting of the genus *Prevotella*, and the genus *Eggerthella*, the increase in the quantity of bacteria-derived EV by two-fold or more is in the EVs derived from bacteria of the genus *Eggerthella*, and the decrease in the quantity of bacteria-derived EV by two-fold or more is in the EVs derived from bacteria of the genus *Prevotella*.

* * * * *